(12) United States Patent
Haensel et al.

(10) Patent No.: US 10,519,375 B2
(45) Date of Patent: Dec. 31, 2019

(54) LIQUID-CRYSTAL MEDIUM

(71) Applicant: MERCK PATENT GMBH, Darmstadt (DE)

(72) Inventors: Helmut Haensel, Muehltal (DE); Andreas Pohle, Pfungstadt (DE); Brigitte Schuler, Grossostheim (DE); Christian Jasper, Seligenstadt (DE)

(73) Assignee: MERCK PATENT GMBH, Darmstadt (DE)

( * ) Notice: Subject to any disclaimer, the term of this patent is extended or adjusted under 35 U.S.C. 154(b) by 50 days.

(21) Appl. No.: 15/571,988

(22) PCT Filed: Apr. 8, 2016

(86) PCT No.: PCT/EP2016/000583
§ 371 (c)(1),
(2) Date: Nov. 6, 2017

(87) PCT Pub. No.: WO2016/177445
PCT Pub. Date: Nov. 10, 2016

(65) Prior Publication Data
US 2018/0134960 A1    May 17, 2018

(30) Foreign Application Priority Data
May 4, 2015    (EP) .................................... 15001316

(51) Int. Cl.
*C09K 19/06*    (2006.01)
*C09K 19/34*    (2006.01)
(Continued)

(52) U.S. Cl.
CPC ........ *C09K 19/3402* (2013.01); *C07C 69/587* (2013.01); *C07C 69/602* (2013.01); *C07C 69/80* (2013.01); *C07D 311/16* (2013.01); *C07D 311/30* (2013.01); *C07H 15/10* (2013.01); *C09K 19/0208* (2013.01); *C09K 19/062* (2013.01); *C09K 19/067* (2013.01); *C09K 19/3003* (2013.01); *C09K 19/3066* (2013.01); *C09K 19/542* (2013.01); *C07C 2601/14* (2017.05); *C09K 2019/0466* (2013.01); *C09K 2019/122* (2013.01); *C09K 2019/123* (2013.01); *C09K 2019/124* (2013.01); *C09K 2019/301* (2013.01); *C09K 2019/3004* (2013.01); *C09K 2019/3009* (2013.01); *C09K 2019/3012* (2013.01); *C09K 2019/3019* (2013.01);
(Continued)

(58) Field of Classification Search
CPC ..................................................... C09K 19/54
See application file for complete search history.

(56) References Cited

U.S. PATENT DOCUMENTS

2013/0207038 A1* 8/2013 Haensel ............... C09K 19/062
                                                        252/299.61
2013/0299741 A1* 11/2013 Zhong ................. C09K 19/062
                                                        252/999.5

FOREIGN PATENT DOCUMENTS

EP    2628779 A2    8/2013

OTHER PUBLICATIONS

International Search Report PCT/EP2016/000583 dated Jun. 27, 2016.

* cited by examiner

*Primary Examiner* — Chanceity N Robinson
(74) *Attorney, Agent, or Firm* — Millen White Zelano and Branigan, PC; Csaba Henter

(57) ABSTRACT

The invention relates to a liquid-crystalline medium which comprises at least one compound of the formula I,

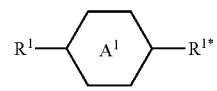

in which
$R^1$ and $R^{1*}$ each, independently of one another, denote an alkyl or alkoxy radical having 1 to 15 C atoms, where, in addition, one or more $CH_2$ groups in these radicals may each be replaced, independently of one another, by

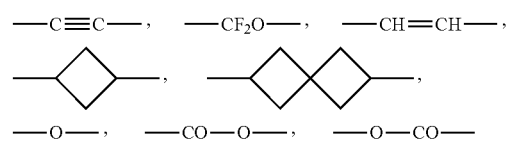

in such a way that O atoms are not linked directly to one another, and in which, in addition, one or more H atoms may be replaced by halogen,
$A^1$ denotes

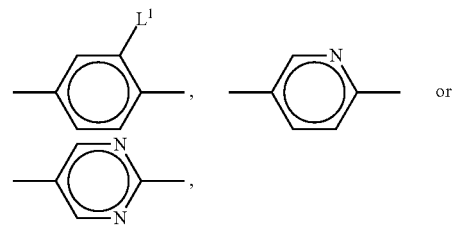

(Continued)

$L^1$ denotes F, Cl, $CF_3$, $OCF_3$ or $CHF_2$,
and to the use thereof for electro-optical purposes, in particular for shutter glasses, 3D applications, in TN, PS-TN, STN, TN-TFT, OCB, IPS, PS-IPS, FFS, PS-FFS and PS-VA-IPS displays.

20 Claims, No Drawings

(51) Int. Cl.
| | |
|---|---|
| *C09K 19/30* | (2006.01) |
| *C07C 69/587* | (2006.01) |
| *C07C 69/602* | (2006.01) |
| *C07C 69/80* | (2006.01) |
| *C07D 311/16* | (2006.01) |
| *C07D 311/30* | (2006.01) |
| *C07H 15/10* | (2006.01) |
| *C09K 19/02* | (2006.01) |
| *C09K 19/54* | (2006.01) |
| C09K 19/04 | (2006.01) |
| C09K 19/12 | (2006.01) |
| G02F 1/137 | (2006.01) |

(52) U.S. Cl.
CPC ............... *C09K 2019/3025* (2013.01); *C09K 2019/3042* (2013.01); *C09K 2019/3422* (2013.01); *C09K 2019/548* (2013.01); *G02F 1/13725* (2013.01); *G02F 2001/13706* (2013.01); *G02F 2001/13775* (2013.01)

LIQUID-CRYSTAL MEDIUM

The invention relates to a liquid-crystalline medium which comprises at least one compound of the formula I,

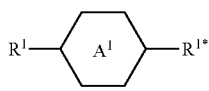

in which
$R^1$ and $R^{1*}$ each, independently of one another, denote an alkyl or alkoxy radical having 1 to 15 C atoms, where, in addition, one or more $CH_2$ groups in these radicals may each be replaced, independently of one another, by

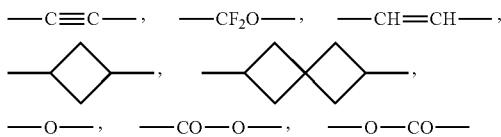

in such a way that O atoms are not linked directly to one another, and in which, in addition, one or more H atoms may be replaced by halogen,
$A^1$ denotes

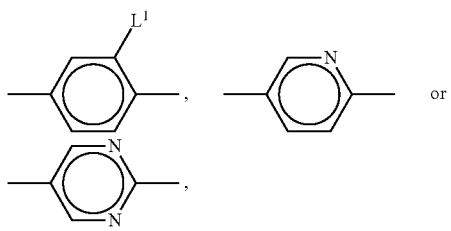

$L^1$ denotes F, Cl, $CF_3$, $OCF_3$ or $CHF_2$.

Liquid crystals are used principally as dielectrics in display devices, since the optical properties of such substances can be modified by an applied voltage. Electro-optical devices based on liquid crystals are extremely well known to the person skilled in the art and can be based on various effects. Examples of such devices are cells having dynamic scattering, DAP (deformation of aligned phases) cells, guest/host cells, TN cells having a twisted nematic structure, STN (supertwisted nematic) cells, SBE (superbirefringence effect) cells and OMI (optical mode interference) cells. The commonest display devices are based on the Schadt-Helfrich effect and have a twisted nematic structure.

The liquid-crystal materials must have good chemical and thermal stability and good stability to electric fields and electromagnetic radiation. Furthermore, the liquid-crystal materials should have low viscosity and produce short addressing times, low threshold voltages and high contrast in the cells.

They should furthermore have a suitable mesophase, for example a nematic or cholesteric mesophase for the above-mentioned cells, at the usual operating temperatures, i.e. in the broadest possible range above and below room temperature. Since liquid crystals are generally used as mixtures of a plurality of components, it is important that the components are readily miscible with one another. Further properties, such as the electrical conductivity, the dielectric anisotropy and the optical anisotropy, have to satisfy various requirements depending on the cell type and area of application. For example, materials for cells having a twisted nematic structure should have positive dielectric anisotropy and low electrical conductivity.

For example, for matrix liquid-crystal displays with integrated non-linear elements for switching individual pixels (MLC displays), media having large positive dielectric anisotropy, broad nematic phases, relatively low birefringence, very high specific resistance, good UV and temperature stability and low vapour pressure are desired.

Matrix liquid-crystal displays of this type are known. Examples of non-linear elements which can be used to individually switch the individual pixels are active elements (i.e. transistors). The term "active matrix" is then used, where a distinction can be made between two types:
1. MOS (metal oxide semiconductor) or other diodes on silicon wafers as substrate.
2. Thin-film transistors (TFTs) on a glass plate as substrate.

The use of single-crystal silicon as substrate material restricts the display size, since even modular assembly of various part-displays results in problems at the joints.

In the case of the more promising type 2, which is preferred, the electro-optical effect used is usually the TN effect. A distinction is made between two technologies: TFTs comprising compound semiconductors, such as, for example, CdSe, or TFTs based on polycrystalline or amorphous silicon. Intensive work is being carried out worldwide on the latter technology.

The TFT matrix is applied to the inside of one glass plate of the display, while the other glass plate carries the transparent counterelectrode on its inside. Compared with the size of the pixel electrode, the TFT is very small and has virtually no adverse effect on the image. This technology can also be extended to fully colour-capable displays, in which a mosaic of red, green and blue filters is arranged in such a way that a filter element is opposite each switchable pixel.

The TFT displays usually operate as TN cells with crossed polarisers in transmission and are backlit.

The term MLC displays here encompasses any matrix display with integrated non-linear elements, i.e., besides the active matrix, also displays with passive elements, such as varistors or diodes (MIM=metal-insulator-metal).

MLC displays of this type are particularly suitable for TV applications (for example pocket televisions) or for high-information displays for computer applications (laptops) and in automobile or aircraft construction. Besides problems regarding the angle dependence of the contrast and the response times, difficulties also arise in MLC displays due to insufficiently high specific resistance of the liquid-crystal mixtures [TOGASHI, S., SEKIGUCHI, K., TANABE, H., YAMAMOTO, E., SORIMACHI, K., TAJIMA, E., WATANABE, H., SHIMIZU, H., Proc. Eurodisplay 84, September 1984: A 210-288 Matrix LCD Controlled by Double Stage Diode Rings, pp. 141 ff, Paris; STROMER, M., Proc. Eurodisplay 84, September 1984: Design of Thin Film Transistors for Matrix Addressing of Television Liquid Crystal Displays, pp. 145 ff, Paris]. With decreasing resistance, the contrast of an MLC display deteriorates, and the problem of after-image elimination may occur. Since the specific resistance of the liquid-crystal mixture generally drops over the life of an MLC display owing to interaction with the interior surfaces of the display, a high (initial) resistance is very important in order to obtain acceptable lifetimes. In particular in the case of low-volt mixtures, it was hitherto impossible to achieve very high specific resistance values. It is furthermore important that the specific resistance exhibits the smallest possible increase with increasing temperature and after heating and/or UV exposure. The low-temperature properties of the mixtures from the prior art are also particularly disadvantageous. It is demanded that no crystallisation and/or smectic phases occur, even at low temperatures, and the temperature dependence of the viscosity is as low as possible. The MLC displays from the prior art thus do not satisfy today's requirements.

Besides liquid-crystal displays which use backlighting, i.e. are operated transmissively and if desired transflectively, reflective liquid-crystal displays are also particularly interesting. These reflective liquid-crystal displays use the ambient light for information display. They thus consume significantly less energy than backlit liquid-crystal displays having a corresponding size and resolution. Since the TN effect is characterised by very good contrast, reflective displays of this type can even be read well in bright ambient conditions. This is already known of simple reflective TN displays, as used, for example, in watches and pocket calculators. However, the principle can also be applied to high-quality, higher-resolution active matrix-addressed displays, such as, for example, TFT displays. Here, as already in the transmissive TFT-TN displays which are generally conventional, the use of liquid crystals of low birefringence ($\Delta n$) is necessary in order to achieve low optical retardation ($d \cdot \Delta n$). This low optical retardation results in usually acceptable low viewing-angle dependence of the contrast (cf. DE 30 22 818). In reflective displays, the use of liquid crystals of low birefringence is even more important than in transmissive displays since the effective layer thickness through which the light passes is approximately twice as large in reflective displays as in transmissive displays having the same layer thickness.

In order to achieve 3D effects by means of shutter glasses, fast-switching mixtures having low rotational viscosities and correspondingly high optical anisotropy ($\Delta n$), in particular, are employed. Electro-optical lens systems, by means of which a 2-dimensional representation of a display can be switched to a 3-dimensional autostereoscopic representation, can be achieved using mixtures having high optical anisotropy ($\Delta n$).

Thus, there continues to be a great demand for MLC displays having very high specific resistance at the same time as a large working-temperature range, short response times, even at low temperatures, and a low threshold voltage which do not exhibit these disadvantages or only do so to a lesser extent.

In the case of TN (Schadt-Helfrich) cells, media are desired which facilitate the following advantages in the cells:
extended nematic phase range (in particular down to low temperatures)
switchability at extremely low temperatures (outdoor use, automobiles, avionics)
increased resistance to UV radiation (longer life)
low threshold voltage.

The media available from the prior art do not enable these advantages to be achieved while simultaneously retaining the other parameters.

In the case of supertwisted (STN) cells, media are desired which facilitate greater multiplexability and/or lower threshold voltages and/or broader nematic phase ranges (in particular at low temperatures). To this end, a further widening of the available parameter latitude (clearing point, smectic-nematic transition or melting point, viscosity, dielectric parameters, elastic parameters) is urgently desired.

In particular in the case of LC displays for TV and video applications (for example LCD-TVs, monitors, PDAs, notebooks, games consoles), a significant reduction in the response times is desired. This requires LC mixtures having low rotational viscosities and high values for the birefringence $\Delta n$.

The invention has the object of providing media, in particular for MLC, FFS, IPS, TN, positive VA or STN displays of this type, which do not exhibit the disadvantages indicated above or only do so to a lesser extent and preferably have fast response times and low rotational viscosities at the same time as a high clearing point, as well as high dielectric anisotropy and a low threshold voltage.

It has now been found that this object can be achieved if LC media comprising one or more compounds of the formula I are used. The compounds of the formula I result in LC mixtures having the desired properties indicated above.

So-called monocyclic compounds (compounds containing one ring) generally cannot be used in nematic liquid-crystal mixtures owing to the poor phase properties and low clearing points. However, the compounds of the formula I surprisingly simultaneously have very low rotational viscosities, high absolute values of the dielectric anisotropy, comparatively high absolute values of the optical anisotropy, good solubilities in liquid-crystal mixtures, and comparatively low volatility. It is therefore possible to prepare liquid-crystal mixtures, preferably IPS and/or FFS mixtures, which have short response times, at the same time good phase properties and good low-temperature behaviour.

The invention thus relates to a liquid-crystalline medium which comprises at least one compound of the formula I.

The mixtures according to the invention preferably exhibit very broad nematic phase ranges with clearing points $\geq 70°$ C., preferably $\geq 75°$ C., in particular $\geq 80°$ C., very favourable values for the capacitive threshold, relatively high values for the holding ratio and at the same time very good low-temperature stabilities (LTS) at $-20°$ C. and $-30°$ C., as well as very low rotational viscosities and short response times. The mixtures according to the invention are furthermore distinguished by the fact that, in addition to the improvement in the rotational viscosity $\gamma^1$, relatively high values of the elastic constants $K_{33}$ are observed for improving the response times.

Some preferred embodiments of the mixtures according to the invention are indicated below.

In the compounds of the formula I, $R^1$ and $R^{1*}$ each, independently of one another, preferably denote straight-chain alkoxy, in particular $OC_2H_5$, $OC_3H_7$, $OC_4H_9$, $OC_5H_{11}$, $OC_6H_{13}$, furthermore alkenyloxy, in particular $OCH_2CH=CH_2$, $OCH_2CH=CHCH_3$, $OCH_2CH=CHC_2H_5$, furthermore alkyl, in particular n-$C_3H_7$, n-$C_4H_9$, n-$C_5H_{11}$, n-$C_6H_{13}$.

$R^1$ and $R^{1*}$ particularly preferably each, independently of one another, denote straight-chain alkoxy having 1-6 C atoms, in particular ethoxy, butoxy, pentoxy, hexoxy or straight-chain alkenyloxy having 2-6 C atoms, in particular $OCH_2CH=CH_2$.

Preferred compounds of the formula I are the compounds of the formulae I-1 to I-10,

I-1

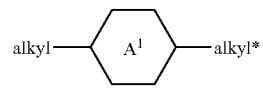

-continued

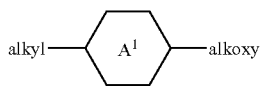 I-2

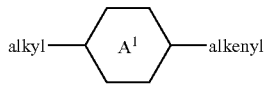 I-3

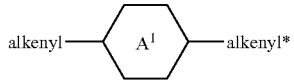 I-4

 I-5

 I-6

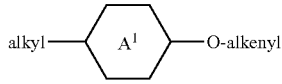 I-7

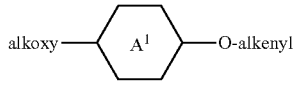 I-8

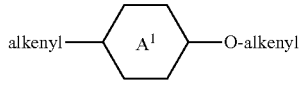 I-9

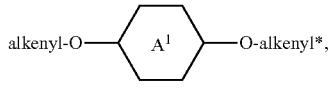 I-10 in which
alkyl and alkyl* each, independently of one another, denote a straight-chain alkyl radical having 1-6 C atoms,
alkenyl and alkenyl* each, independently of one another, denote a straight-chain alkenyl radical having 2-6 C atoms,
alkoxy and alkoxy* each, independently of one another, denote a straight-chain alkoxy radical having 1-6 C atoms,
and $A^1$ has the meaning indicated under formula I.

In the compounds of the formulae I-1 to I-10, $A^1$ preferably denotes

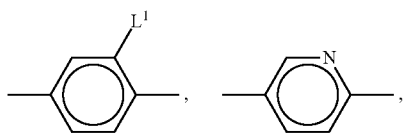

in particular

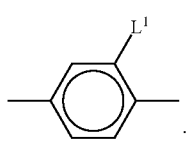

Particular preference is given to the compounds of the formula I-6.

The mixture according to the invention very particularly preferably comprises at least one compound of the formula I-6A or I-6B:

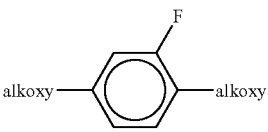 I-6A

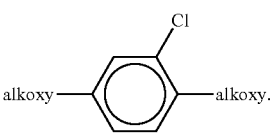 I-6B

The mixtures according to the invention very particularly preferably comprise at least one compound from the following group:

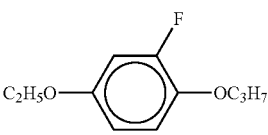 I-6A-1

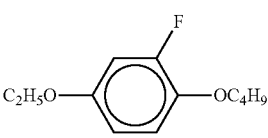 I-6A-2

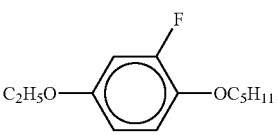 I-6A-3

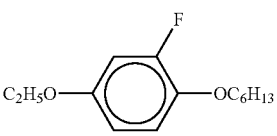 I-6A-4

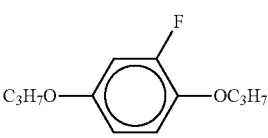 I-6A-5

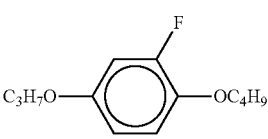 I-6A-6

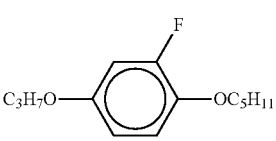 I-6A-7

-continued

I-6A-8
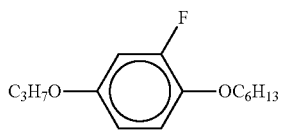

I-6A-9
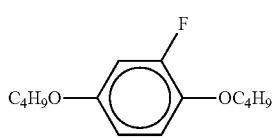

I-6A-10
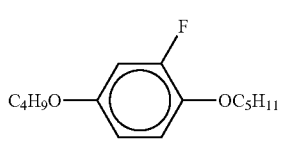

I-6A-11
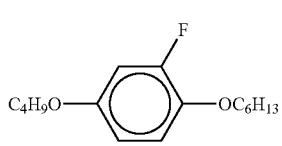

I-6A-12
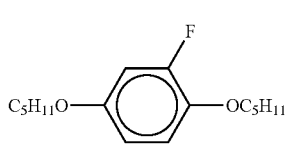

I-6A-13
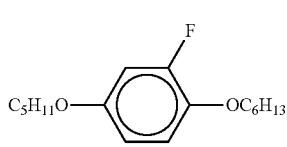

I-6A-14
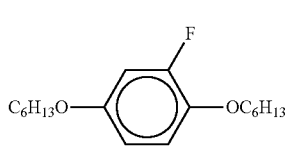

I-8A-1
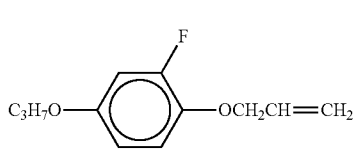

I-8A-2
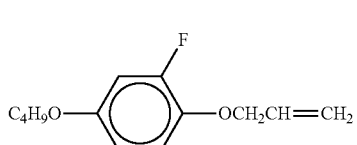

I-8A-3
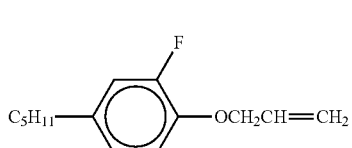

I-8A-4
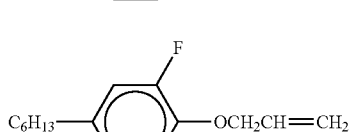

I-8A-5
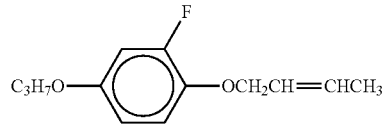

I-8A-6
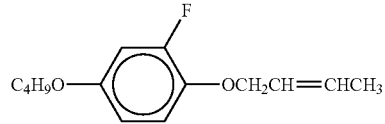

I-8A-7
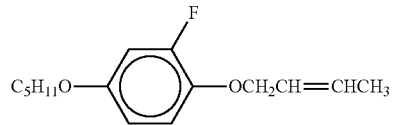

I-8A-8
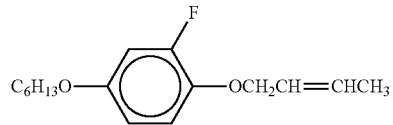

I-8A-9
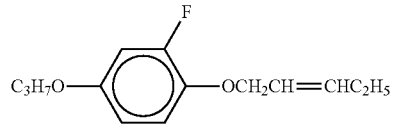

I-8A-10
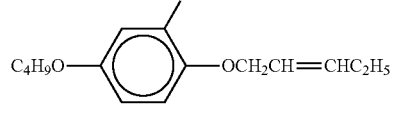

I-8A-11
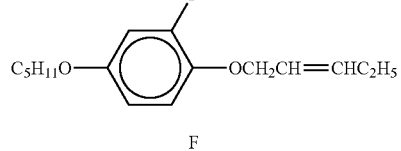

I-8A-12
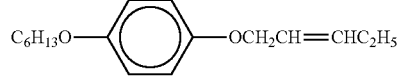

In the compounds of the formula I and the sub-formulae, $R^1$ and $R^{1*}$ preferably both denote alkoxy.

The compounds of the formula I are prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and suitable for the said reactions. Use can also be made here of variants known per se which are not mentioned here in greater detail. However, the compounds of the formula I can also be prepared in an analogous manner to that indicated in WO 2011/64789 or WO 2010/127208.

The media according to the invention preferably comprise one, two, three, four or more, preferably one, two or three, compounds of the formula I.

The compounds of the formula I are preferably employed in the liquid-crystalline medium in amounts of ≥0.5% by weight, preferably ≥1% by weight, based on the mixture as a whole. Particular preference is given to liquid-crystalline media which comprise 0.5-15% by weight of one or more compounds of the formula I.

Further preferred embodiments are indicated below:
The medium additionally comprises one or more compounds of the formulae II and/or III

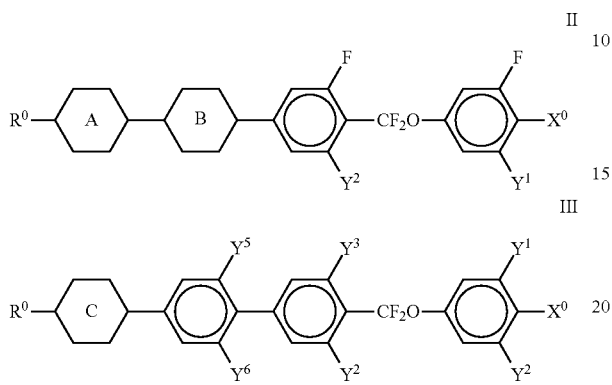

in which
R⁰ denotes a halogenated or unsubstituted alkyl or alkoxy radical having 1 to 15 C atoms, where, in addition, one or more $CH_2$ groups in these radicals may each be replaced, independently of one another, by

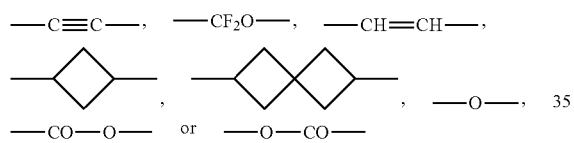

in such a way that O atoms are not linked directly to one another, $X^0$ denotes F, Cl, CN, $SF_5$, SCN, NCS, a halogenated alkyl radical, a halogenated alkenyl radical, a halogenated alkoxy radical or a halogenated alkenyloxy radical having up to 6 C atoms, and $Y^{1-6}$ each, independently of one another, denote H or F,

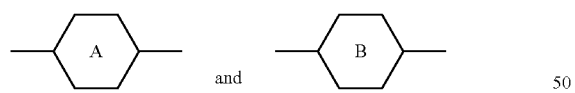

each, independently of one another, denote

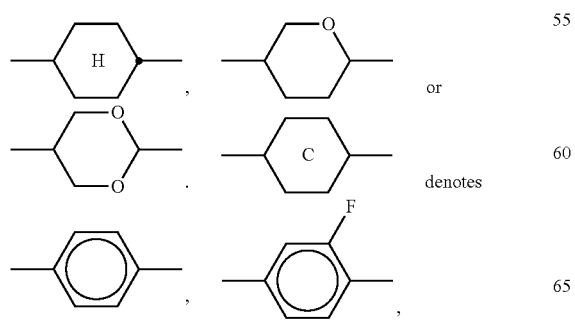

denotes

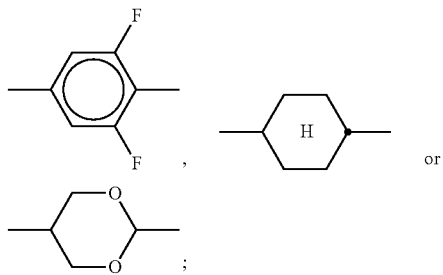

and

The compounds of the formulae II and III are preferably selected from the following formulae:

IIa
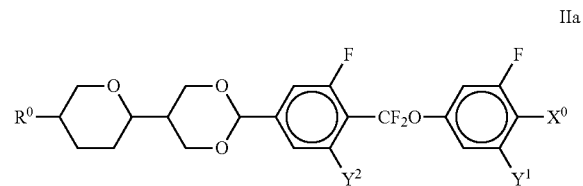

IIb

IIc
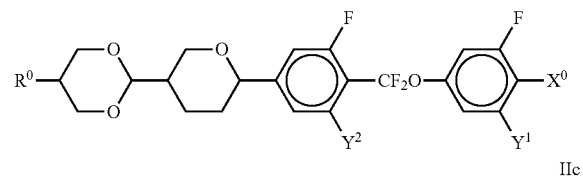

IId

IIe
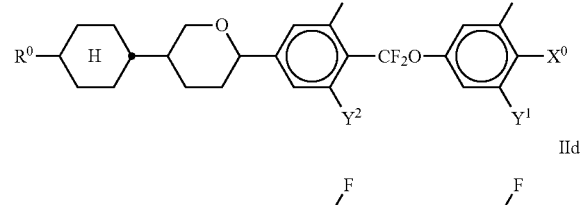

IIf
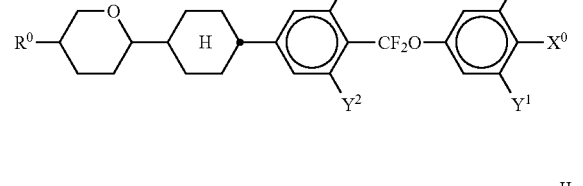

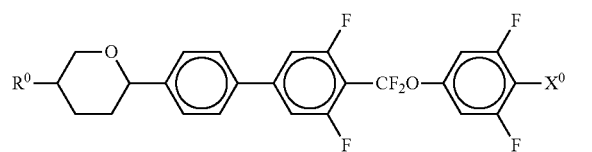
IIIa

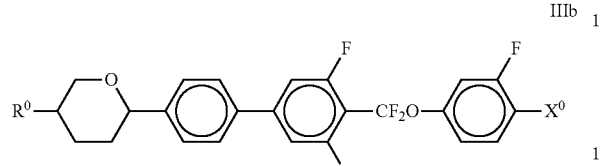
IIIb

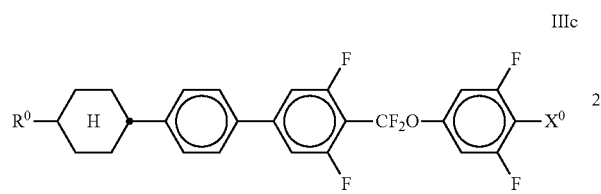
IIIc

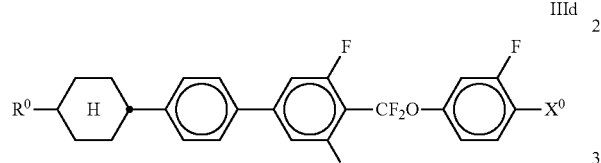
IIId

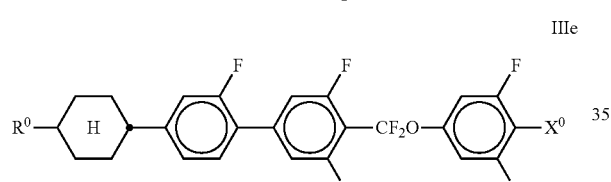
IIIe

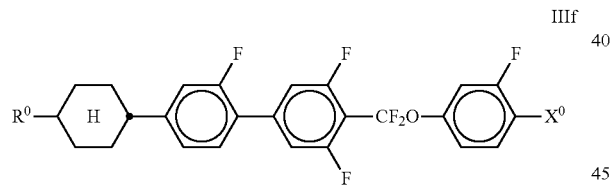
IIIf

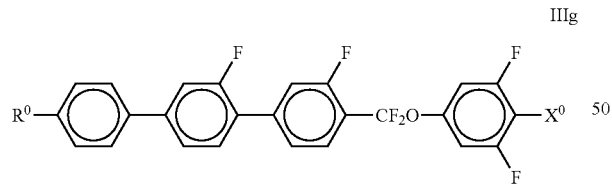
IIIg

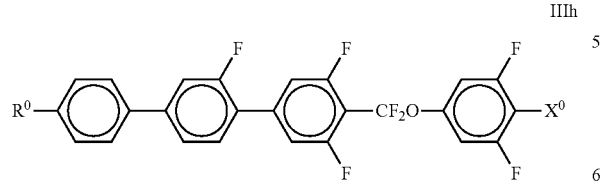
IIIh

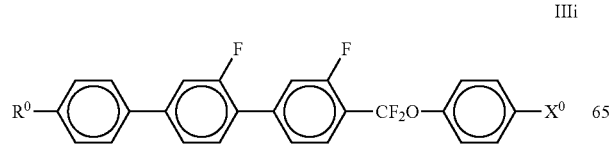
IIIi

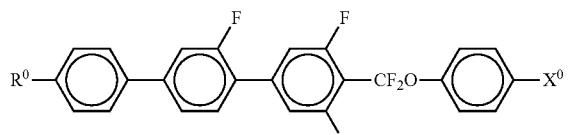
IIIj

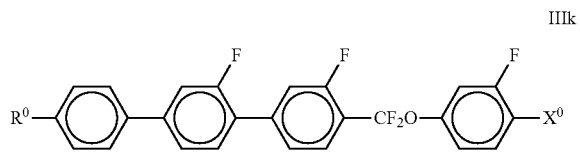
IIIk

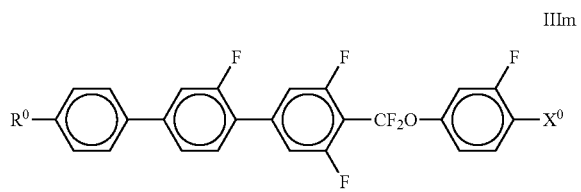
IIIm in which $R^0$ and $X^0$ have the meanings indicated above.

$R^0$ preferably denotes alkyl having 1 to 6 C atoms. $X^0$ preferably denotes F, furthermore $OCF_3$. Particularly preferred compounds of the formulae II and IIa-f are those in which $Y^1$ denotes F and $Y^2$ denotes H or F, preferably F. The mixture according to the invention particularly preferably comprises at least one compound of the formula IIIh.

The medium optionally comprises one or more compounds selected from the following formulae:

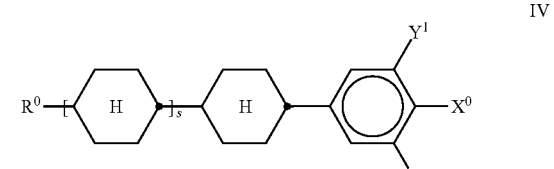
IV

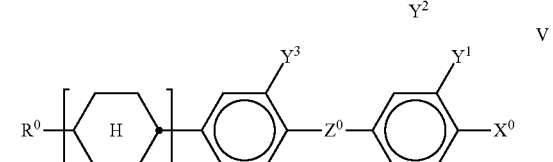
V

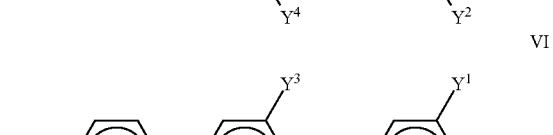
VI

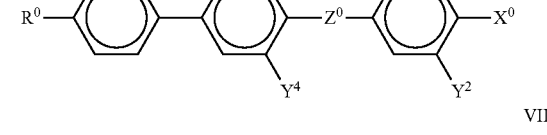

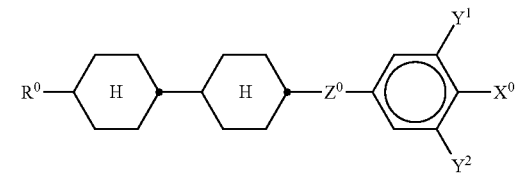
VII

VIII

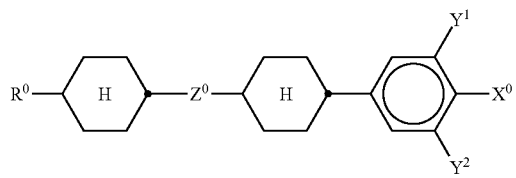

in which
R⁰, X⁰ and Y¹⁻⁴ have the meanings indicated above, and Z⁰ denotes —C₂H₄—, —(CH₂)₄—, —CH=CH—, —CF=CF—, —C₂F₄—, —CH₂CF₂—, —CF₂CH₂—, —CH₂O—, —OCH₂—, —COO—, —CF₂O— or —OCF₂—, in formulae V and VI also a single bond,
r denotes 0 or 1, and
s denotes 0 or 1;

The compounds of the formula IV are preferably selected from the following formulae:

IVa

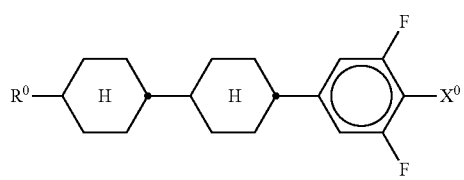

IVb

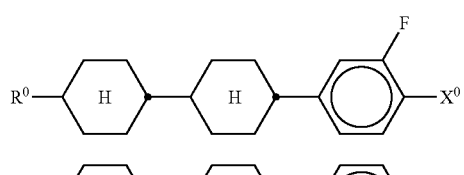

IVc

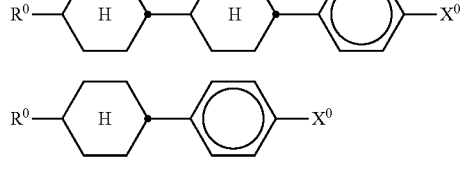

IVd

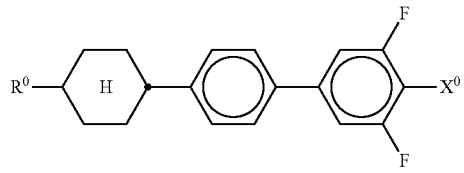

in which R⁰ and X⁰ have the meanings indicated above.
R⁰ preferably denotes alkyl having 1 to 6 C atoms. X⁰ preferably denotes F or OCF₃, furthermore CF₃, OCF=CF₂ or Cl;

The compounds of the formula V are preferably selected from the following formulae:

Va

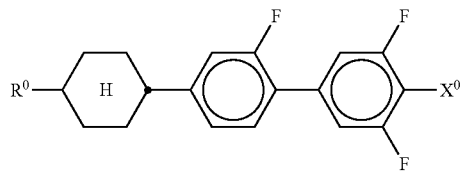

Vb

Vc

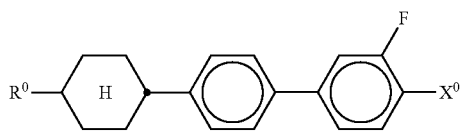

Vd

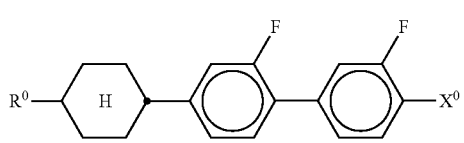

Ve

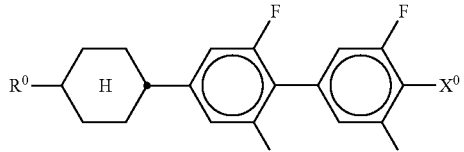

Vf

Vg

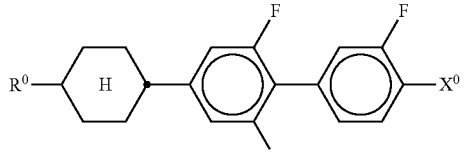

Vh

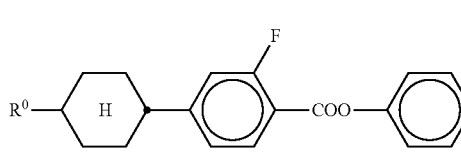

in which R⁰ and X⁰ have the meanings indicated above.
R⁰ preferably denotes alkyl having 1 to 6 C atoms. X⁰ preferably denotes F and OCF₃, furthermore OCHF₂, CF₃, OCF=CF₂ and OCH=CF₂;

The compounds of the formula VI are preferably selected from the following formulae:

VIa

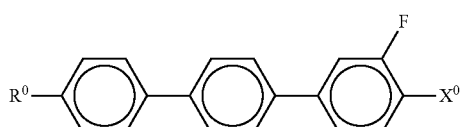

VIb

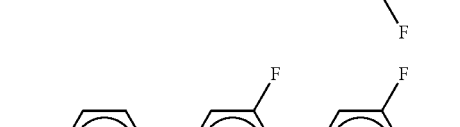

VIc

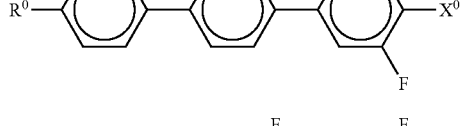

-continued

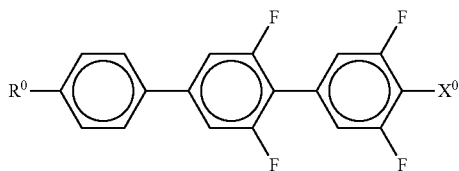

VId in which $R^0$ and $X^0$ have the meanings indicated above.

$R^0$ preferably denotes alkyl having 1 to 6 C atoms. $X^0$ preferably denotes F, furthermore $OCF_3$, $CF_3$, $CF{=}CF_2$, $OCHF_2$ and $OCH{=}CF_2$;

The compounds of the formula VII are preferably selected from the following formulae:

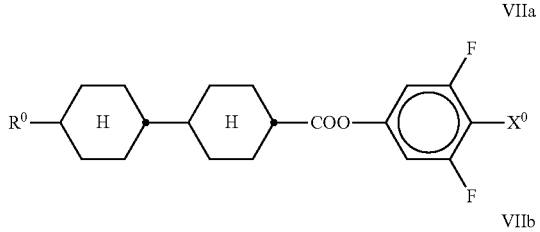

VIIa

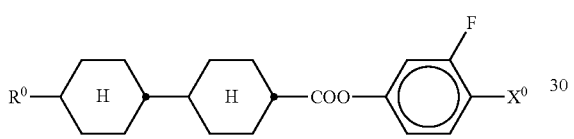

VIIb in which $R^0$ and $X^0$ have the meanings indicated above.

$R^0$ preferably denotes alkyl having 1 to 6 C atoms. $X^0$ preferably denotes F, furthermore $OCF_3$, $OCHF_2$ and $OCH{=}CF_2$.

The medium preferably comprises one or more compounds selected from the following formulae:

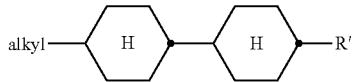

IX

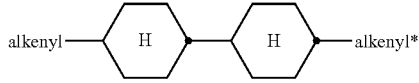

X

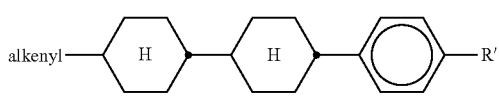

XI

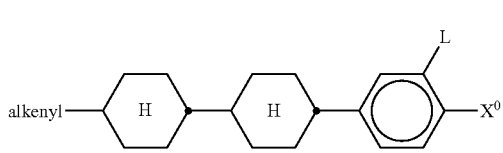

XII in which $X^0$ has the meanings indicated above, and
L denotes H or F,
"alkyl" denotes $C_{1-6}$-alkyl,
R' denotes $C_{1-6}$-alkyl, $C_{1-6}$-alkoxy or $C_{2-6}$-alkenyl, and
"alkenyl" and "alkenyl*" each, independently of one another, denote $C_{2-6}$-alkenyl.

The compounds of the formulae IX-XII are preferably selected from the following formulae:

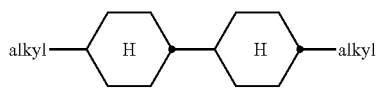

IXa

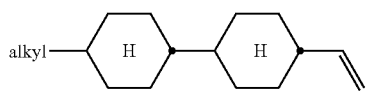

IXb

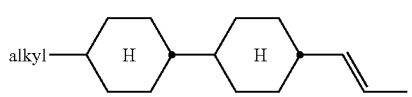

IXc

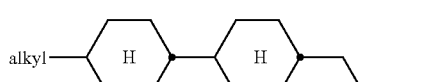

IXd

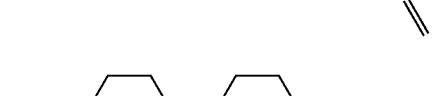

IXe

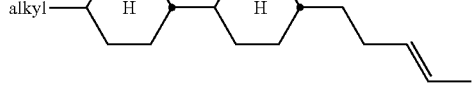

Xa

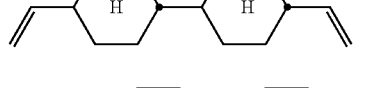

Xb

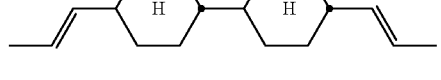

XIa

XIIa

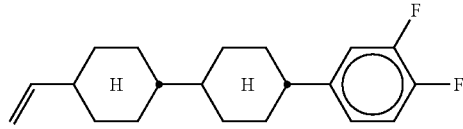

in which "alkyl" has the meaning indicated above.

Particular preference is given to the compounds of the formulae IXa, IXb, IXc, Xa, Xb, XIa and XIIa. In the formulae IXb and IX, "alkyl" preferably, independently of one another, denotes n-$C_3H_7$, n-$C_4H_9$ or n-$C_5H_{11}$, in particular n-$C_3H_7$.

The medium optionally comprises one or more compounds selected from the following formulae:

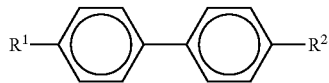

XIII

XIV

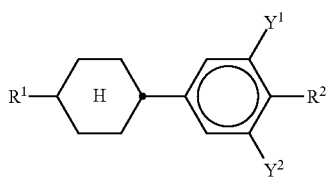

XV

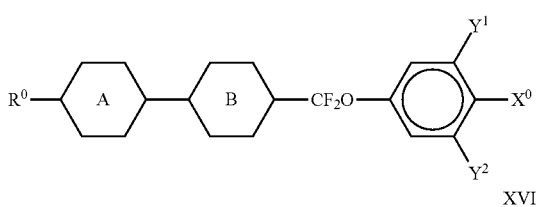

in which $Y^1$ and $Y^2$ have the meanings indicated above, and $R^1$ and $R^2$ each, independently of one another, denote n-alkyl, alkoxy, oxaalkyl, fluoroalkyl or alkenyl, each having up to 6 C atoms, and preferably each, independently of one another, denote alkyl having 1 to 6 C atoms; in the compound of the formula XIII, at least one of the radicals $R^1$ and $R^2$ preferably denotes alkenyl having 2 to 6 C atoms.

The medium preferably comprises one or more compounds of the formula XIII in which at least one of the radicals $R^1$ and $R^2$ denotes alkenyl having 2 to 6 C atoms, preferably those selected from the following formulae:

XIIIa

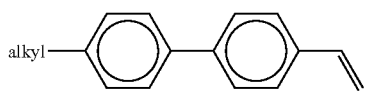

XIIIb

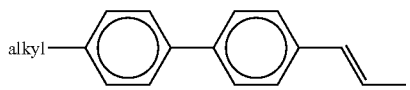

XIIIc

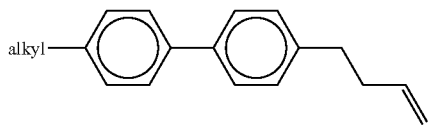

XIIId

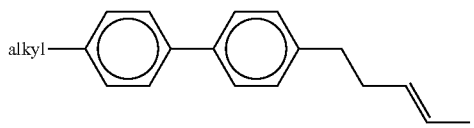

in which "alkyl" has the meaning indicated above;

The medium comprises one or more compounds of the formula XIIIe,

XIIIe

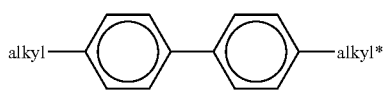

in which "alkyl" and "alkyl*" have the meanings indicated above;

The medium optionally comprises one or more compounds of the formula XV and/or XVI,

XVI

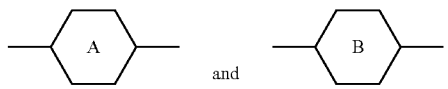

in which $R^0$, $X^0$ and $Y^{1-4}$ have the meanings indicated in formula I, and

each, independently of one another, denote

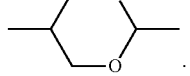

The compounds of the formula XV are preferably selected from the following formulae:

XVa

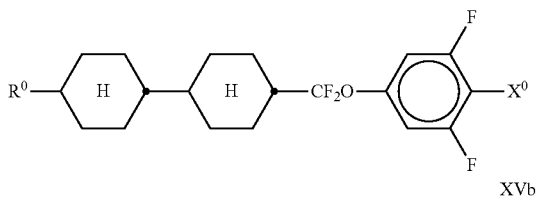

XVb

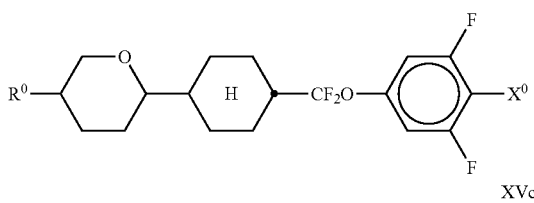

XVc

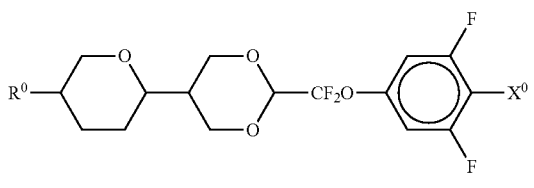

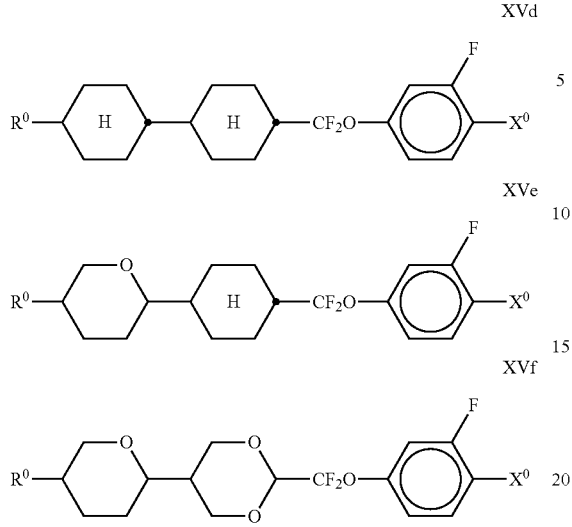

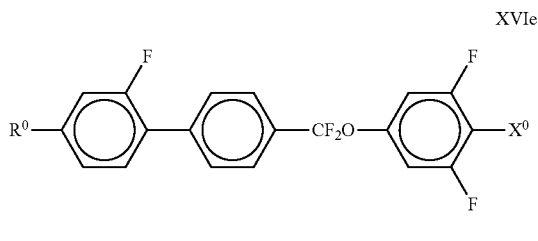

in which R⁰ and X⁰ have the meanings indicated above.

R⁰ preferably denotes alkyl having 1 to 6 C atoms. X⁰ preferably denotes F, furthermore OCF$_3$ and CF$_3$. Particular preference is given to compounds of the formulae XVIa and XVIe, in particular compounds of the formula XVIa;

The medium preferably comprises one or more compounds of the formula XVII,

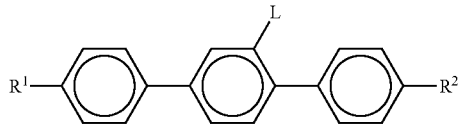

in which R⁰ and X⁰ have the meanings indicated above.

R⁰ preferably denotes alkyl having 1 to 6 C atoms. X⁰ preferably denotes F, furthermore OCF$_3$ and CF$_3$. Particular preference is given to compounds of the formulae XVa and XVb, in particular compounds of the formulae XVa and XVb in which X⁰ denotes F.

The compounds of the formula XVI are preferably selected from the following formlae:

in which R¹ and R² have the meanings indicated above and preferably each, independently of one another, denote alkyl having 1 to 6 C atoms. L denotes H or F.

Particularly preferred compounds of the formula XVII are those of the sub-formulae

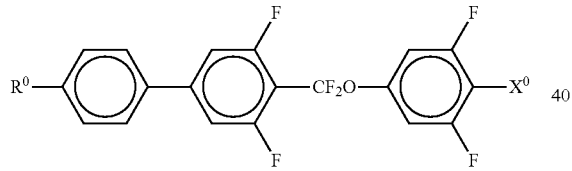

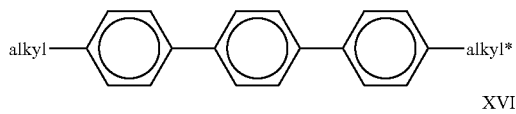

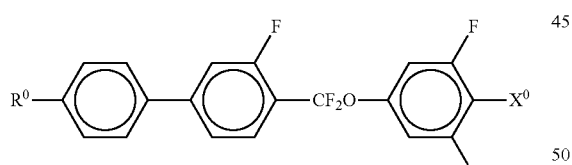

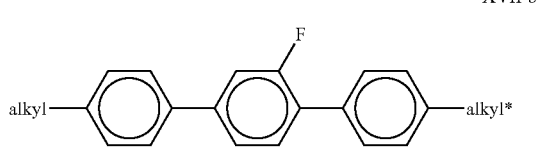

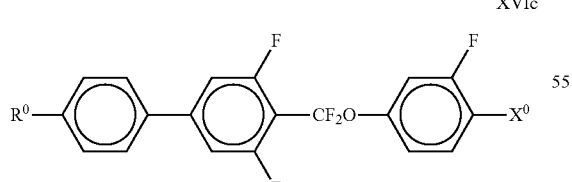

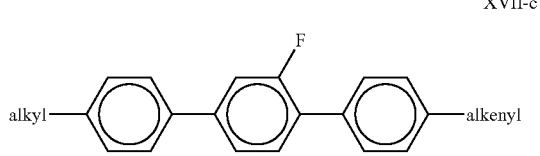

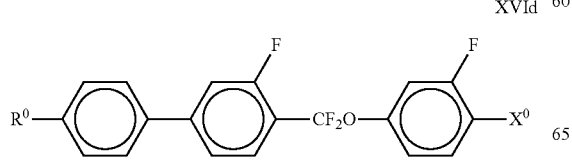

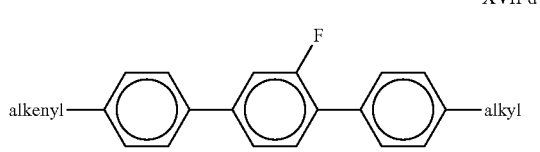

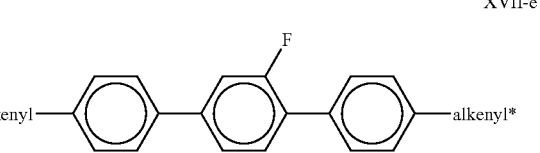

-continued

XVII-f

in which
alkyl and alkyl* each, independently of one another, denote a straight-chain alkyl radical having 1-6 C atoms, in particular ethyl, propyl and pentyl,
alkenyl and alkenyl* each, independently of one another, denote a straight-chain alkenyl radical having 2-6 C atoms, in particular $CH_2=CHC_2H_4$, $CH_3CH=CHC_2H_4$, $CH_2=CH$ and $CH_3CH=CH$.

Particular preference is given to the compounds of the formulae XVII-b and XVII-c. Very particular preference is given to the compounds of the formulae

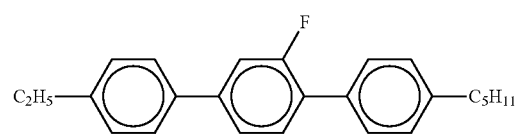

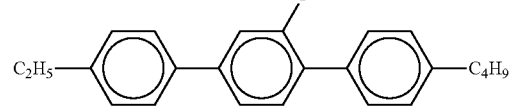

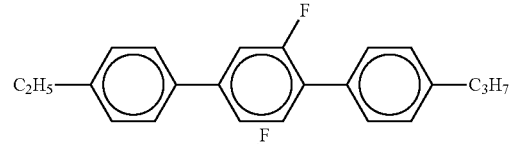

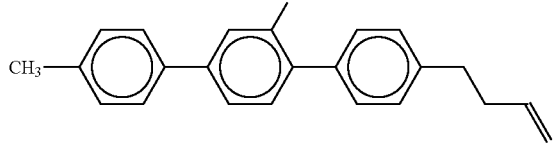

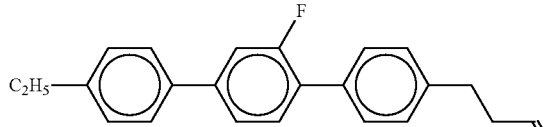

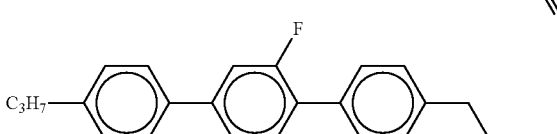

The medium preferably comprises one or more compounds of the following formulae:

XVIIIa

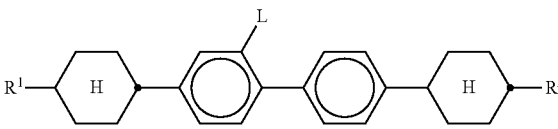

-continued

XVIIIb

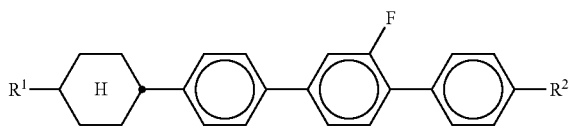

in which $R^1$ and $R^2$ have the meanings indicated above and preferably each, independently of one another, denote alkyl having 1 to 6 C atoms. L denotes H or F;

The medium optionally comprises one or more compounds selected from the following formulae:

XIX

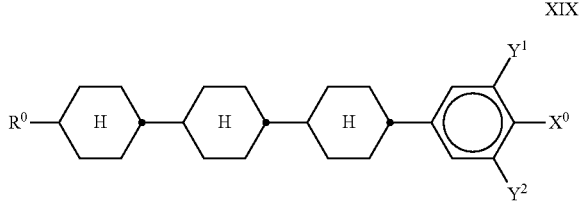

XX

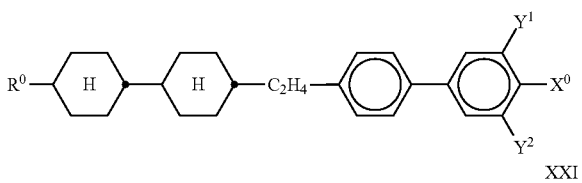

XXI

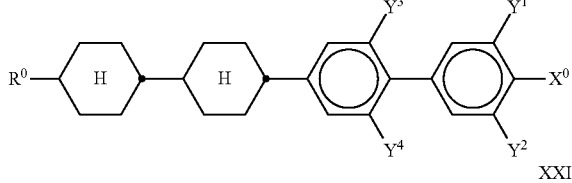

XXII

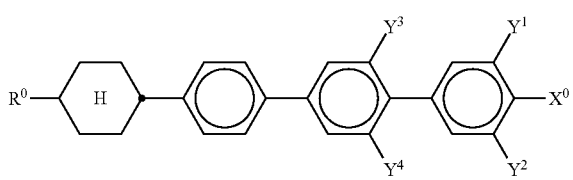

XXIII

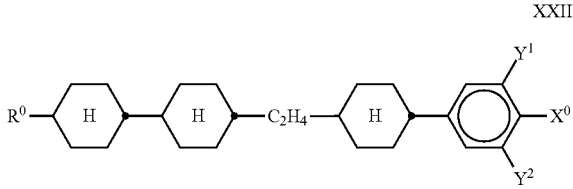

XXIV

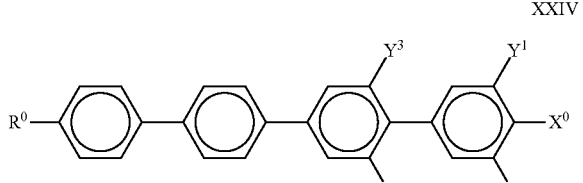

in which $R^0$, $Y^{1-4}$ and $X^0$ each, independently of one another, have one of the meanings indicated above. $Y^{1-4}$ each, independently of one another, preferably denote H or F. $X^0$ is preferably F, Cl, CF$_3$, OCF$_3$ or OCHF$_2$. R$^0$ preferably denotes alkyl, alkoxy, oxaalkyl, fluoroalkyl or alkenyl, each having up to 6 C atoms.

The mixture according to the invention particularly preferably comprises one or more compounds of the formula XXIV-a,

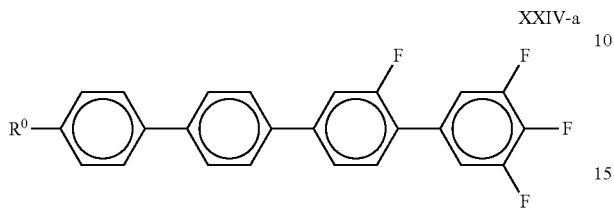

XXIV-a in which R$^0$ has the meanings indicated above. R$^0$ preferably denotes straight-chain alkyl, in particular ethyl, n-propyl, n-butyl and n-pentyl and very particularly preferably n-propyl. The compound(s) of the formula XXIV-a is (are) preferably employed in the mixtures according to the invention in amounts of 0.5-20% by weight, particularly preferably 1-15% by weight.

The medium optionally comprises one or more compounds of the formula XXIV,

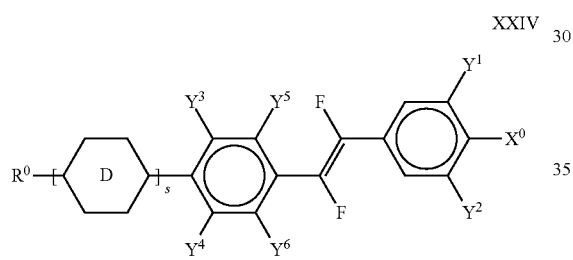

XXIV in which R$^0$, X$^0$ and Y$^{1-6}$ have the meaning indicated above, s denotes 0 or 1, and

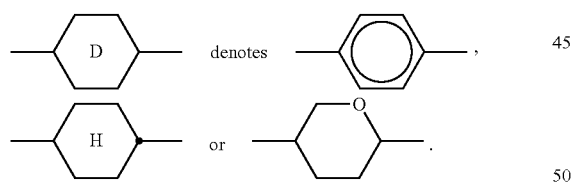

In the formula XXIV, X$^0$ may also denote an alkyl radical having 1-6 C atoms or an alkoxy radical having 1-6 C atoms. The alkyl or alkoxy radical is preferably straight-chain.

R$^0$ preferably denotes alkyl having 1 to 6 C atoms. X$^0$ preferably denotes F;

The compounds of the formula XXIV are preferably selected from the following formulae:

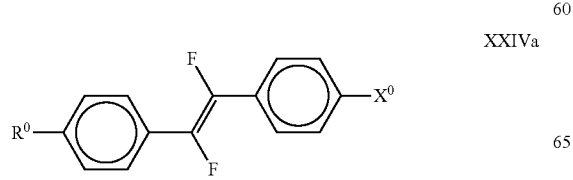

XXIVa

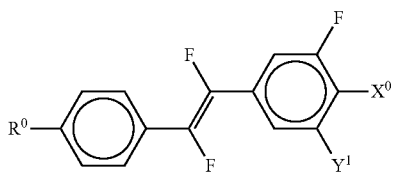

XXIVb

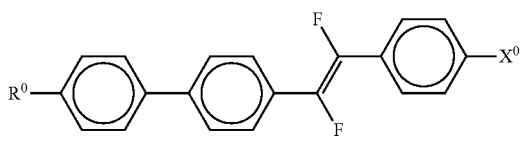

XXIVc

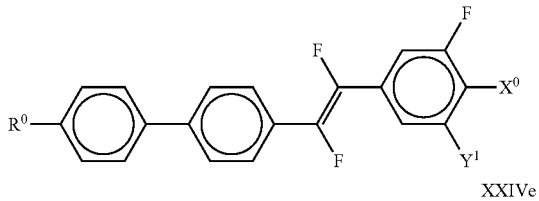

XXIVd

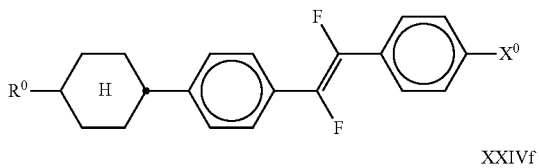

XXIVe

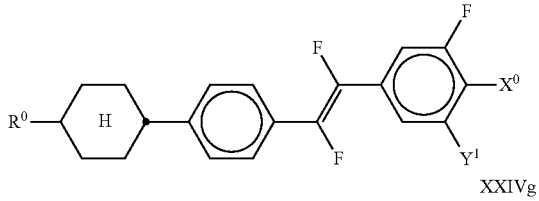

XXIVf

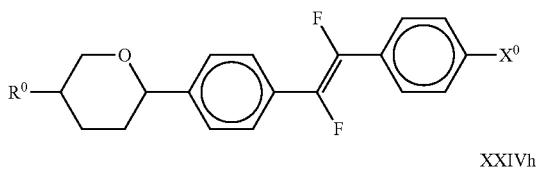

XXIVg

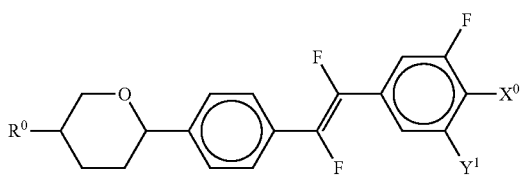

XXIVh in which R$^0$, X$^0$ and Y$^1$ have the meanings indicated above. R$^0$ preferably denotes alkyl having 1 to 6 C atoms. X$^0$ preferably denotes F, and Y$^1$ is preferably F;

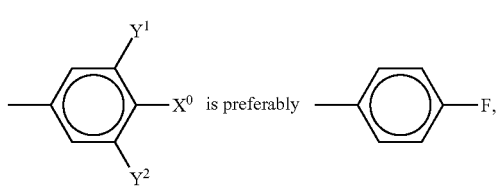

$R^0$ is straight-chain alkyl or alkenyl having 2 to 6 C atoms;

The medium preferably comprises one or more compounds of the following formulae:

XXV

XXVI in which $R^0$ and $X^0$ have the meanings indicated above. $R^0$ preferably denotes alkyl having 1 to 6 C atoms. $X^0$ preferably denotes F or Cl. In the formula XXV, $X^0$ very particularly preferably denotes Cl.

The medium preferably comprises one or more compounds of the following formulae:

XXVII

XXVIII

XXIX in which $R^0$ and $X^0$ have the meanings indicated above. $R^0$ preferably denotes alkyl having 1 to 6 C atoms. $X^0$ preferably denotes F. The medium according to the invention particularly preferably comprises one or more compounds of the formula XXIX in which $X^0$ preferably denotes F. The compound(s) of the formulae XXVII-XXIX is (are) preferably employed in the mixtures according to the invention in amounts of 1-20% by weight, particularly preferably 1-15% by weight. Particularly preferred mixtures comprise at least one compound of the formula XXIX.

In particular, the medium optionally comprises one or more compounds of the following formulae:

XXX

XXXI

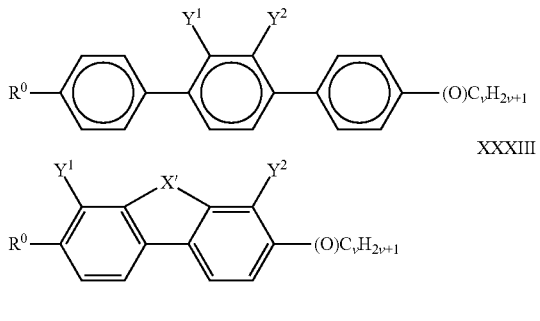

in which

R⁰, X⁰, Y¹ and Y² have the meanings indicated above,

X' denotes —O— or —S—,

Z² and Z²' each, independently of one another, denote a single bond, —CH₂CH₂—, =CH—, —CF₂O—, —OCF₂—, —CH₂O—, —OCH₂—, —COO—, —OCO—, —C₂F₄—, —CF=CF—, —CH=CHCH₂O—, denotes 0, 1 or 2, q denotes 0 or 1, and v denotes 1 to 6.

In the compounds of the formulae XXX and XXXI, $Z^2$ may have identical or different meanings. In the compounds of the formula XXXI, $Z^2$ and $Z^{2'}$ may have identical or different meanings.

In the compounds of the formulae XXX, XXXI, XXXII and XXXIII, R⁰ in each case preferably denotes alkyl having 1-6 C atoms, in particular CH₃, C₂H₅, n-C₃H₇, n-C₄H₉, n-C₅H₁₁.

In the compounds of the formula XXXIII, R⁰ additionally preferably denotes alkoxy having 1-6 C atoms, in particular —OCH₃, —OC₂H₅, —OC₃H₇, —OC₄H₉, —OC₅H₁₁.

In the compounds of the formulae XXXI, XXXII and XXXIII, preferably Y¹=Y²=F, Y¹=F and Y²=Cl, or Y¹=Cl and Y²=F.

$Z^2$ and $Z^{2'}$ in the formulae XXX and XXXI preferably each, independently of one another, denote a single bond, furthermore a —C₂H₄— bridge.

If, in the formula XXXI, $Z^2$=—C₂H₄—, $Z^{2'}$ is preferably a single bond, or, if $Z^{2'}$=—C₂H₄—, $Z^2$ is preferably a single bond. In the compounds of the formulae XXX and XXXI, (O)C$_v$H$_{2v+1}$ preferably denotes OC$_v$H$_{2v+1}$, furthermore C$_v$H$_{2v+1}$. In the compounds of the formulae XXXII and XXXIII, (O)C$_v$H$_{2v+1}$ preferably denotes C$_v$H$_{2v+1}$ and in the compounds of the formula XXXIII preferably denotes OC$_v$H$_{2v+1}$. In the compounds of the formulae XXXII and XXXIII, Y¹ and Y² preferably each denote F.

The medium optionally comprises one or more compounds of the following pyrimidine or pyridine compounds of the formulae

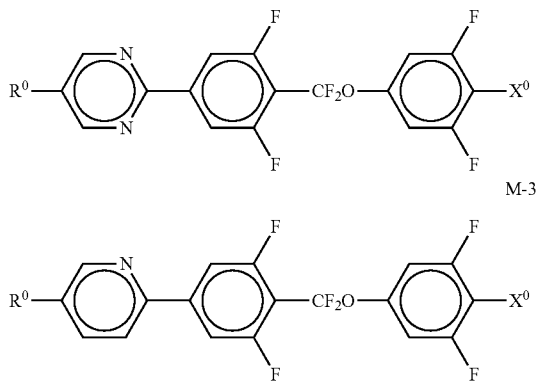

in which R⁰ and X⁰ have the meanings indicated above. R⁰ preferably denotes alkyl having 1 to 6 C atoms. X⁰ preferably denotes F. The medium according to the invention particularly preferably comprises one or more compounds of the formula M-1, in which X⁰ preferably denotes F. The compound(s) of the formulae M-1 to M-3 is (are) preferably employed in the mixtures according to the invention in amounts of 1-20% by weight, particularly preferably 1-15% by weight.

Further preferred embodiments are indicated below:

The mixtures according to the invention preferably comprise the compound of the formula I, in which A¹ preferably denotes

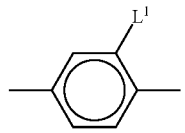

where L¹=F and R¹=R¹*=alkoxy;

Besides one or more compounds of the formula I, the medium comprises further compounds selected from the group of the compounds of the formulae II, III, IX-XIII, XVII and XVIII;

The proportion of compounds of the formulae II, III, IX-XIII, XVII and XVIII in the mixture as a whole is 40 to 99% by weight;

The medium preferably comprises 3-50% by weight, particularly preferably 5-40% by weight, especially preferably 8-30% by weight, of one, two, three or more compounds of the formulae II and/or III;

The medium preferably comprises 3-60% by weight, particularly preferably 5-50% by weight, especially preferably 10-40% by weight, of compounds of the formulae IX-XIII;

The medium preferably comprises 1-30% by weight, particularly preferably 5-30% by weight, of compounds of the formula XVII;

The medium preferably comprises 3-50% by weight, particularly preferably 5-40% by weight, of compounds of the formula XVIII;

The medium preferably comprises at least two compounds of the formulae

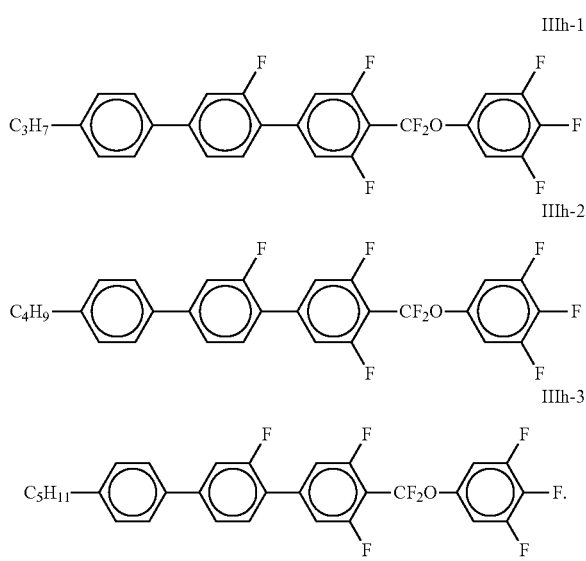

The medium preferably comprises at least two compounds of the formulae

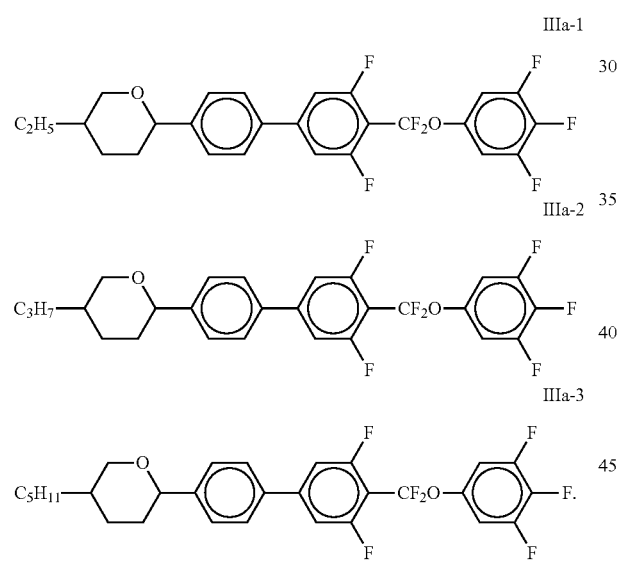

The medium comprises at least one compound of the formula I and at least one compound of the formula IIIh-2;

The medium preferably comprises 3% by weight, particularly preferably ≥5% by weight, in particular 3-60% by weight, of compounds of the formula IXb, in particular the compound of the formula IXb-1,

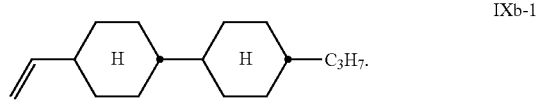

The medium preferably comprises at least one compound of the formula IXb-1 and preferably at least one compound of the formula XIII-d.

The medium preferably comprises at least one compound of the formula PUQU-n-F.

The medium comprises at least one compound of the formula APUQU-n-F.

The medium comprises at least one compound of the formula CPGP-n-m.

The medium comprises at least one compound of the formula PGP-n-m, preferably two or three compounds.

The medium comprises at least one compound of the formula CCP-3-OT having the structure

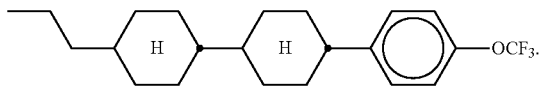

The medium comprises at least one compound of the formula CCP-V-1 having the structure

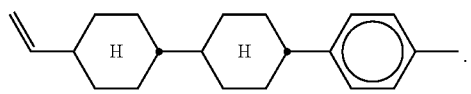

The medium comprises at least one compound of the formula PGP-2-2V having the structure

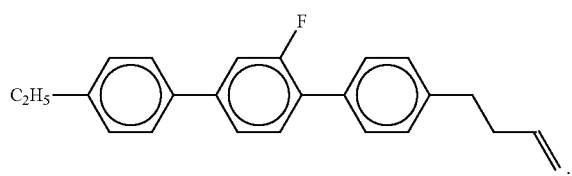

It has been found that ≥2% by weight of one or more compounds of the formula I mixed with conventional liquid-crystal materials, but in particular with one or more compounds of the formulae II to XXVIII, results in a significant increase in the light stability and in high birefringence values, with broad nematic phases with low smectic-nematic transition temperatures being observed at the same time, improving the shelf life. At the same time, the mixtures exhibit very low threshold voltages, very good values for the VHR on exposure to UV, and very high clearing points.

The term "alkyl" or "alkyl*" in this application encompasses straight-chain and branched alkyl groups having 1-6 carbon atoms, in particular the straight-chain groups methyl, ethyl, propyl, butyl, pentyl and hexyl. Groups having 2-5 carbon atoms are generally preferred.

The term "alkenyl" or "alkenyl*" encompasses straight-chain and branched alkenyl groups having 2-6 carbon atoms, in particular the straight-chain groups. Preferred alkenyl groups are $C_2$-$C_7$-1E-alkenyl, $C_4$-$C_6$-3E-alkenyl, in particular $C_2$-$C_6$-1E-alkenyl. Examples of particularly preferred alkenyl groups are vinyl, 1E-propenyl, 1E-butenyl, 1E-pentenyl, 1E-hexenyl, 3-butenyl, 3E-pentenyl, 3E-hexenyl, 4-pentenyl, 4Z-hexenyl, 4E-hexenyl and 5-hexenyl. Groups having up to 5 carbon atoms are generally preferred, in particular $CH_2=CH$, $CH_3CH=CH$, $CH_3CH_2CH_2CH_2=CH$ or $CH_3$ $CH_2CH_2=CH$.

The term "fluoroalkyl" preferably encompasses straight-chain groups having a terminal fluorine, i.e. fluoromethyl, 2-fluoroethyl, 3-fluoropropyl, 4-fluorobutyl, 5-fluoropentyl, 6-fluorohexyl and 7-fluoroheptyl. However, other positions of the fluorine are not excluded.

The term "oxaalkyl" or "alkoxy" preferably encompasses straight-chain radicals of the formula $C_nH_{2n+1}$—O—$(CH_2)_m$, in which n and m each, independently of one another, denote 1 to 6. m may also denote 0. Preferably, n=1 and m=1-6 or m=0 and n=1-3.

Through a suitable choice of the meanings of R° and X°, the addressing times, the threshold voltage, the steepness of the transmission characteristic lines, etc., can be modified in the desired manner. For example, 1E-alkenyl radicals, 3E-alkenyl radicals, 2E-alkenyloxy radicals and the like generally result in shorter addressing times, improved nematic tendencies and a higher ratio between the elastic constants $k_{33}$ (bend) and $k_{11}$ (splay) compared with alkyl and alkoxy radicals. 4-Alkenyl radicals, 3-alkenyl radicals and the like generally give lower threshold voltages and lower values of $k_{33}/k_{11}$ compared with alkyl and alkoxy radicals. The mixtures according to the invention are distinguished, in particular, by high Δn values and thus have significantly faster response times than the mixtures from the prior art.

The optimum mixing ratio of the compounds of the above-mentioned formulae depends substantially on the desired properties, on the choice of the components of the above-mentioned formulae and on the choice of any further components that may be present.

Suitable mixing ratios within the range indicated above can easily be determined from case to case.

The total amount of compounds of the above-mentioned formulae in the mixtures according to the invention is not crucial. The mixtures can therefore comprise one or more further components for the purposes of optimisation of various properties. However, the observed effect on the desired improvement in the properties of the mixture is generally greater, the higher the total concentration of compounds of the above-mentioned formulae.

A favourable synergistic action of compounds of the formulae II to XXVIII with one or more compounds of the formula I results in particularly advantageous properties. For example, mixtures comprising one or more compounds of the formulae I, XVa and/or XVIa are distinguished by their low threshold voltage.

The individual compounds of the above-mentioned formulae and the sub-formulae thereof which can be used in the media according to the invention are either known or can be prepared analogously to the known compounds.

The invention also relates to electro-optical displays, such as, for example, STN or MLC displays, having two plane-parallel outer plates, which, together with a frame, form a cell, integrated non-linear elements for switching individual pixels on the outer plates, and a nematic liquid-crystal mixture having positive dielectric anisotropy and high specific resistance located in the cell, which contain media of this type, and to the use of these media for electro-optical purposes.

The liquid-crystal mixtures according to the invention enable a significant broadening of the available parameter latitude. The achievable combinations of clearing point, viscosity at low temperature, thermal and UV stability and high optical anisotropy are far superior to previous materials from the prior art.

The mixtures according to the invention are particularly suitable for mobile applications and TFT applications, such as, for example, mobile telephones and PDAs. Furthermore, the mixtures according to the invention can be used in FFS, VA-IPS, OCB and IPS displays.

The liquid-crystal mixtures according to the invention, while retaining the nematic phase down to −20° C. and preferably down to −30° C., particularly preferably down to −40° C., and the clearing point ≥70° C., preferably ≥75° C., at the same time allow rotational viscosities $\gamma_1$ of ≤110 mPa·s, particularly preferably ≤100 mPa·s, to be achieved, enabling excellent MLC displays having fast response times to be achieved. The rotational viscosities are determined at 20° C.

The liquid-crystal mixtures according to the invention have, in particular, high values for $\varepsilon_\perp$ at 20° C., which are preferably ≥+2.5, further preferably ≥+3, particularly preferably ≥+3.5.

The dielectric anisotropy Δε of the liquid-crystal mixtures according to the invention at 20° C. is preferably ≥+1.5, further preferably ≥+3, particularly preferably ≥+5, especially preferably ≥8.

In addition, the mixtures are characterised by low operating voltages. The threshold voltage of the liquid-crystal mixtures according to the invention is preferably ≤2.0 V. The birefringence Δn of the liquid-crystal mixtures according to the invention at 20° C. is preferably ≥0.09, particularly preferably ≥0.10.

The nematic phase range of the liquid-crystal mixtures according to the invention preferably has a width of at least 90°, in particular at least 100°. This range preferably extends at least from −25° to +70° C.

It goes without saying that, through a suitable choice of the components of the mixtures according to the invention, it is also possible for higher clearing points (for example above 100° C.) to be achieved at higher threshold voltages or lower clearing points to be achieved at lower threshold voltages with retention of the other advantageous properties. At viscosities correspondingly increased only slightly, it is likewise possible to obtain mixtures having a higher Δε and thus low thresholds. The MLC displays according to the invention preferably operate at the first Gooch and Tarry transmission minimum [C. H. Gooch and H. A. Tarry, Electron. Lett. 10, 2-4, 1974; C. H. Gooch and H. A. Tarry, Appl. Phys., Vol. 8, 1575-1584, 1975], where, besides particularly favourable electro-optical properties, such as, for example, high steepness of the characteristic line and low angle dependence of the contrast (German patent 30 22 818), lower dielectric anisotropy is sufficient at the same threshold voltage as in an analogous display at the second minimum. This enables significantly higher specific resistance values to be achieved using the mixtures according to the invention at the first minimum than in the case of mixtures comprising cyano compounds. Through a suitable choice of the individual components and their proportions by weight, the person skilled in the art is able to set the birefringence necessary for a pre-specified layer thickness of the MLC display using simple routine methods.

The construction of the MLC display according to the invention from polarisers, electrode base plates and surface-treated electrodes corresponds to the usual design for displays of this type. The term usual design is broadly drawn here and also encompasses all derivatives and modifications of the MLC display, in particular including matrix display elements based on poly-Si TFTs or MIM.

A essential difference between the displays according to the invention and the hitherto conventional displays based on the twisted nematic cell consists, however, in the choice of the liquid-crystal parameters of the liquid-crystal layer.

The liquid-crystal mixtures which can be used in accordance with the invention are prepared in a manner conventional per se, for example by mixing one or more compounds of the formula I with one or more compounds of the formulae II-XXVIII or with further liquid-crystalline compounds and optionally with additives. In general, the desired amount of the components used in lesser amount is dissolved in the components making up the principal constituent, advantageously at elevated temperature. It is also possible to mix solutions of the components in an organic solvent, for example in acetone, chloroform or methanol, and to remove the solvent again, for example by distillation, after thorough mixing.

The dielectrics may also comprise further additives known to the person skilled in the art and described in the literature, such as, for example, UV stabilisers, such as Tinuvin®, e.g. Tinuvin® 770, from Ciba Chemicals, antioxidants, e.g. TEMPOL, microparticles, free-radical scavengers, nanoparticles, etc. For example, 0-15% of pleochroic dyes or chiral dopants can be added. Suitable stabilisers and dopants are mentioned below in Tables C and D.

Polymerisable compounds, so-called reactive mesogens (RMs), for example as disclosed in U.S. Pat. No. 6,861,107, may furthermore be added to the mixtures according to the invention in concentrations of preferably 0.12-5% by weight, particularly preferably 0.2-2% by weight, based on the mixture. These mixtures may optionally also comprise an initiator, as described, for example, in U.S. Pat. No. 6,781,665. The initiator, for example Irganox-1076 from Ciba, is preferably added to the mixture comprising polymerisable compounds in amounts of 0-1%. Mixtures of this type can be used for so-called polymer-stabilised VA modes (PS-VA) or PSA (polymer sustained VA), in which polymerisation of the reactive mesogens is intended to take place in the liquid-crystalline mixture. The prerequisite for this is that the liquid-crystal mixture does not itself comprise any polymerisable components.

In a preferred embodiment of the invention, the polymerisable compounds are selected from the compounds of the formula M

  M in which the individual radicals have the following meanings:

$R^a$ and $R^b$ each, independently of one another, denote P, P-Sp-, H, halogen, $SF_5$, $NO_2$, a carbon group or hydrocarbon group, where at least one of the radicals $R^a$ and $R^b$ preferably denotes or contains a group P or P-Sp-, P on each occurrence, identically or differently, denotes a polymerisable group, Sp on each occurrence, identically or differently, denotes a spacer group or a single bond, $A^1$ and $A^2$ each, independently of one another, denote an aromatic, heteroaromatic, alicyclic or heterocyclic group, preferably having 4 to 25 ring atoms, which may also contain fused rings, and which may also be mono- or polysubstituted by L, L denotes P-Sp-, H, OH, $CH_2OH$, halogen, $SF_5$, $NO_2$, a carbon group or hydrocarbon group, $Z^1$ on each occurrence, identically or differently, denotes —O—, —S—, —CO—, —CO—O—, —OCO—, —O—CO—O—, —OCH$_2$—, —CH$_2$O—, —SCH$_2$—, —CH$_2$S—, —CF$_2$O—, —OCF$_2$—, —CF$_2$S—, —SCF$_2$—, —(CH$_2$)$_{n1}$—, —CF$_2$CH$_2$—, —CH$_2$CF$_2$—, —(CF$_2$)$_{n1}$—, —CH=CH—, —CF=CF—, —C≡C—, —CH=CH—, —COO—, —OCO—CH=CH—, $CR^0R^{00}$ or a single bond, $R^0$ and $R^{00}$ each, independently of one another, denote H or alkyl having 1 to 12 C atoms, m denotes 0, 1, 2, 3 or 4, and n1 denotes 1, 2, 3 or 4.

Particularly preferred compounds of the formula M are those in which $R^a$ and $R^b$ each, independently of one another, denote P, P-Sp-, H, F, Cl, Br, I, —CN, —NO$_2$, —NCO, —NCS, —OCN, —SCN, SF$_5$ or straight-chain or branched alkyl having 1 to 25 C atoms, in which, in addition, one or more non-adjacent CH$_2$ groups may each be replaced, independently of one another, by —C(R$^0$)=C(R$^{00}$)—, —C≡C—, —N(R$^{00}$)—, —O—, —S—, —CO—, —CO—O—, —O—CO—, —O—CO—O— in such a way that O and/or S atoms are not linked directly to one another, and in which, in addition, one or more H atoms may be replaced by F, Cl, Br, I, CN, P or P-Sp-, where at least one of the radicals $R^a$ and $R^b$ denotes or contains a group P or P-Sp-, $A^1$ and $A^2$ each, independently of one another, denote 1,4-phenylene, naphthalene-1,4-diyl, naphthalene-2,6-diyl, phenanthrene-2,7-diyl, anthracene-2,7-diyl, fluorene-2,7-diyl, 2-oxo-2H-chromene-3,6-diyl, 2-oxo-2H-chromene-3,7-diyl, 4-oxo-4H-chromene-2,6-diyl, 4-oxo-4H-chromene-3,6-diyl, 4-oxo-4H-chromene-3,7-diyl (trivial name coumarine or flavone), where, in addition, one or more CH groups in these groups may be replaced by N, cyclohexane-1,4-diyl, in which, in addition, one or more non-adjacent CH$_2$ groups may be replaced by O and/or S, 1,4-cyclohexenylene, bicyclo[1.1.1]pentane-1,3-diyl, bicyclo[2.2.2]octane-1,4-diyl, spiro[3.3]heptane-2,6-diyl, piperidine-1,4-diyl, decahydronaphthalene-2,6-diyl, 1,2,3,4-tetra-hydronaphthalene-2,6-diyl, indane-2,5-diyl or octahydro-4,7-methanoindane-2,5-diyl, where all these groups may be unsubstituted or mono- or polysubstituted by L, L denotes P, P-Sp-, OH, CH$_2$OH, F, Cl, Br, I, —CN, —NO$_2$, —NCO, —NCS, —OCN, —SCN, —C(=O)N(R$^x$)$_2$, —C(=O)Y$^1$, —C(=O)R$^x$, —N(R$^x$)$_2$, optionally substituted silyl, optionally substituted aryl having 6 to 20 C atoms, or straight-chain or branched alkyl, alkoxy, alkylcarbonyl, alkoxycarbonyl, alkylcarbonyloxy or alkoxycarbonyloxy having 1 to 25 C atoms, in which, in addition, one or more H atoms may be replaced by F, Cl, P or P-Sp-, P denotes a polymerisable group, $Y^1$ denotes halogen, $R^x$ denotes P, P-Sp-, H, halogen, straight-chain, branched or cyclic alkyl having 1 to 25 C atoms, in which, in addition, one or more non-adjacent CH$_2$ groups may be replaced by —O—, —S—, —CO—, —CO—O—, —O—CO—, —O—CO—O— in such a way that O and/or S atoms are not linked directly to one another, and in which, in addition, one or more H atoms may be replaced by F, Cl, P or P-Sp-, an optionally substituted aryl or aryloxy group having 6 to 40 C atoms, or an optionally substituted heteroaryl or heteroaryloxy group having 2 to 40 C atoms.

Further preferred compounds of the formula M are those selected from one or more of the following sub-groups:

m is 1, 2 or 3, m is 1 or 2, $R^a$ and $R^b$ denote identical or different groups P-Sp-, $R^a$ and $R^b$ denote identical or different groups P-Sp-, in which one or more groups Sp denote a single bond, m is 2 or 3 and $R^a$ and $R^b$ denote identical groups P-Sp-, one of the radicals $R^a$ and $R^b$ denotes P-Sp- and the other denotes an unpolymerisable group, preferably straight-chain or branched alkyl having 1 to 25 C atoms, in which, in addition, one or more non-adjacent CH$_2$ groups may each be replaced, independently of one another, by —C(R$^{00}$)=C(R$^{000}$)—, —C≡C—, —N(R$^{00}$)—, —O—, —S—, —CO—, —CO—O—, —O—CO— or —O—CO—O— in such a way that O and/or S atoms are not linked directly to one another, and in which, in addition, one or more H atoms may be replaced by F, Cl, Br, I or CN, one or more groups Sp denote a single bond, one or more groups Sp denote —(CH$_2$)$_{p1}$—, —(CH$_2$)$_{p1}$—O—, —(CH$_2$)$_{p1}$—OCO— or —(CH$_2$)$_{p1}$—OCOO—, in which p1 denotes an integer from 1 to 12 and r1 denotes an integer from 1 to 8, L does not denote and/or contain a polymerisable group, A$^1$ and A$^2$ denote, independently of one another, 1,4-phenylene or naphthalene-2,6-diyl, where, in addition, one or more CH groups in these groups may be replaced by N, and which may also be mono- or polyfluorinated, Z$^1$ is selected from the group consisting of —O—, —CO—O—, —OCO—, —OCH$_2$—, —CH$_2$O—, —CF$_2$O—, —OCF$_2$—, —CH$_2$CH$_2$—, —CH=CH—, —CF=CF—, —CH=CF—, —CF=CH—, —C≡C— and a single bond, L is an unpolymerisable group, preferably selected from the group consisting of F, Cl, —CN, straight-chain and branched alkyl having 1 to 25 C atoms, in which, in addition, one or more non-adjacent CH$_2$ groups may each be replaced, independently of one another, by —C(R$^{00}$)=C(R$^{000}$)—, —C≡C—, —N(R$^{00}$)—, —O—, —S—, —CO—, —CO—O—, —O—CO— or —O—CO—O— in such a way that O and/or S atoms are not linked directly to one another, and in which, in addition, one or more H atoms may be replaced by F, Cl, Br, I or CN.

Suitable and preferred comonomers for the preparation of mixtures according to the invention for PS-VA, PS-IPS and PS-FFS applications are selected, for example, from the following formulae:

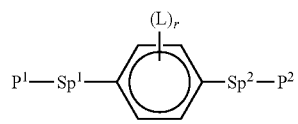

M1

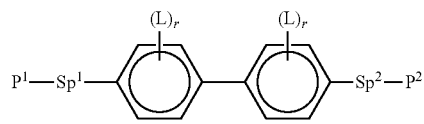

M2

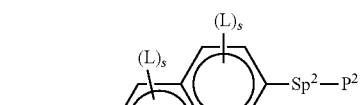

M3

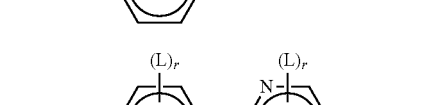

M4

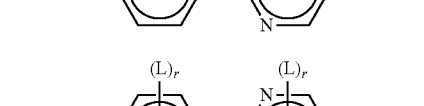

M5

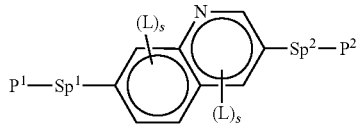

M6

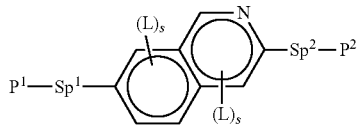

M7

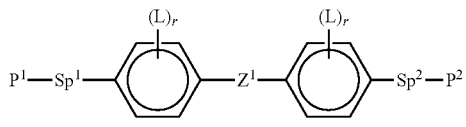

M8

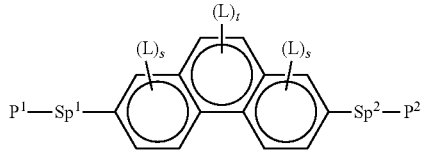

M9

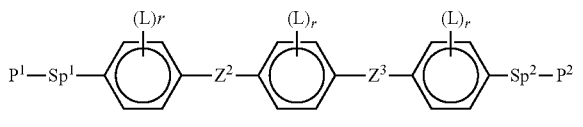

M10

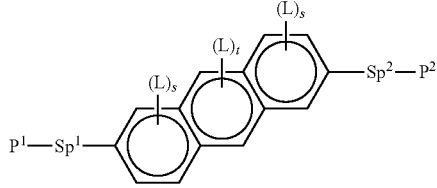

M11

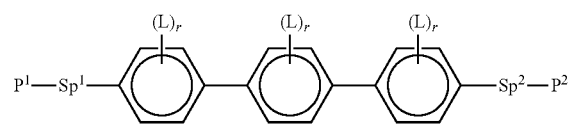

M12

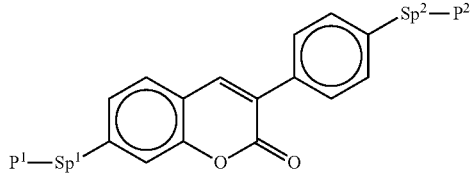

M13

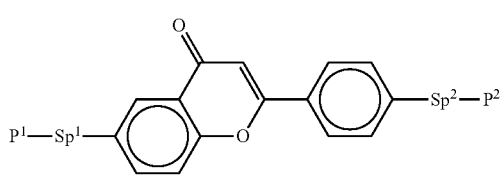

M14

-continued

M15, M16, M17, M18, M19, M20, M21, M22, M23, M24, M25, M26, M27, M28, M29, M30, M31, M32

-continued

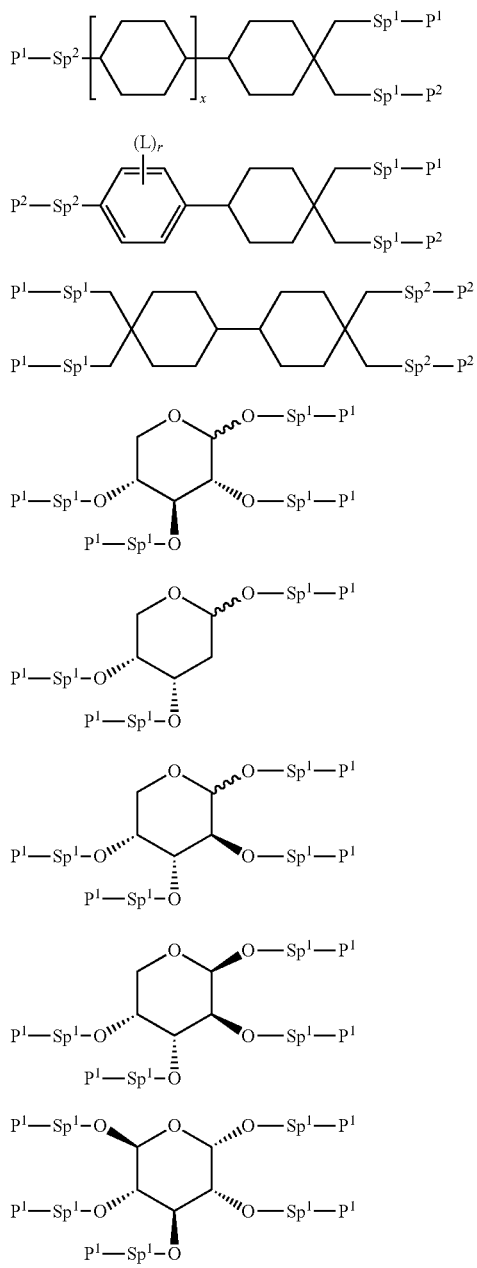

in which the individual radicals have the following meanings:

P¹, P² and P³ each, independently of one another, denote a polymerisable group, preferably having one of the meanings indicated above and below for P, particularly preferably an acrylate, methacrylate, fluoroacrylate, oxetane, vinyloxy or epoxy group, Sp¹, Sp² and Sp² each, independently of one another, denote a single bond or a spacer group, preferably having one of the meanings indicated above and below for $Sp^a$, and particularly preferably —$(CH_2)_{p1}$—, —$(CH_2)_{p1}$—O—, —$(CH_2)_{p1}$—CO—O— or —$(CH_2)_{p1}$—O—CO—O—, in which p1 is an integer from 1 to 12, and where the linking of the last-mentioned groups to the adjacent ring takes place via the O atom, where, in addition, one or more of the radicals P¹-Sp¹-, P²-Sp²- and P³-Sp³- may denote a radical $R^{aa}$, with the proviso that at least one of the radicals P¹-Sp¹-, P²-Sp²- and P³-Sp³- present does not denote $R^{aa}$, $R^{aa}$ denotes H, F, Cl, CN or straight-chain or branched alkyl having 1 to 25 C atoms, in which, in addition, one or more non-adjacent $CH_2$ groups may each be replaced, independently of one another, by —C($R^0$)=C($R^{00}$)—, —C≡C—, —N($R^0$)—, —O—, —S—, —CO—, —CO—O—, —O—CO—, —O—CO—O— in such a way that O and/or S atoms are not linked directly to one another, and in which, in addition, one or more H atoms may be replaced by F, Cl, CN or P¹-Sp¹-, particularly preferably straight-chain or branched, optionally mono- or polyfluorinated alkyl, alkoxy, alkenyl, alkynyl, alkylcarbonyl, alkoxycarbonyl or alkylcarbonyloxy having 1 to 12 C atoms (where the alkenyl and alkynyl radicals have at least two C atoms and the branched radicals have at least three C atoms), $R^0$, $R^{00}$ each, independently of one another and on each occurrence identically or differently, denote H or alkyl having 1 to 12 C atoms, $R^y$ and $R^z$ each, independently of one another, denote H, F, $CH_3$ or $CF_3$, X¹, X² and X³ each, independently of one another, denote —CO—O—, —O—CO— or a single bond, Z¹ denotes —O—, —CO—, —C($R^yR^z$)— or —$CF_2CF_2$—, Z² and Z³ each, independently of one another, denote —CO—O—, —O—CO—, —$CH_2$O—, —O$CH_2$—, —$CF_2$O—, —O$CF_2$— or —$(CH_2)_n$—, where n is 2, 3 or 4, L on each occurrence, identically or differently, denotes F, Cl, CN, SCN, $SF_5$ or straight-chain or branched, optionally mono- or polyfluorinated alkyl, alkoxy, alkenyl, alkynyl, alkylcarbonyl, alkoxycarbonyl, alkylcarbonyloxy or alkoxycarbonyloxy having 1 to 12 C atoms, preferably F, L' and L" each, independently of one another, denote H, F or Cl, r denotes 0, 1, 2, 3 or 4, s denotes 0, 1, 2 or 3, t denotes 0, 1 or 2, and x denotes 0 or 1.

In the compounds of the formulae M1 to M34,

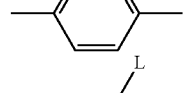 preferably denotes

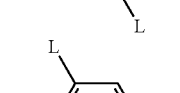 , 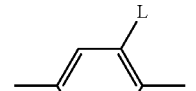 ,

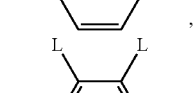 ,

-continued

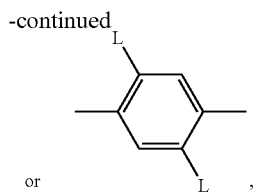

or in which L, identically or differently on each occurrence, has one of the above meanings and preferably denotes F, Cl, CN, $NO_2$, $CH_3$, $C_2H_5$, $C(CH_3)_3$, $CH(CH_3)_2$, $CH_2CH(CH_3)C_2H_5$, $OCH_3$, $OC_2H_5$, $COCH_3$, $COC_2H_5$, $COOCH_3$, $COOC_2H_5$, $CF_3$, $OCF_3$, $OCHF_2$, $OC_2F_5$ or P-Sp-, particularly preferably F, Cl, CN, $CH_3$, $C_2H_5$, $OCH_3$, $COCH_3$, $OCF_3$ or P-Sp-, very particularly preferably F, Cl, $CH_3$, $OCH_3$, $COCH_3$ or $OCF_3$, in particular F or $CH_3$.

The liquid-crystalline media in accordance with the present application preferably comprise in total 0.01 to 10%, preferably 0.2 to 4.0%, particularly preferably 0.2 to 2.0%, of polymerisable compounds.

Particular preference is given to the polymerisable compounds of the formula M, and very particular preference is given to the polymerisable compounds selected from Table F.

The present invention also relates to the use of the mixtures according to the invention in electro-optical displays and to the use of the mixtures according to the invention in shutter glasses, in particular for 3D applications, and in TN, PS-TN, STN, TN-TFT, OCB, IPS, PS-IPS, FFS, PS-FFS and PS-VA-IPS displays.

For the present invention, "≤" means less than or equal to, preferably less than, and "≥" means greater than or equal to, preferably greater than.

For the present invention,

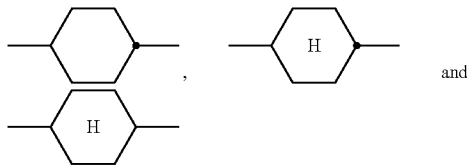

and denote trans-1,4-cyclohexylene, and

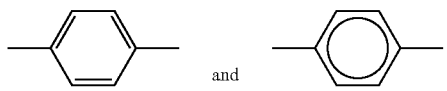

and denote 1,4-phenylene.

For the present invention, the term "dielectrically positive compounds" means compounds having a Δε of >1.5, the term "dielectrically neutral compounds" means those where −1.5≤Δε≤1.5 and the term "dielectrically negative compounds" means those where Δε<−1.5. The dielectric anisotropy of the compounds is determined here by dissolving 10% of the compounds in a liquid-crystalline host and determining the capacitance of the resultant mixture in each case in at least one test cell having a cell thickness of 20 μm with homeotropic and with homogeneous surface alignment at 1 kHz. The measurement voltage is typically 0.5 V to 1.0 V, but is always lower than the capacitive threshold of the respective liquid-crystal mixture investigated.

The host mixture used for dielectrically positive and dielectrically neutral compounds is ZLI-4792 and that used for dielectrically negative compounds is ZLI-2857, both from Merck KGaA, Germany. The values for the respective compounds to be investigated are obtained from the change in the dielectric constant of the host mixture after addition of the compound to be investigated and extrapolation to 100% of the compound employed. The compound to be investigated is dissolved in the host mixture in an amount of 10%. If the solubility of the substance is too low for this purpose, the concentration is halved in steps until the investigation can be carried out at the desired temperature.

All variants of the invention described here can be combined with one another so long as the respective embodiments are not mutually exclusive. In particular, it is an obvious operation, on the basis of the teaching of this specification, in the course of of routine optimisation, specifically to combine various variants described here in order to obtain a specific particularly preferred embodiment.

The parameter ranges indicated in this application, unless indicated otherwise, encompass all rational and integer numerical values including the indicated limit values of the parameter range and error limits thereof. The upper and lower limit values indicated for respective ranges and properties in turn result, in combination with one another, in additional preferred ranges.

Throughout the description and the claims of this application, the words "include" and "comprise" and variations of these words, such as, for example, "including" and "includes", are to be interpreted as "including, but not restricted to" and do not exclude other components. The word "include" also encompasses the term "consisting of", but is not restricted thereto.

For the present application and in the examples below, the structures of the liquid-crystal compounds are indicated by acronyms, the transformation into chemical formulae taking place in accordance with Tables A to C below. All radicals $C_nH_{2n+1}$, $C_mH_{2m+1}$ $C_mH_{2m+1}$ $C_lH_{2l+1}$ or $C_nH_{2n}$, $C_mH_{2m}$ and $C_lH_{2l}$ are straight-chain alkyl radicals or alkylene radicals having n, m or l C atoms respectively. In Table A the ring elements of the nuclei of the compound are coded, in Table B the bridging members are listed and in Table C the meanings of the symbols for the left- and right-hand end groups of the molecules are listed. The acronyms are composed of the codes for the ring elements with optional linking groups, followed by a first hyphen and the codes for the left-hand end group, and a second hyphen and the codes for the right-hand end group.

TABLE A

Ring elements

C 

TABLE A-continued
| | | | |
|---|---|---|---|
| D | 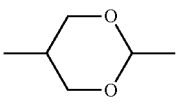 | DI | 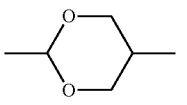 |
| A | 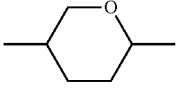 | AI | 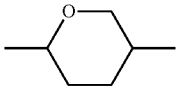 |
| P |  | | |
| G | 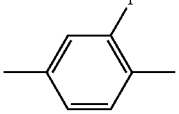 | GI | 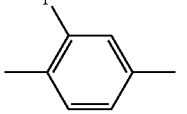 |
| U | 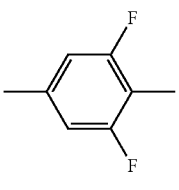 | UI | 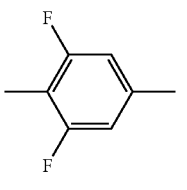 |
| Y | 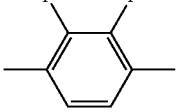 | | |
| P(F, Cl) | 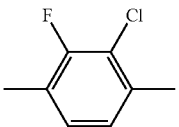 | P(Cl, F) | 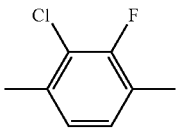 |
| N | 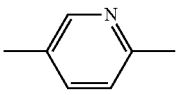 | NI | 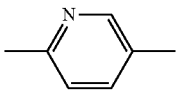 |
| M | 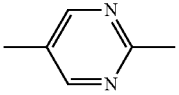 | MI | 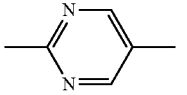 |
| np | 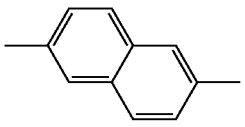 | | |
| n3f | 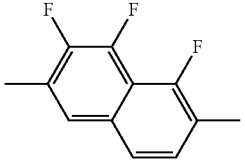 | n3fI | 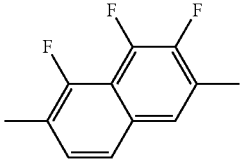 |
| th | 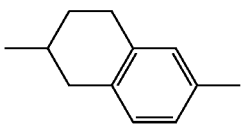 | thI | 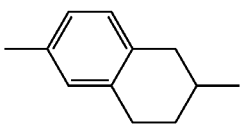 |

TABLE A-continued

| Ring elements | | | |
|---|---|---|---|
| tH2f | 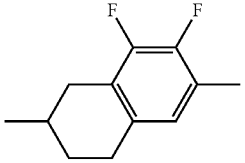 | tH2fI | 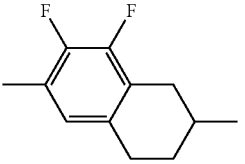 |
| o2f | 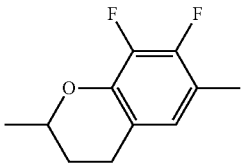 | o2fI | 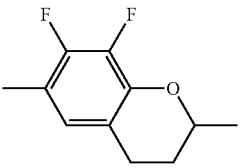 |
| dh | 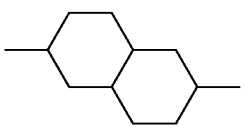 | | |
| K | 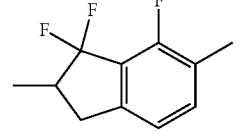 | KI | 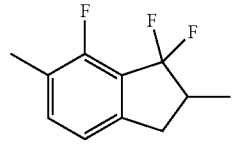 |
| L |  | LI |  |
| F | 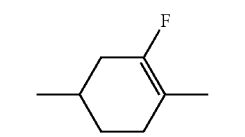 | FI | 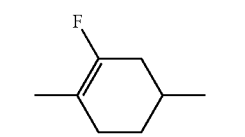 |

TABLE B

| Bridging members | |
|---|---|
| E | —$CH_2$—$CH_2$— |
| V | —CH=CH— |
| T | —C≡C— |
| W | —$CF_2$—$CF_2$— |
| B | —CF=CF— |

TABLE B-continued

| Bridging members | | | |
|---|---|---|---|
| Z | —CO—O— | ZI | —O—CO— |
| X | —CF=CH— | XI | —CH=CF— |
| O | —$CH_2$—O— | OI | —O—$CH_2$— |
| Q | —$CF_2$—O— | QI | —O—$CF_2$— |

TABLE C

| End groups | | | |
|---|---|---|---|
| On the left individually or in combination | | On the right individually or in combination | |
| -n- | $C_nH_{2n+1}$— | -n | —$C_nH_{2n+1}$ |
| -nO- | $C_nH_{2n+1}$—O— | -nO | —O—$C_nH_{2n+1}$ |
| -V- | $CH_2$=CH— | -V | —CH=$CH_2$ |
| -nV- | $C_nH_{2n+1}$—CH=CH— | -nV | —$C_nH_{2n}$—CH=$CH_2$ |
| -Vn- | $CH_2$=CH—$C_nH_{2n}$— | -Vn | —CH=CH—$C_nH_{2n+1}$ |
| -nVm- | $C_nH_{2n+1}$—CH=CH—$C_mH_{2m}$— | -nVm | —$C_nH_{2n}$—CH=CH—$C_mH_{2m+1}$ |
| -N- | N≡C— | -N | —C≡N |
| -S- | S=C=N— | -S | —N=C=S |
| -F- | F— | -F | —F |
| -CL- | Cl— | -CL | —Cl |
| -M- | $CFH_2$— | -M | —$CFH_2$ |
| -D- | $CF_2H$— | -D | —$CF_2H$ |
| -T- | $CF_3$— | -T | —$CF_3$ |
| -MO- | $CFH_2O$— | -OM | —$OCFH_2$ |
| -DO- | $CF_2HO$— | -OD | —$OCF_2H$ |

TABLE C-continued

| End groups | | | |
|---|---|---|---|
| -TO- | CF$_3$O— | -OT | —OCF$_3$ |
| -A- | H—C≡C— | -A | —C≡C—H |
| -nA- | C$_n$H$_{2n+1}$—C≡C— | -An | —C≡C—C$_n$H$_{2n+1}$ |
| -NA- | N≡C—C≡C— | -AN | —C≡C—C≡N |

| On the left only in combination | | On the right only in combination | |
|---|---|---|---|
| -...n...- | —C$_n$H$_{2n}$— | -...n... | —C$_n$H$_{2n}$— |
| -...M...- | —CFH— | -...M... | —CFH— |
| -...D...- | —CF$_2$— | -...D... | —CF$_2$— |
| -...V...- | —CH=CH— | -...V... | —CH=CH— |
| -...Z...- | —CO—O— | -...Z... | —CO—O— |
| -...ZI...- | —O—CO— | -...ZI... | —O—CO— |
| -...K...- | —CO— | -...K... | —CO— |
| -...W...- | —CF=CF— | -...W... | —CF=CF— | in which n and m are each integers, and the three dots "..." are place-holders for other abbreviations from this table.

in which n and m are each integers, and the three dots "..." are place-holders for other abbreviations from this table.

TABLE D

Table D indicates possible dopants which are generally added to the mixtures according to the invention. The mixtures preferably comprise 0-10% by weight, in particular 0.01-5% by weight and particularly preferably 0.01-3% by weight of dopants.

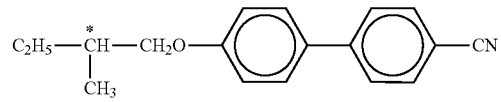

C 15

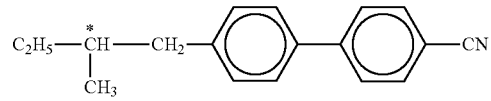

CB 15

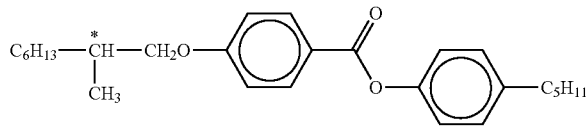

CM 21

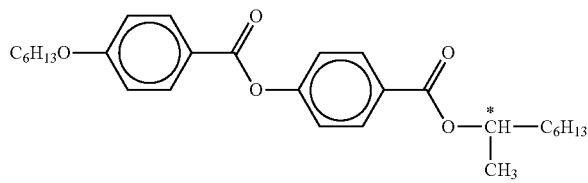

R/S-811

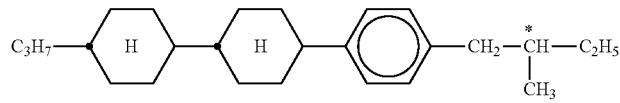

CM 44

TABLE D-continued
Table D indicates possible dopants which are generally added to the mixtures according to the invention. The mixtures preferably comprise 0-10% by weight, in particular 0.01-5% by weight and particularly preferably 0.01-3% by weight of dopants.
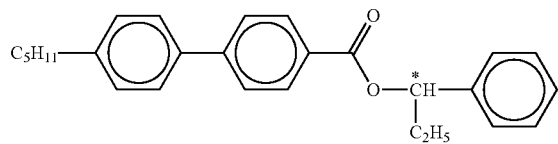
CM 45
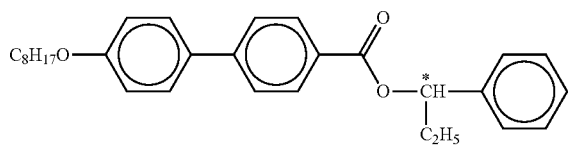
CM 47
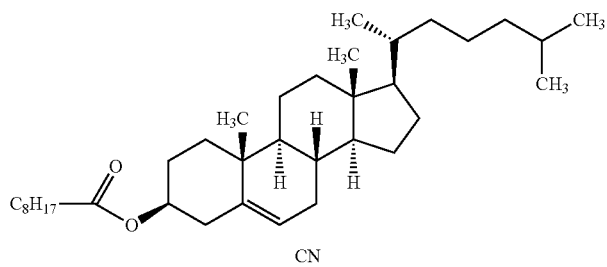
CN
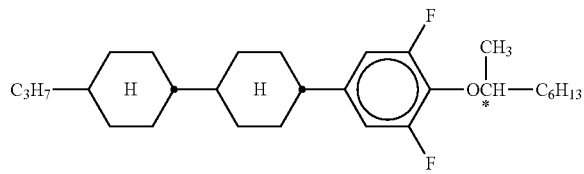
R/S-2011
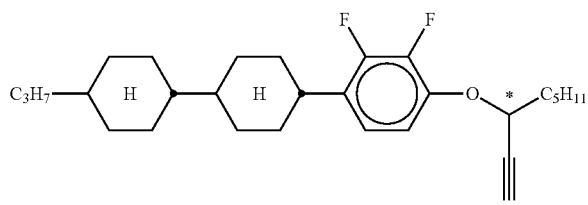
R/S-3011
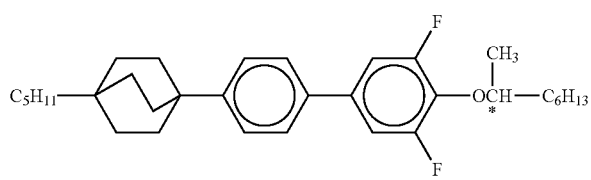
R/S-4011

TABLE D-continued

Table D indicates possible dopants which are generally added to the mixtures according to the invention. The mixtures preferably comprise 0-10% by weight, in particular 0.01-5% by weight and particularly preferably 0.01-3% by weight of dopants.

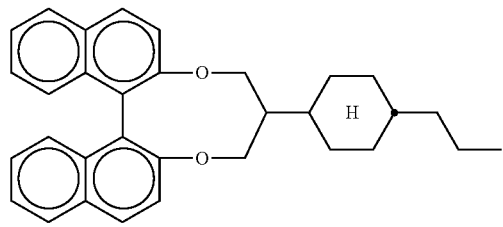

R/S-5011

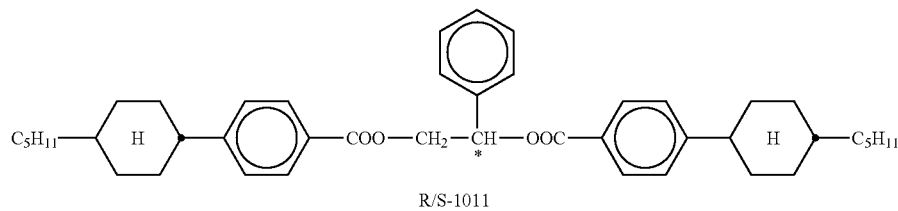

R/S-1011

TABLE E

Stabilisers, which can be added, for example, to the mixtures according to the invention in amounts of 0-10% by weight, are mentioned below.
(n = 1-12)

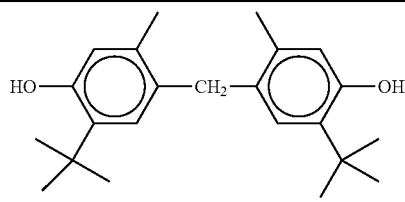

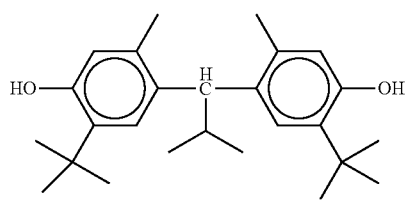

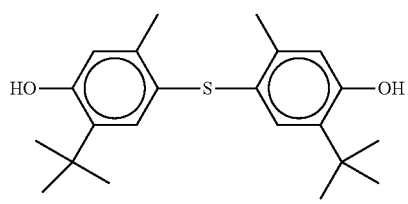

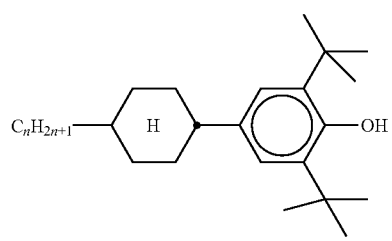

TABLE E-continued
Stabilisers, which can be added, for example,
to the mixtures according to the invention in amounts of 0-10% by weight, are mentioned below.
(n = 1-12)
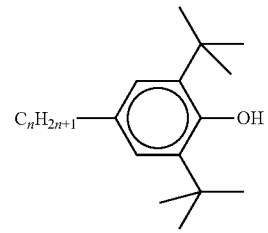
n = 1, 2, 3, 4, 5, 6 or 7
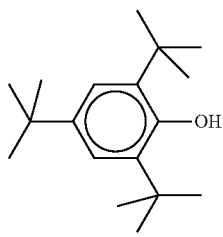
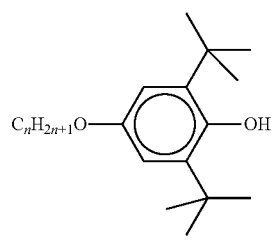
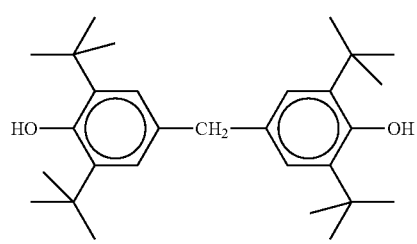
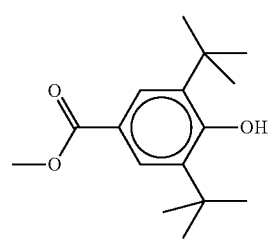
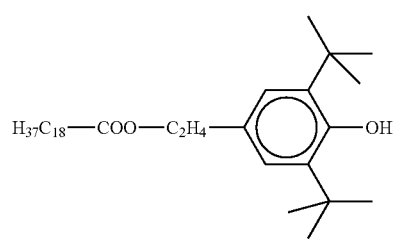

TABLE E-continued
Stabilisers, which can be added, for example,
to the mixtures according to the invention in amounts of 0-10% by weight, are mentioned below.
(n = 1-12)
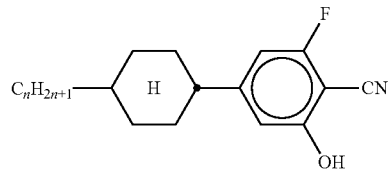
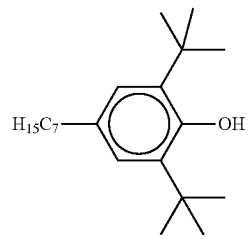
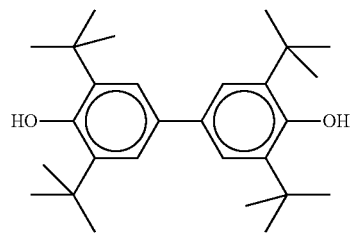
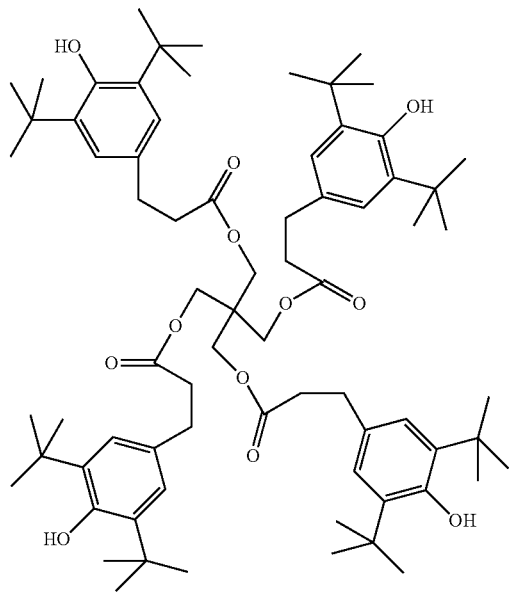 [SMILES: CC(C)(C)c1cc(CCC(=O)OCC(COC(=O)CCc2cc(C(C)(C)C)c(O)c(C(C)(C)C)c2)(COC(=O)CCc2cc(C(C)(C)C)c(O)c(C(C)(C)C)c2)COC(=O)CCc2cc(C(C)(C)C)c(O)c(C(C)(C)C)c2)cc(C(C)(C)C)c1O]
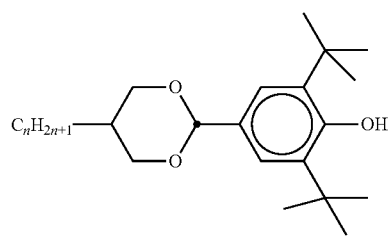
n = 1, 2, 3, 4, 5, 6 or 7

TABLE E-continued
Stabilisers, which can be added, for example,
to the mixtures according to the invention in amounts of 0-10% by weight, are mentioned below.
(n = 1-12)
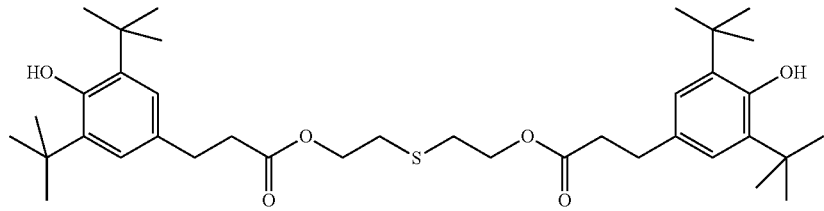 [SMILES: CC(C)(C)c1cc(CCC(=O)OCCSCCOC(=O)CCc2cc(C(C)(C)C)c(O)c(C(C)(C)C)c2)cc(C(C)(C)C)c1O]
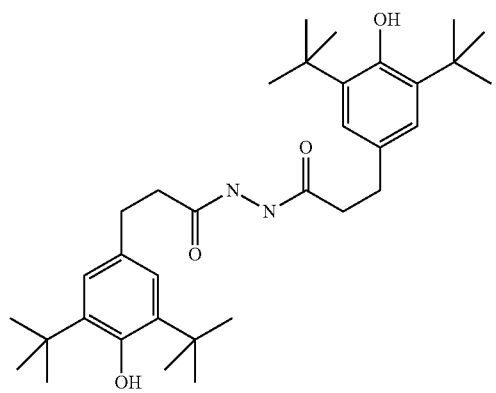 [SMILES: CC(C)(C)c1cc(CCC(=O)NNC(=O)CCc2cc(C(C)(C)C)c(O)c(C(C)(C)C)c2)cc(C(C)(C)C)c1O]
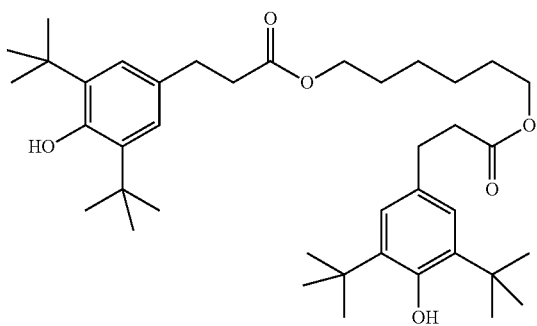 [SMILES: CC(C)(C)c1cc(CCC(=O)OCCCCCCOC(=O)CCc2cc(C(C)(C)C)c(O)c(C(C)(C)C)c2)cc(C(C)(C)C)c1O]
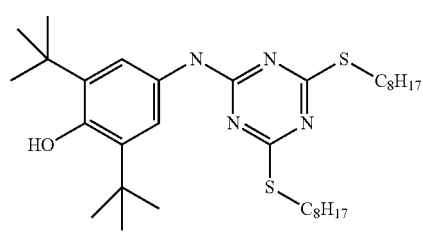

TABLE E-continued
Stabilisers, which can be added, for example,
to the mixtures according to the invention in amounts of 0-10% by weight, are mentioned below.
(n = 1-12)
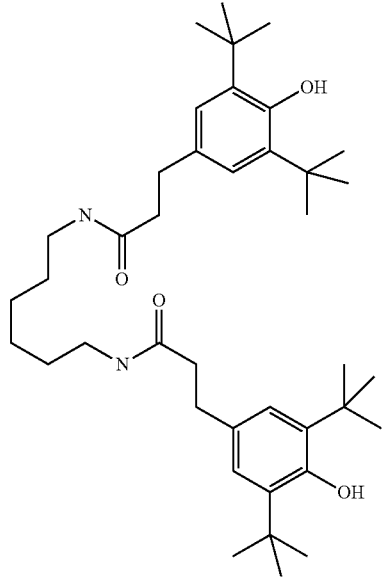 [SMILES: CC(C)(C)c1cc(CCC(=O)NCCCCCCNC(=O)CCc2cc(C(C)(C)C)c(O)c(C(C)(C)C)c2)cc(C(C)(C)C)c1O]
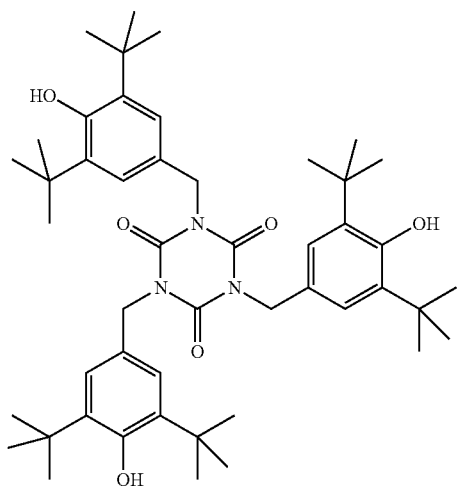 [SMILES: CC(C)(C)c1cc(Cn2c(=O)n(Cc3cc(C(C)(C)C)c(O)c(C(C)(C)C)c3)c(=O)n(Cc3cc(C(C)(C)C)c(O)c(C(C)(C)C)c3)c2=O)cc(C(C)(C)C)c1O]
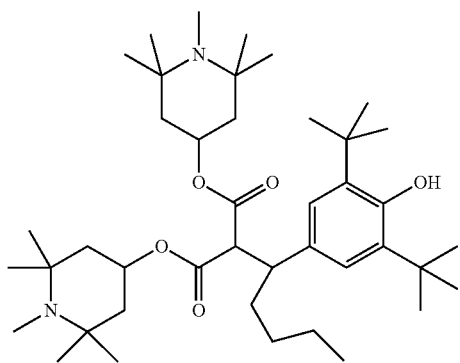 [SMILES: CCCCC(c1cc(C(C)(C)C)c(O)c(C(C)(C)C)c1)C(C(=O)OC1CC(C)(C)N(C)C(C)(C)C1)C(=O)OC1CC(C)(C)N(C)C(C)(C)C1]

TABLE E-continued
Stabilisers, which can be added, for example,
to the mixtures according to the invention in amounts of 0-10% by weight, are mentioned below.
(n = 1-12)
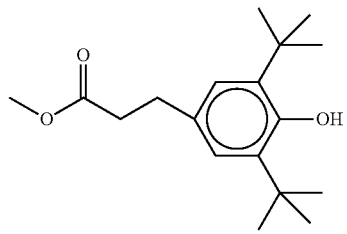
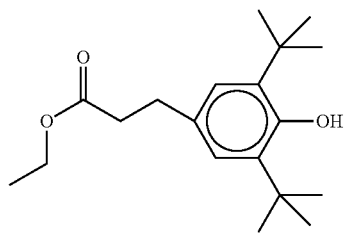
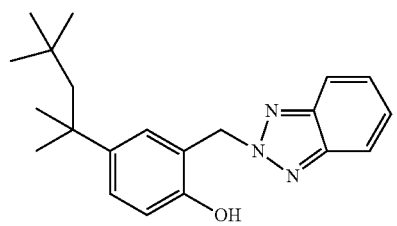 [SMILES: CC(C)(C)CC(C)(C)c1ccc(O)c(Cn2nc3ccccc3n2)c1]
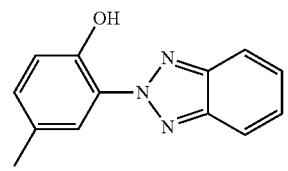 [SMILES: Cc1ccc(O)c(-n2nc3ccccc3n2)c1]
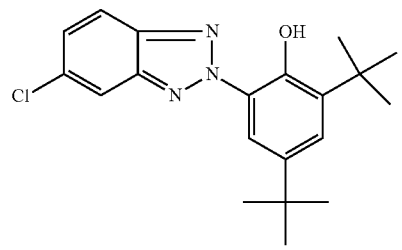 [SMILES: CC(C)(C)c1cc(-n2nc3ccc(Cl)cc3n2)c(O)c(C(C)(C)C)c1]
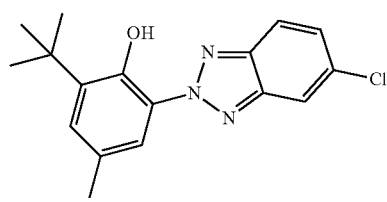 [SMILES: Cc1cc(-n2nc3ccc(Cl)cc3n2)c(O)c(C(C)(C)C)c1]

TABLE E-continued
Stabilisers, which can be added, for example,
to the mixtures according to the invention in amounts of 0-10% by weight, are mentioned below.
(n = 1-12)
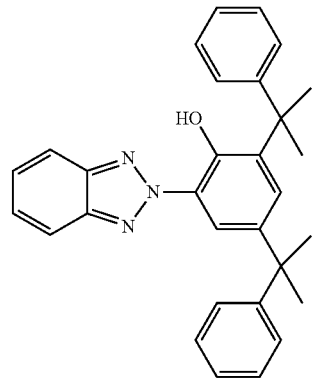 [SMILES: CC(C)(c1ccccc1)c1cc(-n2nc3ccccc3n2)c(O)c(C(C)(C)c2ccccc2)c1]
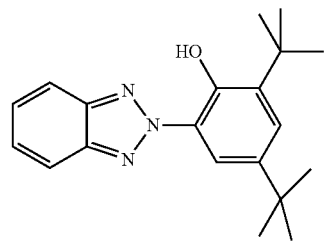 [SMILES: CC(C)(C)c1cc(-n2nc3ccccc3n2)c(O)c(C(C)(C)C)c1]
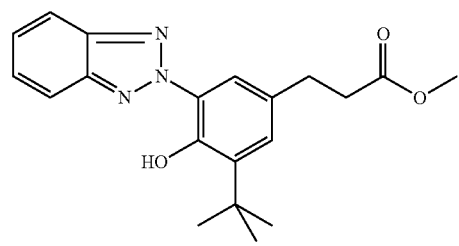 [SMILES: COC(=O)CCc1cc(-n2nc3ccccc3n2)c(O)c(C(C)(C)C)c1]
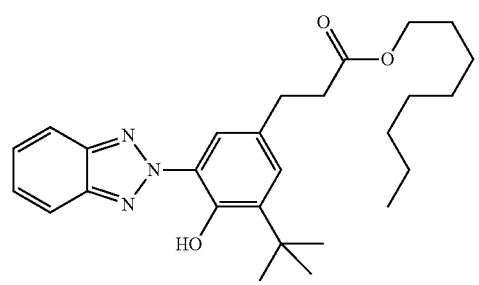 [SMILES: CCCCCCCCOC(=O)CCc1cc(-n2nc3ccccc3n2)c(O)c(C(C)(C)C)c1]

TABLE E-continued
Stabilisers, which can be added, for example,
to the mixtures according to the invention in amounts of 0-10% by weight, are mentioned below.
(n = 1-12)
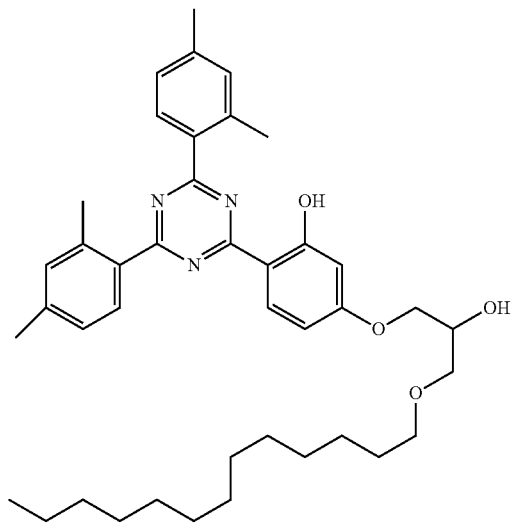 [SMILES: CCCCCCCCCCCCCOCC(O)COc1ccc(-c2nc(-c3ccc(C)cc3C)nc(-c3ccc(C)cc3C)n2)c(O)c1]
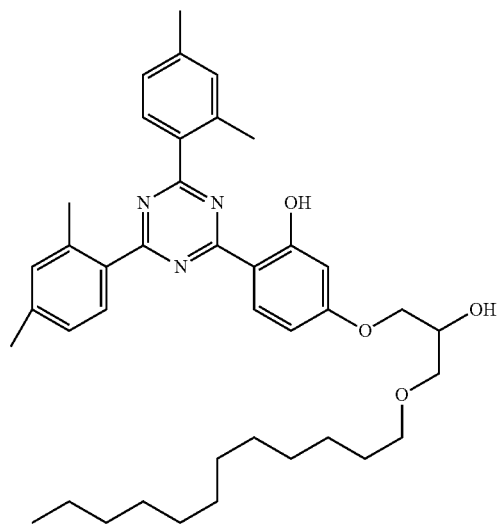 [SMILES: CCCCCCCCCCCCOCC(O)COc1ccc(-c2nc(-c3ccc(C)cc3C)nc(-c3ccc(C)cc3C)n2)c(O)c1]
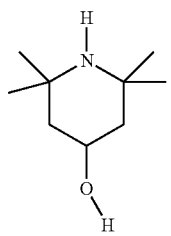
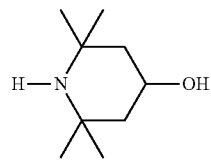

TABLE E-continued
Stabilisers, which can be added, for example,
to the mixtures according to the invention in amounts of 0-10% by weight, are mentioned below.
(n = 1-12)
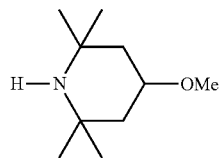
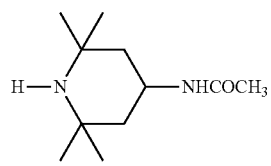
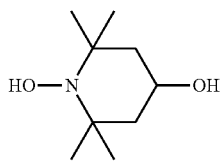
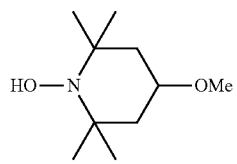
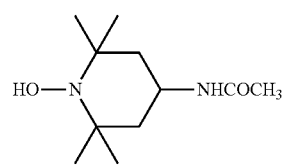
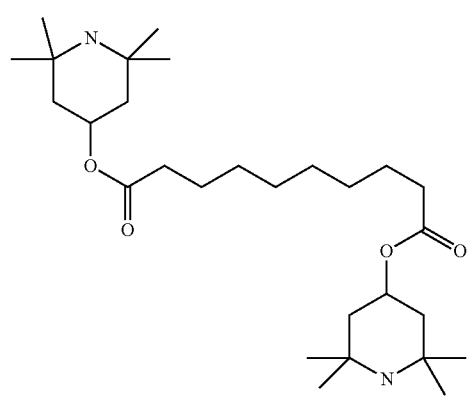

TABLE E-continued
Stabilisers, which can be added, for example,
to the mixtures according to the invention in amounts of 0-10% by weight, are mentioned below.
(n = 1-12)
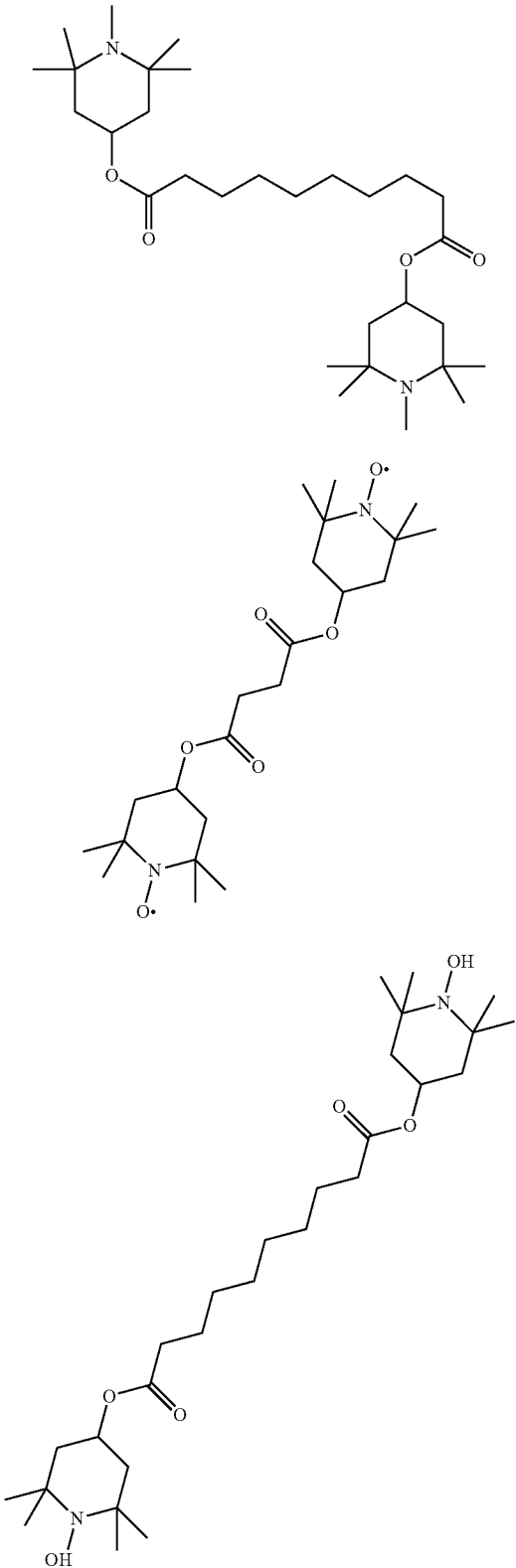

Suitable polymerisable compounds (reactive mesogens) for use in the mixtures according to the invention, preferably in PSA and PS-VA applications or PS-IPS/FFS applications, are mentioned below in Table E:

TABLE F

Table F shows example compounds which can preferably be used in the mixtures according to the invention as polymerisable compounds (reactive mesogenic compounds) for the preparation, for example, of PSV, PS-VA, PS-IPS or PS-FFS mixtures.

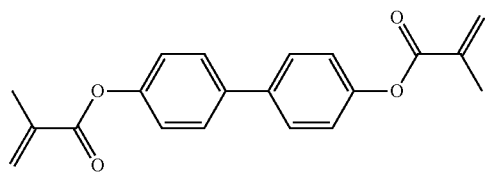 [SMILES: C=C(C)C(=O)Oc1ccc(-c2ccc(OC(=O)C(=C)C)cc2)cc1]

RM-1

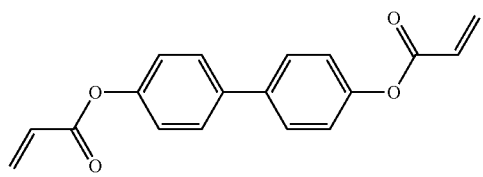 [SMILES: C=CC(=O)Oc1ccc(-c2ccc(OC(=O)C=C)cc2)cc1]

RM-2

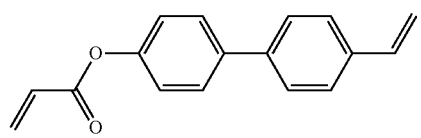 [SMILES: C=CC(=O)Oc1ccc(-c2ccc(C=C)cc2)cc1]

RM-3

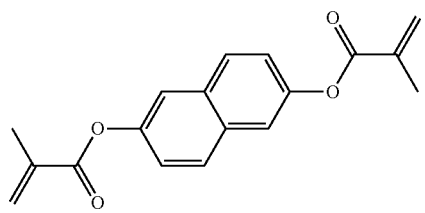 [SMILES: C=C(C)C(=O)Oc1ccc2cc(OC(=O)C(=C)C)ccc2c1]

RM-4

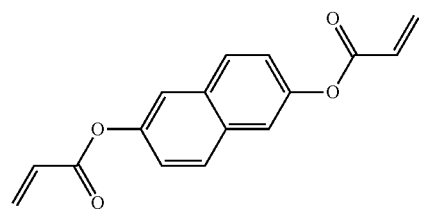 [SMILES: C=CC(=O)Oc1ccc2cc(OC(=O)C=C)ccc2c1]

RM-5

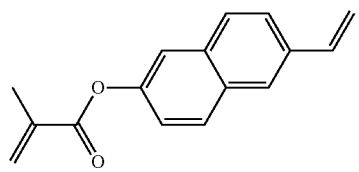 [SMILES: C=Cc1ccc2cc(OC(=O)C(=C)C)ccc2c1]

RM-6

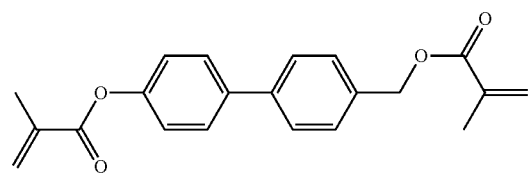 [SMILES: C=C(C)C(=O)OCc1ccc(-c2ccc(OC(=O)C(=C)C)cc2)cc1]

RM-7

TABLE F-continued
Table F shows example compounds which can preferably
be used in the mixtures according to the invention as polymerisable compounds (reactive
mesogenic compounds) for the preparation, for example, of PSV, PS-VA, PS-IPS or PS-FFS mixtures.
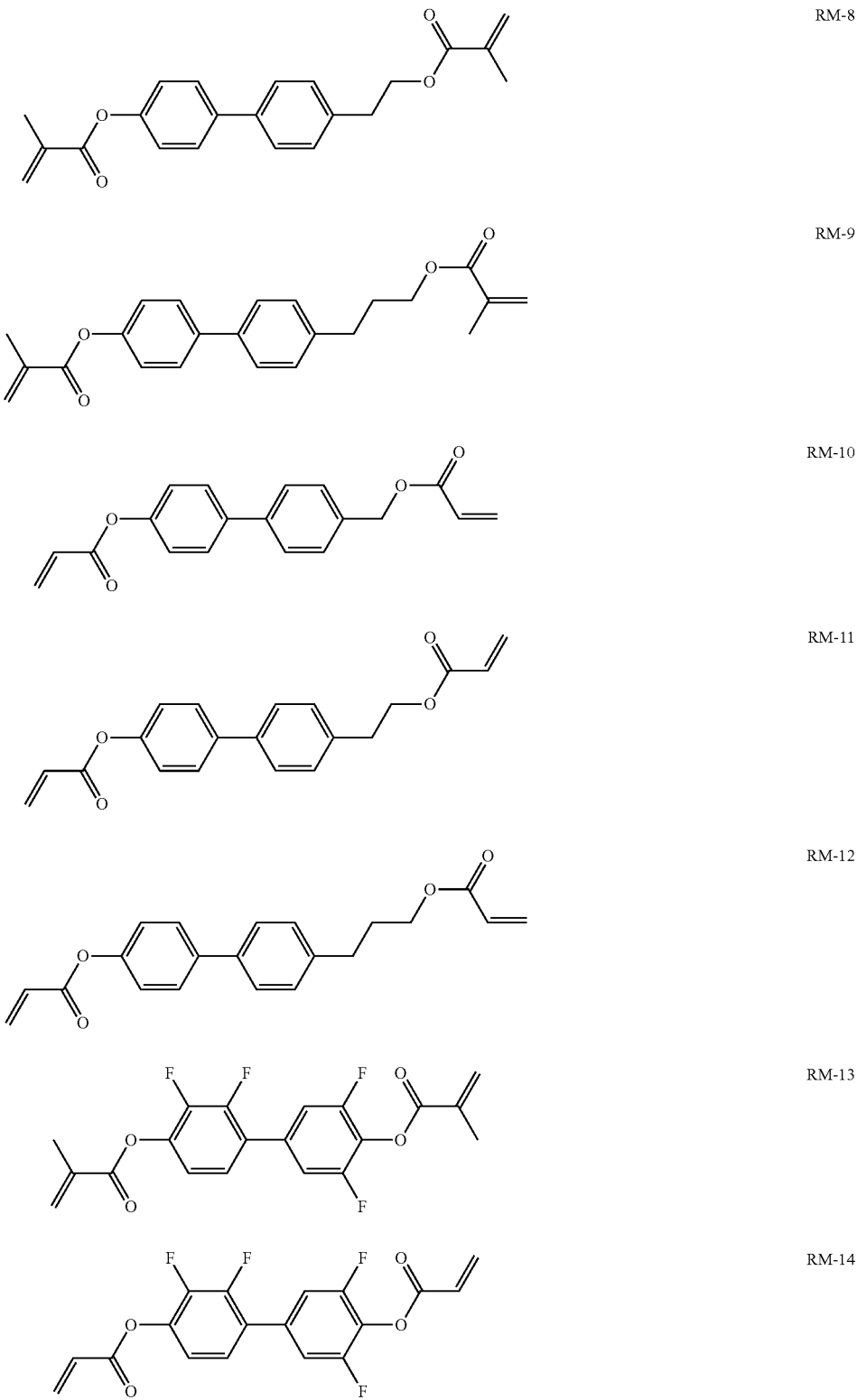

TABLE F-continued
Table F shows example compounds which can preferably
be used in the mixtures according to the invention as polymerisable compounds (reactive
mesogenic compounds) for the preparation, for example, of PSV, PS-VA, PS-IPS or PS-FFS mixtures.
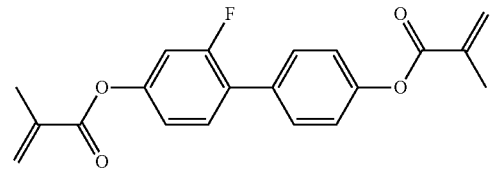 [SMILES: C=C(C)C(=O)Oc1ccc(-c2ccc(OC(=O)C(=C)C)cc2F)cc1]
RM-15
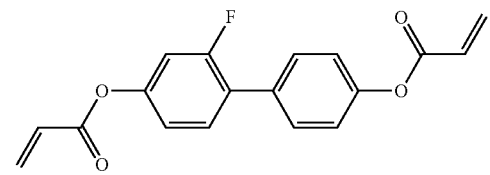 [SMILES: C=CC(=O)Oc1ccc(-c2ccc(OC(=O)C=C)cc2F)cc1]
RM-16
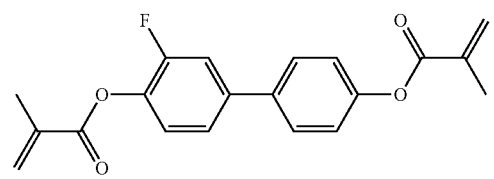 [SMILES: C=C(C)C(=O)Oc1ccc(-c2ccc(OC(=O)C(=C)C)c(F)c2)cc1]
RM-17
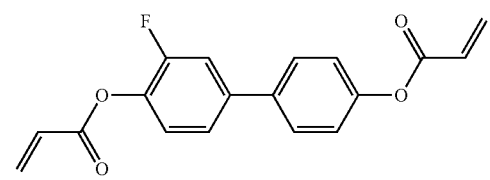
RM-18
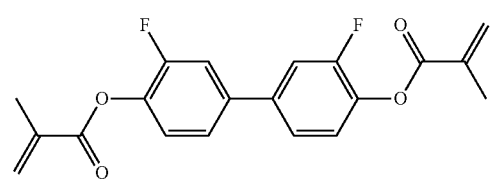 [SMILES: C=C(C)C(=O)Oc1ccc(-c2ccc(OC(=O)C(=C)C)c(F)c2)cc1F]
RM-19
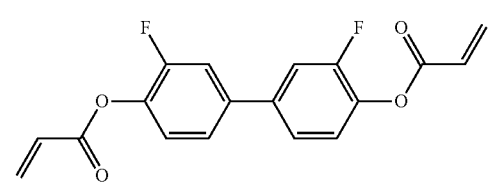
RM-20
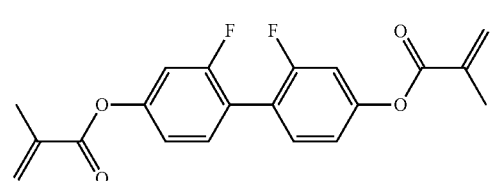
RM-21
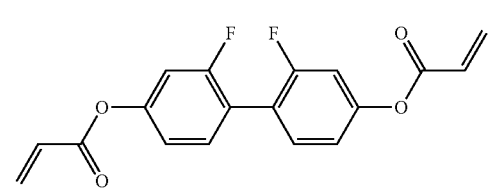 [SMILES: C=CC(=O)Oc1ccc(-c2ccc(OC(=O)C=C)cc2F)c(F)c1]
RM-22

TABLE F-continued
Table F shows example compounds which can preferably
be used in the mixtures according to the invention as polymerisable compounds (reactive
mesogenic compounds) for the preparation, for example, of PSV, PS-VA, PS-IPS or PS-FFS mixtures.
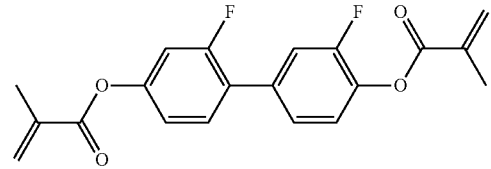 [SMILES: C=C(C)C(=O)Oc1ccc(-c2ccc(OC(=O)C(=C)C)c(F)c2)c(F)c1] RM-23
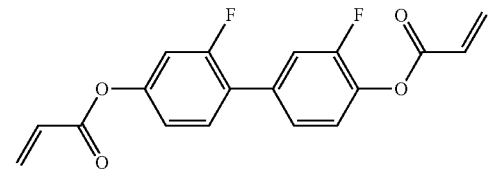 [SMILES: C=CC(=O)Oc1ccc(-c2ccc(OC(=O)C=C)c(F)c2)c(F)c1] RM-24
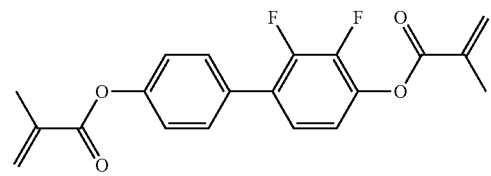 [SMILES: C=C(C)C(=O)Oc1ccc(-c2ccc(OC(=O)C(=C)C)c(F)c2F)cc1] RM-25
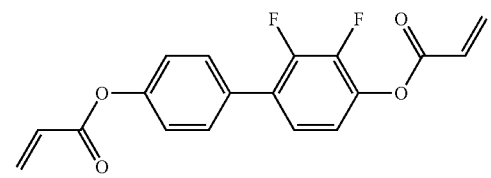 [SMILES: C=CC(=O)Oc1ccc(-c2ccc(OC(=O)C=C)c(F)c2F)cc1] RM-26
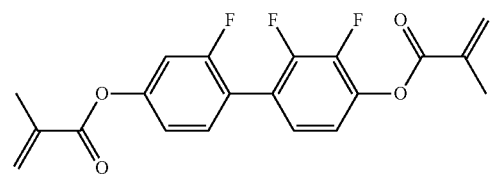 [SMILES: C=C(C)C(=O)Oc1ccc(-c2ccc(OC(=O)C(=C)C)c(F)c2F)c(F)c1] RM-27
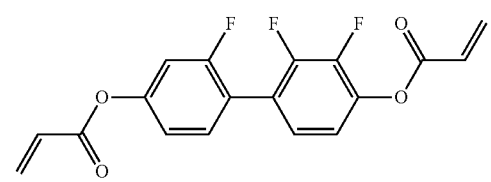 RM-28
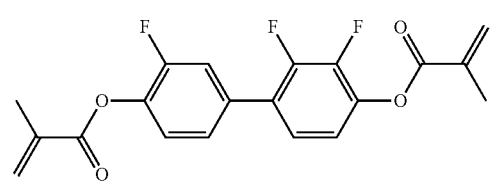 [SMILES: C=C(C)C(=O)Oc1ccc(-c2ccc(OC(=O)C(=C)C)c(F)c2F)cc1F] RM-29
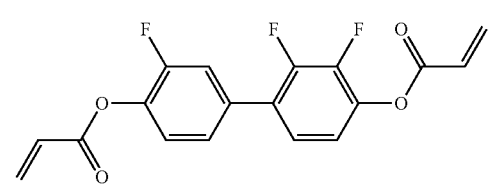 [SMILES: C=CC(=O)Oc1ccc(-c2ccc(OC(=O)C=C)c(F)c2F)cc1F] RM-30

TABLE F-continued
Table F shows example compounds which can preferably
be used in the mixtures according to the invention as polymerisable compounds (reactive
mesogenic compounds) for the preparation, for example, of PSV, PS-VA, PS-IPS or PS-FFS mixtures.
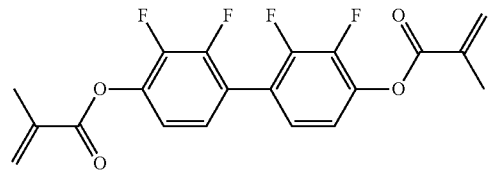 [SMILES: C=C(C)C(=O)Oc1ccc(-c2ccc(OC(=O)C(=C)C)c(F)c2F)c(F)c1F] RM-31
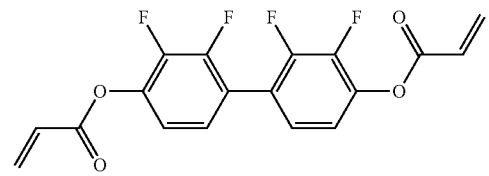 [SMILES: C=CC(=O)Oc1ccc(-c2ccc(OC(=O)C=C)c(F)c2F)c(F)c1F] RM-32
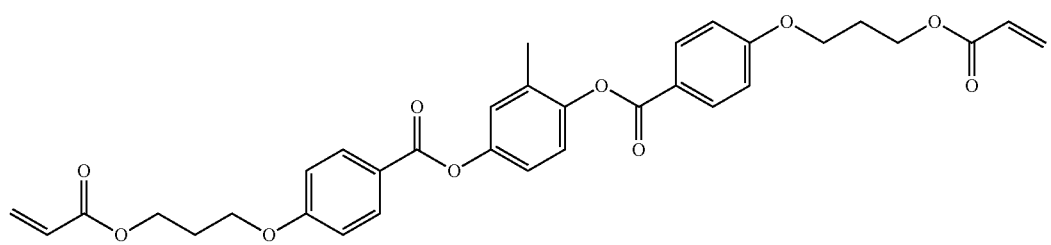 [SMILES: C=CC(=O)OCCCOc1ccc(C(=O)Oc2ccc(OC(=O)c3ccc(OCCCOC(=O)C=C)cc3)c(C)c2)cc1] RM-33
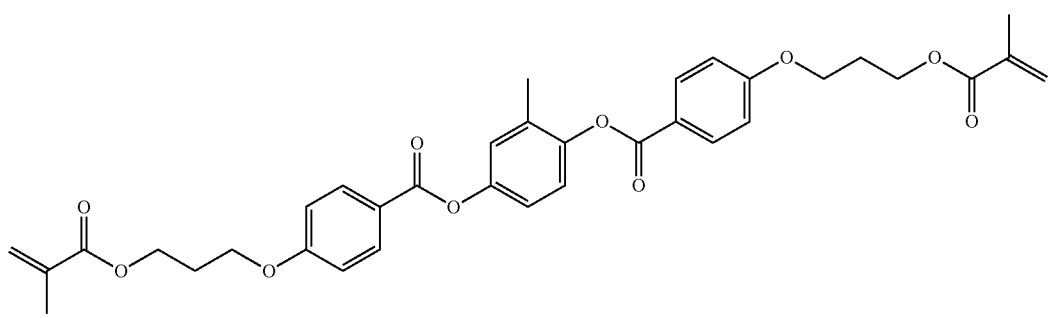 [SMILES: C=C(C)C(=O)OCCCOc1ccc(C(=O)Oc2ccc(OC(=O)c3ccc(OCCCOC(=O)C(=C)C)cc3)c(C)c2)cc1] RM-34
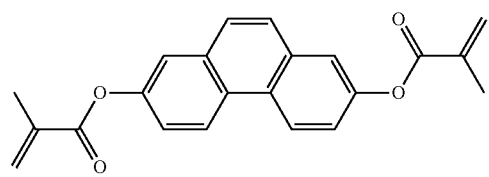 [SMILES: C=C(C)C(=O)Oc1ccc2c(ccc3cc(OC(=O)C(=C)C)ccc32)c1] RM-35
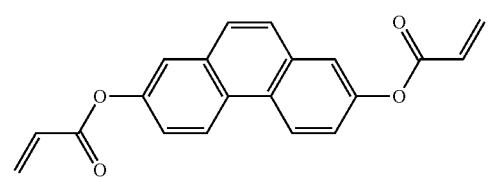 [SMILES: C=CC(=O)Oc1ccc2c(ccc3cc(OC(=O)C=C)ccc32)c1] RM-36
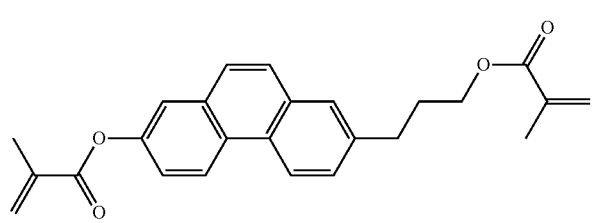 [SMILES: C=C(C)C(=O)OCCCc1ccc2c(ccc3cc(OC(=O)C(=C)C)ccc32)c1] RM-37

TABLE F-continued
Table F shows example compounds which can preferably
be used in the mixtures according to the invention as polymerisable compounds (reactive
mesogenic compounds) for the preparation, for example, of PSV, PS-VA, PS-IPS or PS-FFS mixtures.
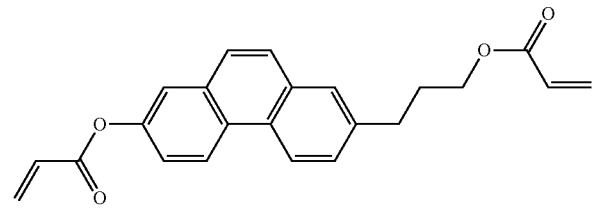 [SMILES: C=CC(=O)OCCCc1ccc2c(ccc3cc(OC(=O)C=C)ccc32)c1] RM-38
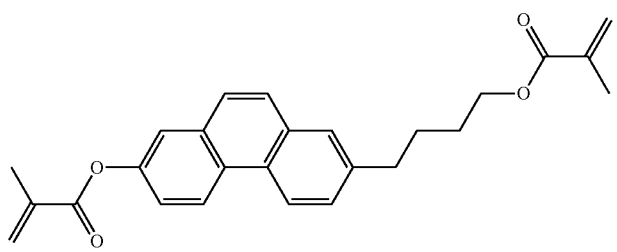 [SMILES: C=C(C)C(=O)OCCCCc1ccc2c(ccc3cc(OC(=O)C(=C)C)ccc32)c1] RM-39
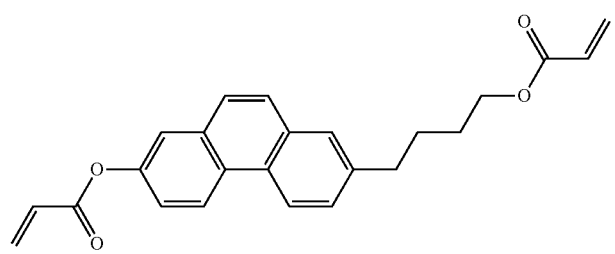 [SMILES: C=CC(=O)OCCCCc1ccc2c(ccc3cc(OC(=O)C=C)ccc32)c1] RM-40
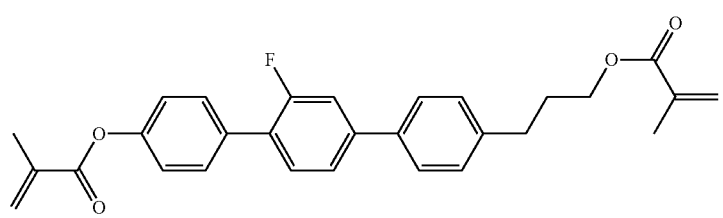 [SMILES: C=C(C)C(=O)OCCCc1ccc(-c2ccc(-c3ccc(OC(=O)C(=C)C)cc3)c(F)c2)cc1] RM-41
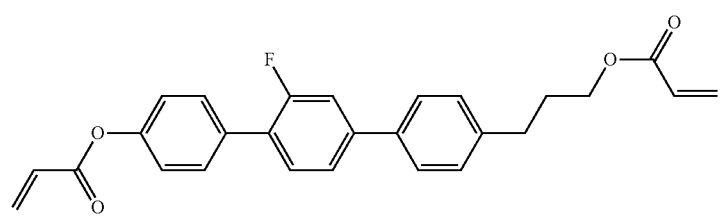 [SMILES: C=CC(=O)OCCCc1ccc(-c2ccc(-c3ccc(OC(=O)C=C)cc3)c(F)c2)cc1] RM-42
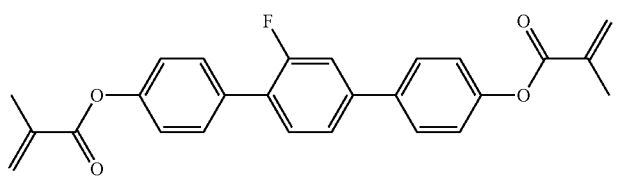 [SMILES: C=C(C)C(=O)Oc1ccc(-c2ccc(-c3ccc(OC(=O)C(=C)C)cc3)c(F)c2)cc1] RM-43
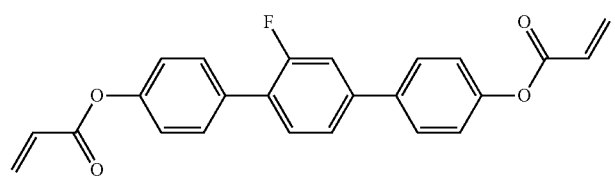 [SMILES: C=CC(=O)Oc1ccc(-c2ccc(-c3ccc(OC(=O)C=C)cc3)c(F)c2)cc1] RM-44

TABLE F-continued
Table F shows example compounds which can preferably be used in the mixtures according to the invention as polymerisable compounds (reactive mesogenic compounds) for the preparation, for example, of PSV, PS-VA, PS-IPS or PS-FFS mixtures.
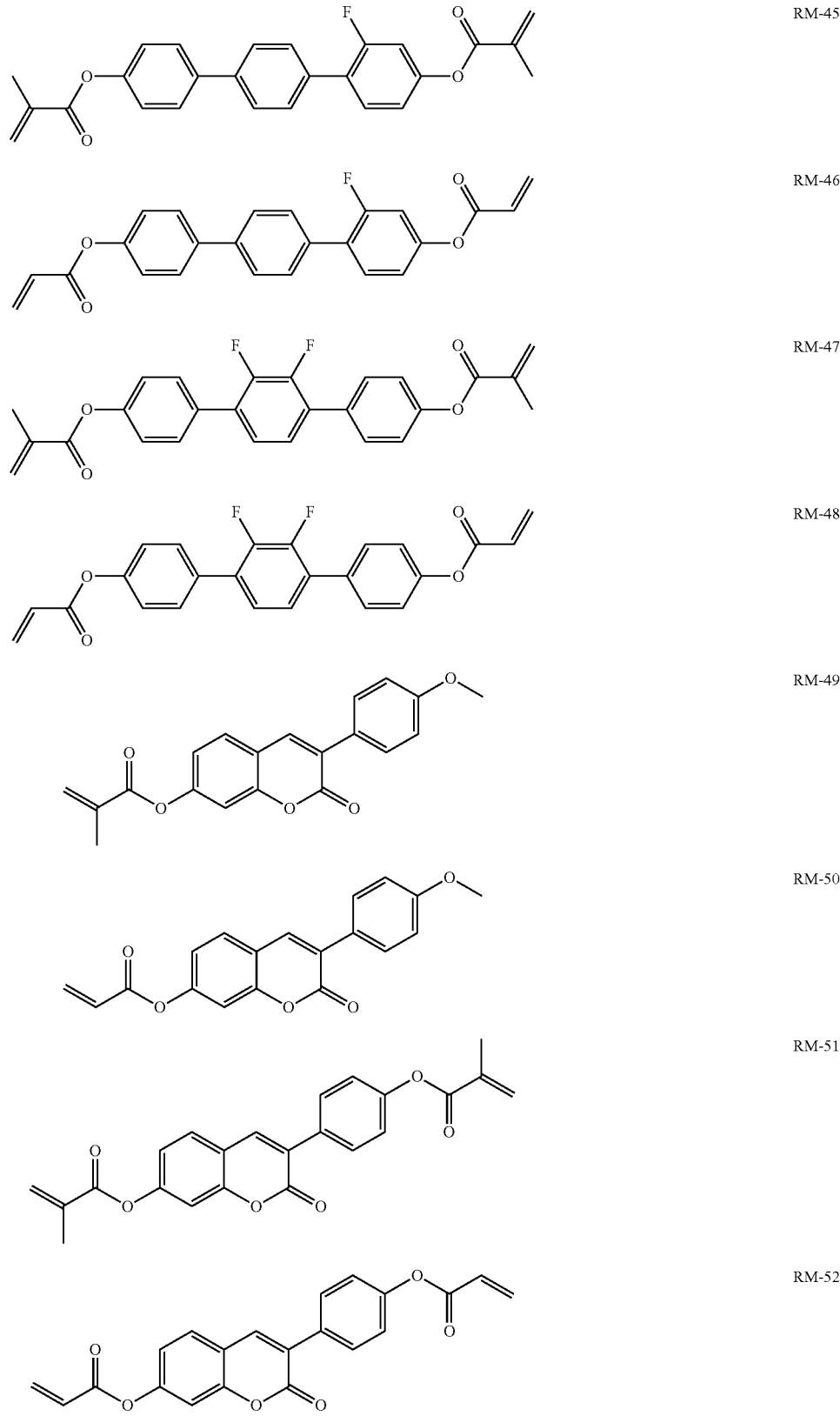

TABLE F-continued
Table F shows example compounds which can preferably
be used in the mixtures according to the invention as polymerisable compounds (reactive
mesogenic compounds) for the preparation, for example, of PSV, PS-VA, PS-IPS or PS-FFS mixtures.
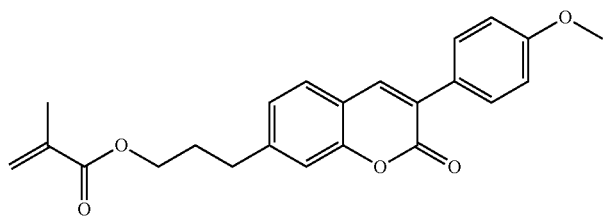 [SMILES: C=C(C)C(=O)OCCCc1ccc2cc(-c3ccc(OC)cc3)c(=O)oc2c1] RM-53
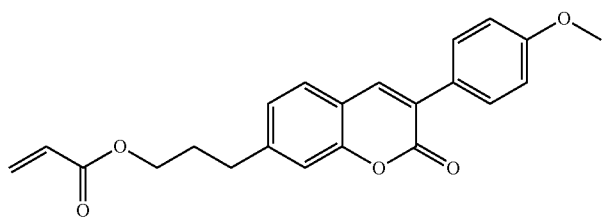 [SMILES: C=CC(=O)OCCCc1ccc2cc(-c3ccc(OC)cc3)c(=O)oc2c1] RM-54
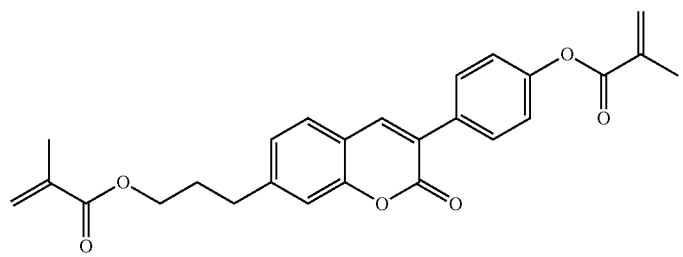 [SMILES: C=C(C)C(=O)OCCCc1ccc2cc(-c3ccc(OC(=O)C(=C)C)cc3)c(=O)oc2c1] RM-55
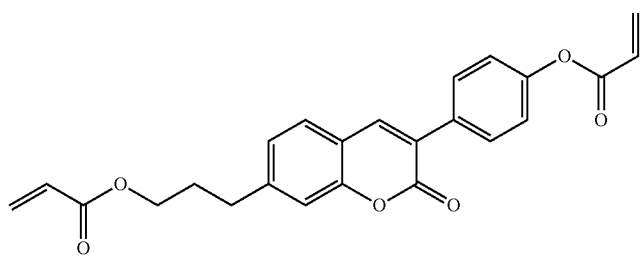 [SMILES: C=CC(=O)OCCCc1ccc2cc(-c3ccc(OC(=O)C=C)cc3)c(=O)oc2c1] RM-56
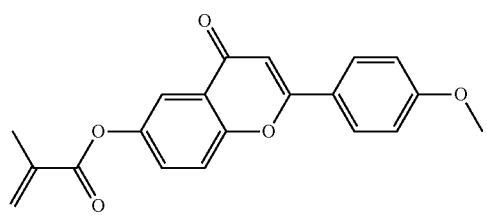 [SMILES: C=C(C)C(=O)Oc1ccc2oc(-c3ccc(OC)cc3)cc(=O)c2c1] RM-57
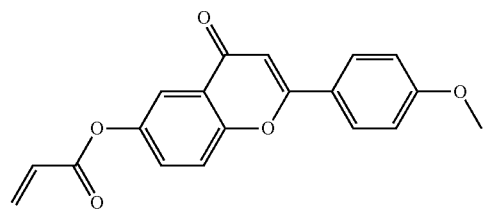 [SMILES: C=CC(=O)Oc1ccc2oc(-c3ccc(OC)cc3)cc(=O)c2c1] RM-58

TABLE F-continued
Table F shows example compounds which can preferably be used in the mixtures according to the invention as polymerisable compounds (reactive mesogenic compounds) for the preparation, for example, of PSV, PS-VA, PS-IPS or PS-FFS mixtures.
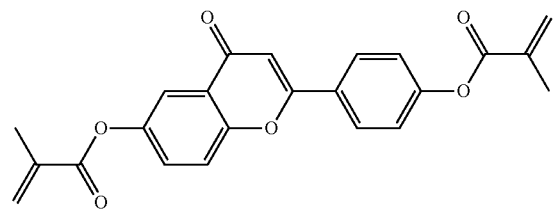 [SMILES: C=C(C)C(=O)Oc1ccc(-c2cc(=O)c3cc(OC(=O)C(=C)C)ccc3o2)cc1] RM-59
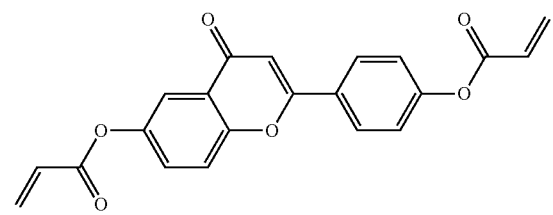 [SMILES: C=CC(=O)Oc1ccc(-c2cc(=O)c3cc(OC(=O)C=C)ccc3o2)cc1] RM-60
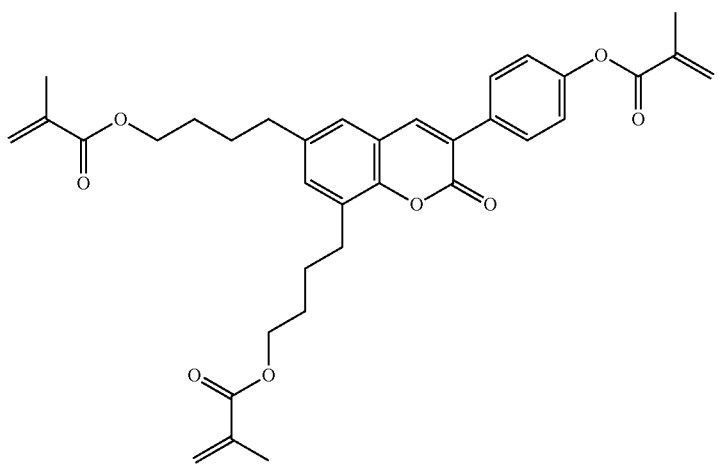 [SMILES: C=C(C)C(=O)OCCCCc1cc(CCCCOC(=O)C(=C)C)c2oc(=O)c(-c3ccc(OC(=O)C(=C)C)cc3)cc2c1] RM-61
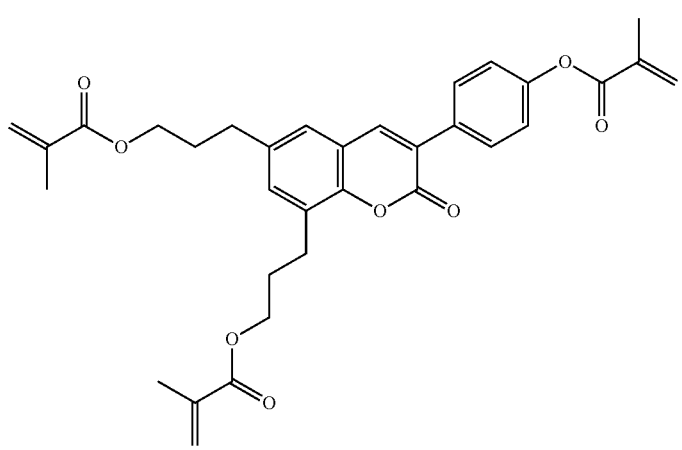 [SMILES: C=C(C)C(=O)OCCCc1cc(CCCOC(=O)C(=C)C)c2oc(=O)c(-c3ccc(OC(=O)C(=C)C)cc3)cc2c1] RM-62

TABLE F-continued
Table F shows example compounds which can preferably
be used in the mixtures according to the invention as polymerisable compounds (reactive
mesogenic compounds) for the preparation, for example, of PSV, PS-VA, PS-IPS or PS-FFS mixtures.
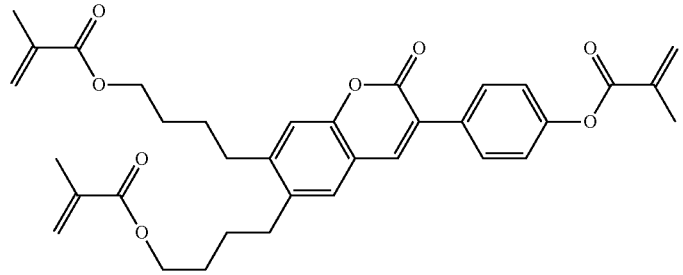 [SMILES: C=C(C)C(=O)OCCCCc1cc2cc(-c3ccc(OC(=O)C(=C)C)cc3)c(=O)oc2cc1CCCCOC(=O)C(=C)C]
RM-63
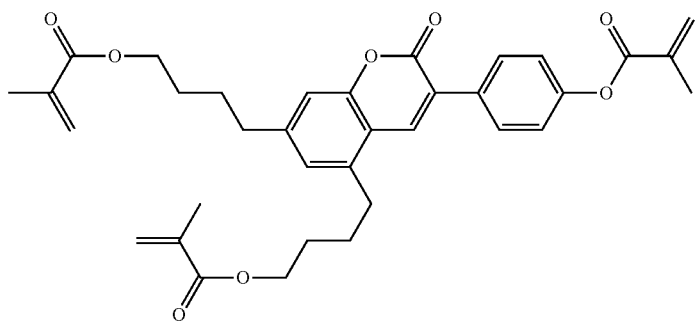 [SMILES: C=C(C)C(=O)OCCCCc1cc(CCCCOC(=O)C(=C)C)c2cc(-c3ccc(OC(=O)C(=C)C)cc3)c(=O)oc2c1]
RM-64
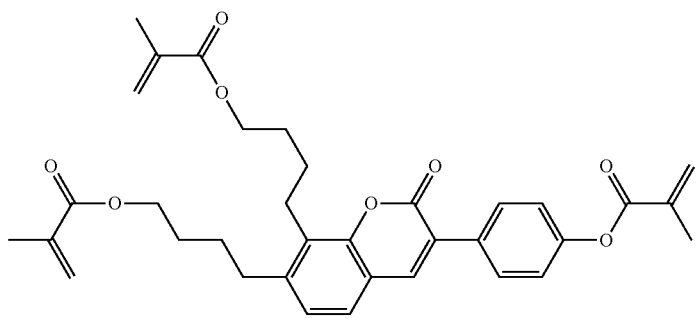 [SMILES: C=C(C)C(=O)OCCCCc1ccc2cc(-c3ccc(OC(=O)C(=C)C)cc3)c(=O)oc2c1CCCCOC(=O)C(=C)C]
RM-65
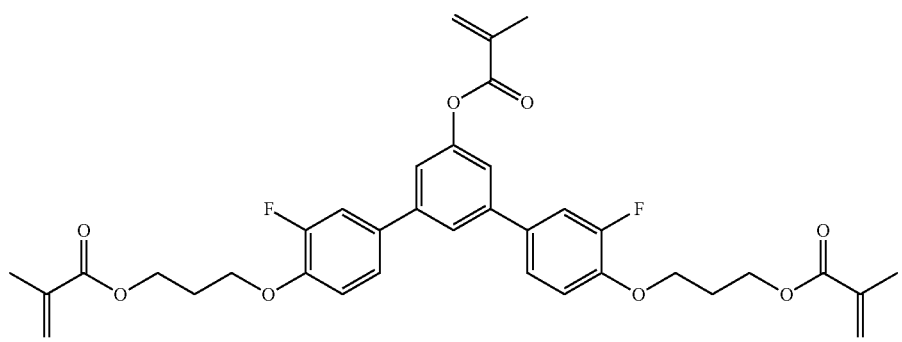 [SMILES: C=C(C)C(=O)OCCCOc1ccc(-c2cc(OC(=O)C(=C)C)cc(-c3ccc(OCCCOC(=O)C(=C)C)c(F)c3)c2)cc1F]
RM-66

TABLE F-continued
Table F shows example compounds which can preferably
be used in the mixtures according to the invention as polymerisable compounds (reactive
mesogenic compounds) for the preparation, for example, of PSV, PS-VA, PS-IPS or PS-FFS mixtures.
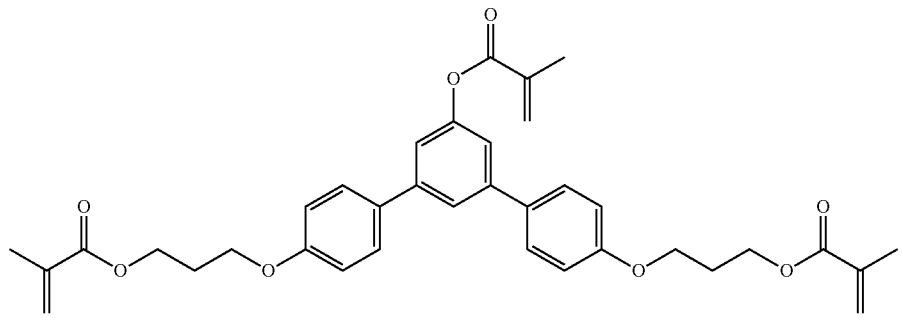 [SMILES: C=C(C)C(=O)OCCCOc1ccc(-c2cc(OC(=O)C(=C)C)cc(-c3ccc(OCCCOC(=O)C(=C)C)cc3)c2)cc1]
RM-67
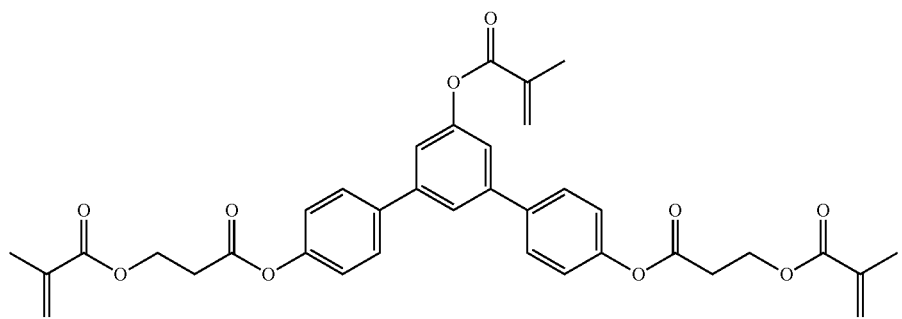 [SMILES: C=C(C)C(=O)OCCC(=O)Oc1ccc(-c2cc(OC(=O)C(=C)C)cc(-c3ccc(OC(=O)CCOC(=O)C(=C)C)cc3)c2)cc1]
RM-68
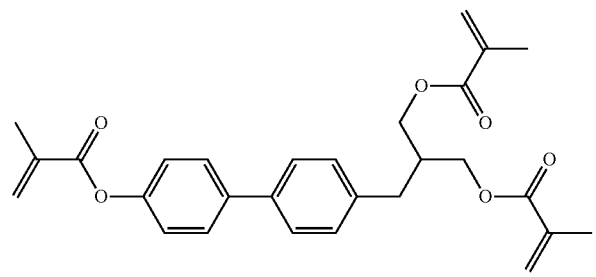 [SMILES: C=C(C)C(=O)OCC(COC(=O)C(=C)C)Cc1ccc(-c2ccc(OC(=O)C(=C)C)cc2)cc1]
RM-69
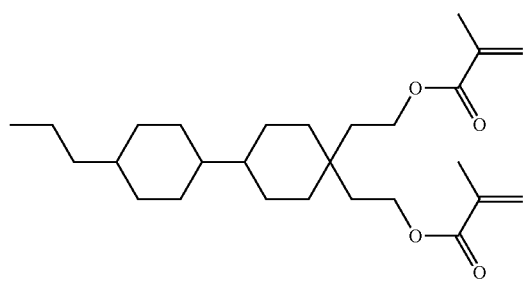 [SMILES: C=C(C)C(=O)OCCC1(CCOC(=O)C(=C)C)CCC(C2CCC(CCC)CC2)CC1]
RM-70
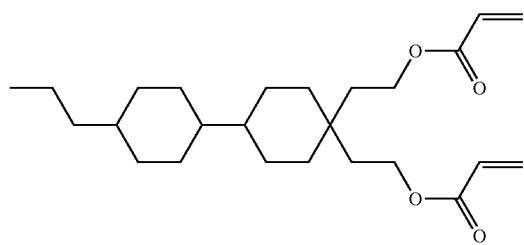 [SMILES: C=CC(=O)OCCC1(CCOC(=O)C=C)CCC(C2CCC(CCC)CC2)CC1]
RM-71

TABLE F-continued
Table F shows example compounds which can preferably
be used in the mixtures according to the invention as polymerisable compounds (reactive
mesogenic compounds) for the preparation, for example, of PSV, PS-VA, PS-IPS or PS-FFS mixtures.
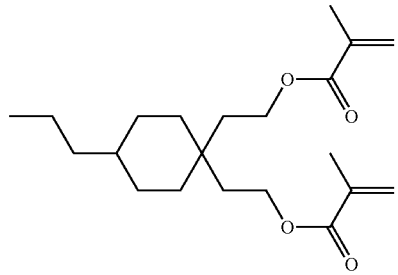 [SMILES: C=C(C)C(=O)OCCC1(CCOC(=O)C(=C)C)CCC(CCC)CC1]
RM-72
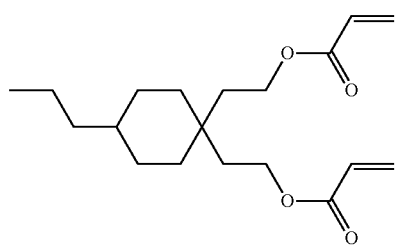 [SMILES: C=CC(=O)OCCC1(CCOC(=O)C=C)CCC(CCC)CC1]
RM-73
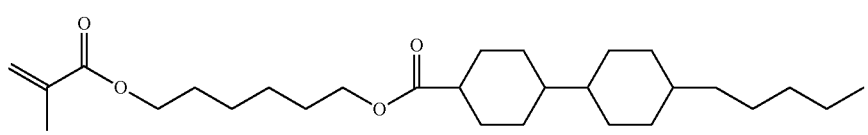 [SMILES: C=C(C)C(=O)OCCCCCCOC(=O)C1CCC(C2CCC(CCCCC)CC2)CC1]
RM-74
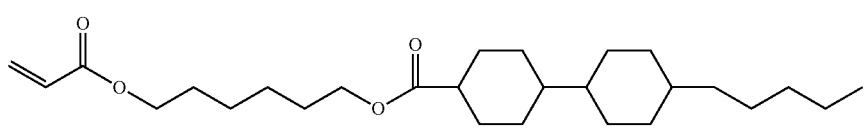 [SMILES: C=CC(=O)OCCCCCCOC(=O)C1CCC(C2CCC(CCCCC)CC2)CC1]
RM-75
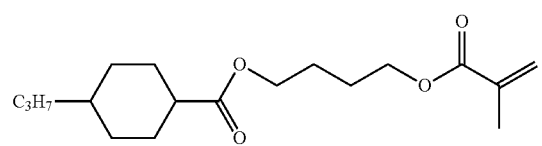
RM-76
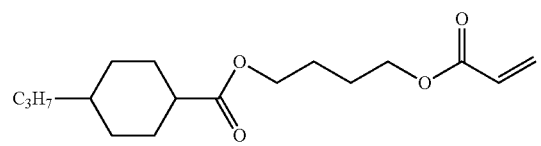
RM-77
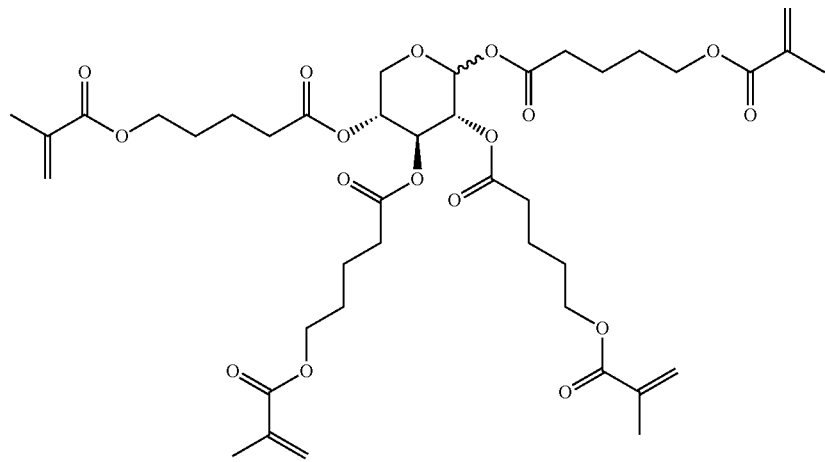 [SMILES: C=C(C)C(=O)OCCCCC(=O)OC1OC[C@@H](OC(=O)CCCCOC(=O)C(=C)C)[C@H](OC(=O)CCCCOC(=O)C(=C)C)[C@H]1OC(=O)CCCCOC(=O)C(=C)C]
RM-78

TABLE F-continued
Table F shows example compounds which can preferably be used in the mixtures according to the invention as polymerisable compounds (reactive mesogenic compounds) for the preparation, for example, of PSV, PS-VA, PS-IPS or PS-FFS mixtures.
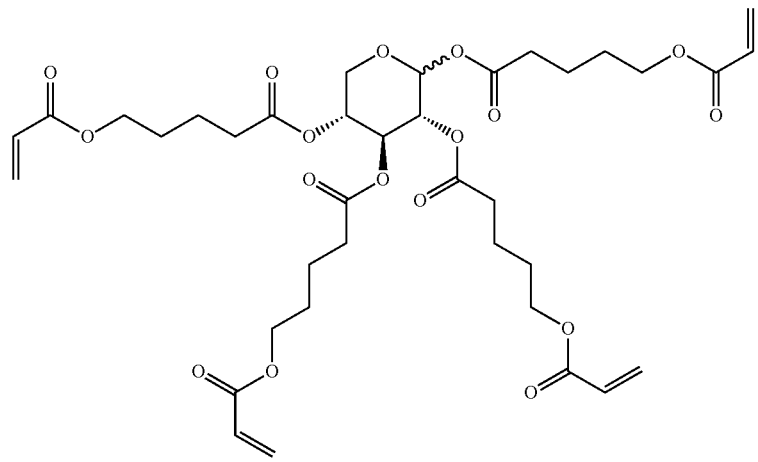 [SMILES: C=CC(=O)OCCCCC(=O)OC1OC[C@@H](OC(=O)CCCCOC(=O)C=C)[C@H](OC(=O)CCCCOC(=O)C=C)[C@H]1OC(=O)CCCCOC(=O)C=C]
RM-79
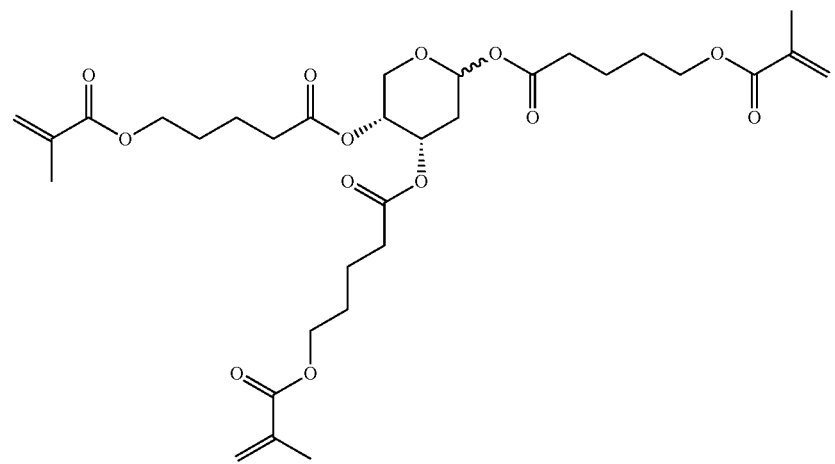 [SMILES: C=C(C)C(=O)OCCCCC(=O)OC1C[C@H](OC(=O)CCCCOC(=O)C(=C)C)[C@H](OC(=O)CCCCOC(=O)C(=C)C)CO1]
RM-80
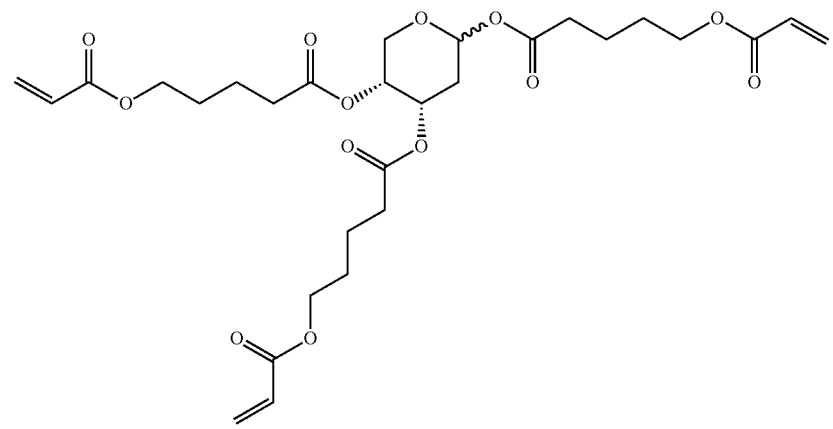 [SMILES: C=CC(=O)OCCCCC(=O)OC1C[C@H](OC(=O)CCCCOC(=O)C=C)[C@H](OC(=O)CCCCOC(=O)C=C)CO1]
RM-81

TABLE F-continued

Table F shows example compounds which can preferably be used in the mixtures according to the invention as polymerisable compounds (reactive mesogenic compounds) for the preparation, for example, of PSV, PS-VA, PS-IPS or PS-FFS mixtures.

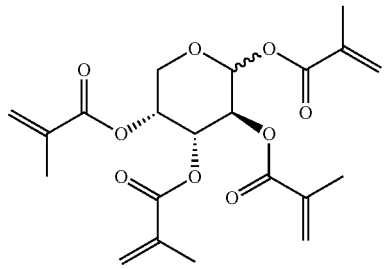 [SMILES: C=C(C)C(=O)OC1OC[C@@H](OC(=O)C(=C)C)[C@@H](OC(=O)C(=C)C)[C@@H]1OC(=O)C(=C)C]

RM-82

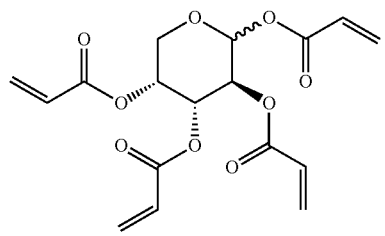 [SMILES: C=CC(=O)OC1OC[C@@H](OC(=O)C=C)[C@@H](OC(=O)C=C)[C@@H]1OC(=O)C=C]

RM-83

If the mixtures according to the invention comprise one or more mesogenic compounds, the mesogenic compound in a preferred embodiment is a compound selected from Table F.

The following examples are intended to explain the invention without limiting it.

EXAMPLES

Above and below, percentage data denote percent by weight. All temperatures are indicated in degrees Celsius. m.p. denotes melting point, cl.p.=clearing point. Furthermore, C=crystalline state, N=nematic phase, S=smectic phase and I=isotropic phase. The data between these symbols represent the transition temperatures.

All physical properties are determined in accordance with "Merck Liquid Crystals, Physical Properties of Liquid Crystals", status November 1997, Merck KGaA, Germany, and apply for a temperature of 20° C., unless explicitly indicated otherwise.

Comparative Example V1

| | | | |
|---|---|---|---|
| CC-3-V | 8.0% | Clearing point [° C.]: | 102.0 |
| CPGP-5-2 | 5.0% | S->N transition [° C.]: | −14.0 |
| CPGP-4-3 | 5.0% | Δn [589 nm, 20° C.]: | 0.1959 |
| CPGP-5-3 | 5.0% | Δε [1 kHz, 20° C.]: | 4.8 |
| CP-3-O1 | 15.0% | ε∥ [1 kHz, 20° C.]: | 8.3 |
| PGIGI-3-F | 4.0% | ε⊥ [1 kHz, 20° C.]: | 3.5 |
| PGP-2-2V | 15.0% | | |
| PGP-2-3 | 4.0% | LTS bulk [−10° C.]: | >1000 h |
| PGP-2-4 | 5.0% | LTS bulk [−25° C.]: | — |
| PGP-2-5 | 10.0% | LTS bulk [−30° C.]: | — |
| PGUQU-4-F | 4.0% | | |
| PGUQU-5-F | 3.0% | | |
| PP-1-2V1 | 7.0% | | |
| PUQU-3-F | 10.0% | | |
| G-4O-O3 | — | | |

Example M1

| | | | |
|---|---|---|---|
| CC-3-V | 8.0% | Clearing point [° C.]: | 105.5 |
| CPGP-5-2 | 5.0% | S->N transition [° C.]: | −30.0 |
| CPGP-4-3 | 6.0% | Δn [589 nm, 20° C.]: | 0.2006 |
| CPGP-5-3 | 5.0% | Δε [1 kHz, 20° C.]: | 5.3 |
| CP-3-O1 | 10.0% | ε∥ [1 kHz, 20° C.]: | 9.0 |
| PGIGI-3-F | 6.0% | ε⊥ [1 kHz, 20° C.]: | 3.7 |
| PGP-2-2V | 16.0% | | |
| PGP-2-3 | 5.0% | LTS bulk [−10° C.]: | — |
| PGP-2-4 | 5.0% | LTS bulk [−25° C.]: | >1000 h |
| PGP-2-5 | 10.0% | LTS bulk [−30° C.]: | 888 h |
| PGUQU-4-F | 6.0% | | |
| PGUQU-5-F | 3.0% | | |
| PP-1-2V1 | 3.0% | | |
| PUQU-3-F | 9.0% | | |
| G-4O-O3 | 3.0% | | |

It immediately becomes evident from the comparison of mixtures V1 and M1 (according to the invention) that the addition of small amounts of compound G-4O—O3 enables the nematic phase range to be shifted to significantly lower temperatures. At the same time, both the Δn is increased from 0.1959 to 0.2006 and also the low-temperature stability (LTS bulk) is significantly improved from −10° C. to −30° C.

Example M2

| | | | |
|---|---|---|---|
| CC-3-V | 38.0% | Clearing point [° C.]: | 78.0 |
| CCP-V-1 | 6.0% | | |
| CCP-3-OT | 9.0% | Δn [589 nm, 20° C.]: | 0.1066 |
| CPGP-4-3 | 6.0% | Δε [1 kHz, 20° C.]: | 9.4 |
| APUQU-2-F | 8.0% | ε∥ [1 kHz, 20° C.]: | 13.4 |
| APUQU-3-F | 8.5% | ε⊥ [1 kHz, 20° C.]: | 4.0 |
| PGUQU-3-F | 3.0% | | |
| PGUQU-4-F | 7.0% | LTS bulk [−20° C.]: | >1000 h |
| DPGU-4-F | 5.0% | LTS bulk [−25° C.]: | >1000 h |
| CPY-2-O2 | 1.5% | LTS bulk [−30° C.]: | >1000 h |
| G-4O-O3 | 8.0% | | |

Example M3

| | | | |
|---|---|---|---|
| CC-3-V | 44.0% | Clearing point [° C.]: | 79.0 |
| APUQU-2-F | 8.5% | | |
| APUQU-3-F | 8.0% | Δn [589 nm, 20° C.]: | 0.1084 |
| CCP-3-OT | 6.0% | Δε [1 kHz, 20° C.]: | 9.6 |
| CCP-V-1 | 8.0% | $\varepsilon_\parallel$ [1 kHz, 20° C.]: | 13.2 |
| PGUQU-4-F | 4.5% | $\varepsilon_\perp$ [1 kHz, 20° C.]: | 3.5 |
| PGP-2-2V | 7.5% | | |
| DPGU-4-F | 5.5% | LTS bulk [−20° C.]: | >1000 h |
| PUQU-3-F | 6.5% | LTS bulk [−25° C.]: | >1000 h |
| G-4O-O3 | 1.5% | LTS bulk [−30° C.]: | 24 h |

Example M4

| | | | |
|---|---|---|---|
| CC-3-V | 25.0% | Clearing point [° C.]: | 80.0 |
| CC-3-V1 | 6.0% | | |
| CC-3-2V1 | 4.0% | Δn [589 nm, 20° C.]: | 0.1108 |
| CCP-V-1 | 15.0% | Δε [1 kHz, 20° C.]: | 10.9 |
| CCP-3OCF3 | 3.0% | $\varepsilon_\parallel$ [1 kHz, 20° C.]: | 14.9 |
| APUQU-3-F | 4.0% | $\varepsilon_\perp$ [1 kHz, 20° C.]: | 4.0 |
| CDUQU-3-F | 7.0% | | |
| DGUQU-4-F | 5.0% | LTS bulk [−30° C.]: | >744 h |
| DPGU-4-F | 5.5% | | |
| PGP-2-2V | 5.0% | | |
| PGUQU-3-F | 6.0% | | |
| PGUQU-4-F | 6.0% | | |
| PPGU-3-F | 0.5% | | |
| G-4O-O3 | 8.0% | | |

The invention claimed is:

1. A liquid-crystalline medium, comprising at least one compound of formula I,

                                                                  I in which
$R^1$ and $R^{1*}$ each, independently of one another, denote an alkyl or alkoxy radical having 1 to 15 C atoms, in which one or more $CH_2$ groups are optionally each replaced, independently of one another, by

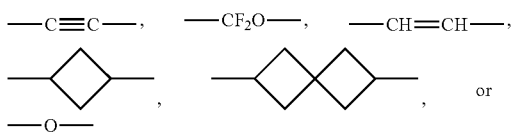

in such a way that O atoms are not linked directly to one another, and in which optionally one or more H atoms are replaced by halogen,
$A^1$ denotes

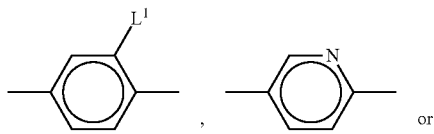

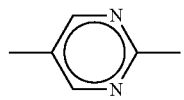

$L^1$ denotes F, Cl, $CF_3$, $OCF_3$ or $CHF_2$.

2. A liquid-crystalline medium, comprising at least one compound of formulae I-1 to I-10,

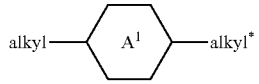
                                         I-1

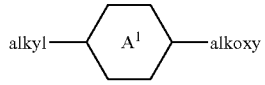
                                         I-2

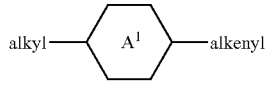
                                         I-3

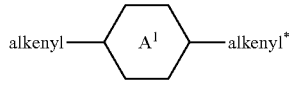
                                         I-4

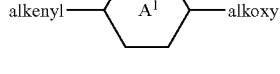
                                         I-5

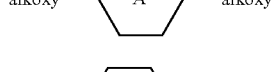
                                         I-6

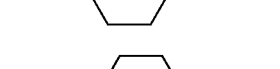
                                         I-7

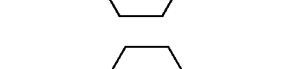
                                         I-8

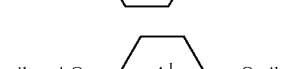
                                         I-9

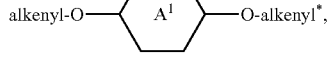
                                       I-10 in which
$A^1$ denotes

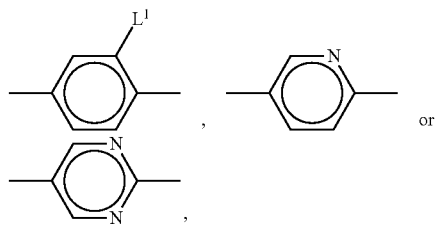

$L^1$ denotes F, Cl, $CF_3$, $OCF_3$ or $CHF_2$, alkyl and alkyl* each, independently of one another, denote a straight-chain alkyl radical having 1-6 C atoms, alkenyl and alkenyl* each, independently of one another, denote a straight-chain alkenyl radical having 2-6 C atoms, and alkoxy and alkoxy* each, independently of one another, denote a straight-chain alkoxy radical having 1-6 C atoms.

3. The liquid-crystalline medium according to claim 1, which additionally comprises one or more compounds of formulae II and/or III,

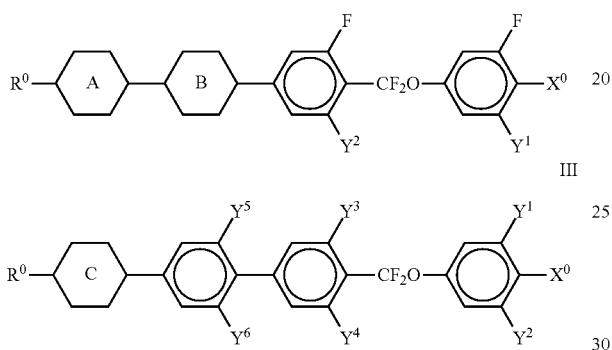

in which $R^0$ denotes a halogenated or unsubstituted alkyl or alkoxy radical having 1 to 15 C atoms, in which one or more $CH_2$ groups are optionally each replaced, independently of one another, by

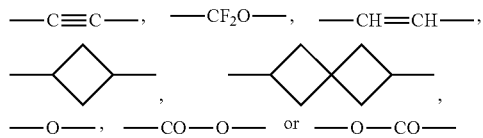

in such a way that O atoms are not linked directly to one another, $X^0$ denotes F, Cl, CN, $SF_5$, SCN, NCS, a halogenated alkyl radical, a halogenated alkenyl radical, a halogenated alkoxy radical or a halogenated alkenyloxy radical having up to 6 C atoms, $Y^{1-6}$ each, independently of one another, denote H, F or Cl,

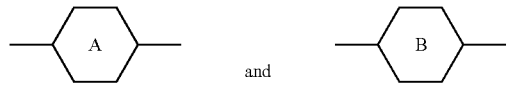

each, independently of one another, denote

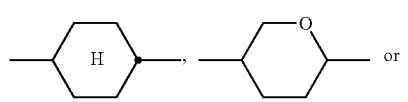

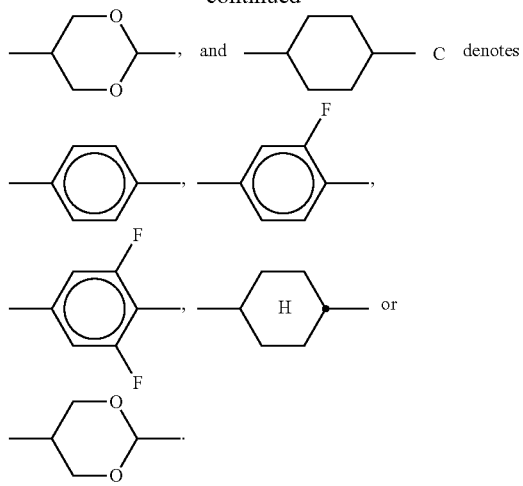

4. The liquid-crystalline medium according to claim 1, which additionally comprises one or more compounds of formulae IX to XII,

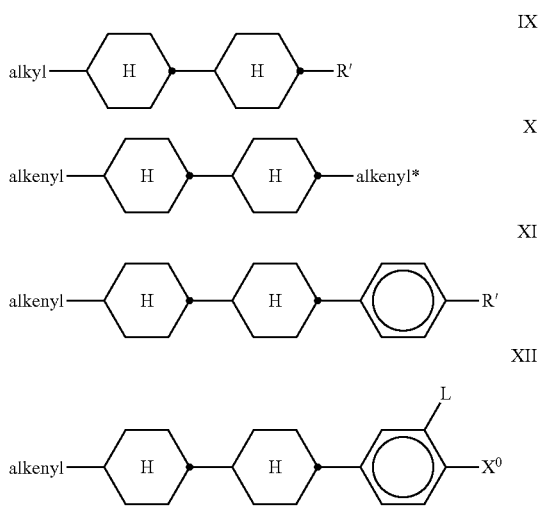

in which $X^0$ denotes F, Cl, CN, $SF_5$, SCN, NCS, a halogenated alkyl radical, a halogenated alkenyl radical, a halogenated alkoxy radical or a halogenated alkenyloxy radical having up to 6 C atoms, L denotes H or F, "alkyl" denotes $C_{1-6}$-alkyl, R' denotes $C_{1-6}$-alkyl, $C_{1-6}$-alkoxy or $C_{2-6}$-alkenyl, and "alkenyl" and "alkenyl*" each, independently of one another, denote $C_{2-6}$-alkenyl.

5. The liquid-crystalline medium according to claim 1, which additionally comprises one or more compounds of formula XIII,

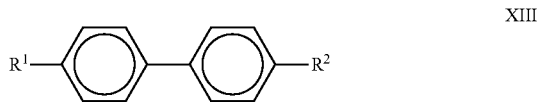

in which

R¹ and R² each, independently of one another, denote n-alkyl, alkoxy, oxaalkyl, fluoroalkyl or alkenyl, each having up to 6 C atoms.

6. The liquid-crystalline medium according to claim 1, which additionally comprises one or more compounds of formula XVII,

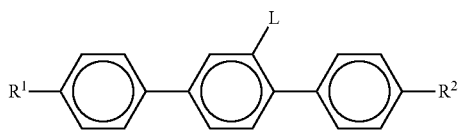

XVII in which

R¹ and R² each, independently of one another, denote n-alkyl, alkoxy, oxaalkyl, fluoroalkyl or alkenyl, each having up to 8 C atoms, and L denotes H or F.

7. The liquid-crystalline medium according to claim 1, which additionally comprises one or more compounds of formulae XXVII, XXVIII and/or XXIX,

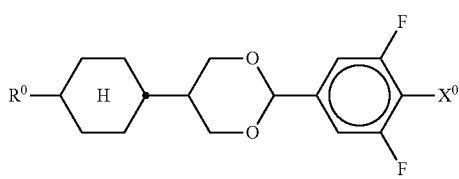

XXVII

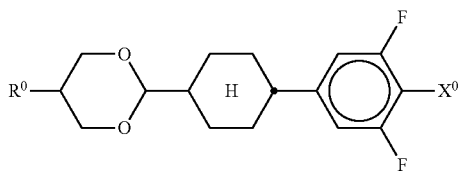

XXVIII

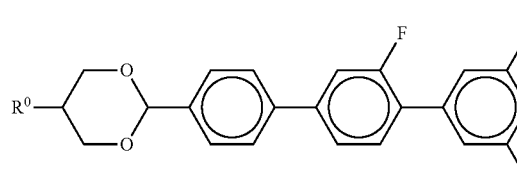

XXIX in which

R⁰ denotes a halogenated or unsubstituted alkyl or alkoxy radical having 1 to 15 C atoms, in which one or more CH₂ groups are optionally each replaced, independently of one another, by

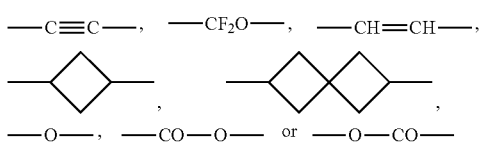

in such a way that O atoms are not linked directly to one another, and $X^0$ denotes F, Cl, CN, SF₅, SCN, NCS, a halogenated alkyl radical, a halogenated alkenyl radical, a halogenated alkoxy radical or a halogenated alkenyloxy radical having up to 6 C atoms.

8. The liquid-crystalline medium according to claim 1, which additionally comprises one or more compounds of formulae XIX, XX, XXI, XXII, XXIII and/or XXIV,

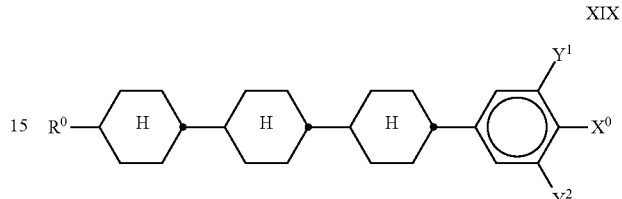

XIX

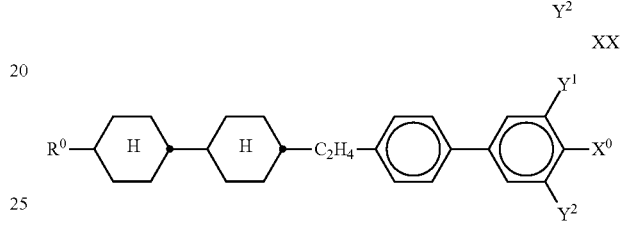

XX

XXI

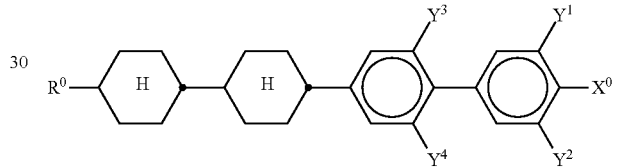

XXII

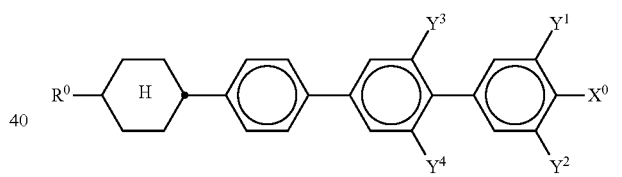

XXIII

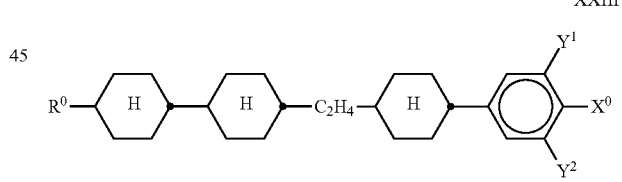

XXIV in which

R⁰ denotes a halogenated or unsubstituted alkyl or alkoxy radical having 1 to 15 C atoms, in which one or more CH₂ groups are optionally each replaced, independently of one another, by

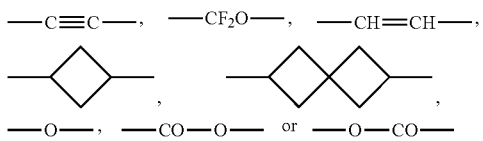

in such a way that O atoms are not linked directly to one another,

X⁰ denotes F, Cl, CN, SF$_5$, SCN, NCS, a halogenated alkyl radical, a halogenated alkenyl radical, a halogenated alkoxy radical or a halogenated alkenyloxy radical having up to 6 C atoms, and Y$^{1-4}$ each, independently of one another, denote H or F.

9. The liquid-crystalline medium according to claim 1, which additionally comprises one or more additive(s) selected from the group consisting of UV stabilisers, dopants and antioxidants.

10. The liquid-crystalline medium according to claim 1, which additionally comprises one or more polymerisable compounds.

11. A process for preparing the liquid-crystalline medium according to claim 1, comprising mixing one or more compounds of formula I with further liquid-crystalline compounds and optionally also with one or more additives and/or at least one polymerisable compound.

12. An electro-optical device, comprising the liquid-crystalline medium according to claim 1.

13. The electro-optical device according to claim 12, which is selected from the group consisting of shutter glasses, 3D applications, TN, PS-TN, STN, TN-TFT, OCB, IPS, PS-IPS, FFS, PS-FFS and PS-VA-IPS displays.

14. An electro-optical liquid-crystal display containing a liquid-crystalline medium according to claim 1.

15. The liquid-crystalline medium according to claim 1, wherein
A$^1$ denotes

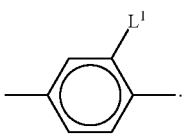

16. The liquid-crystalline medium according to claim 1, wherein
A$^1$ denotes

17. The liquid-crystalline medium according to claim 1, wherein
A$^1$ denotes

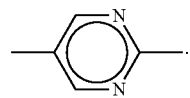

18. The liquid-crystalline medium according to claim 2, wherein
A$^1$ denotes

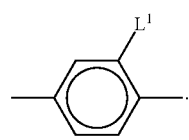

19. The liquid-crystalline medium according to claim 2, wherein
A$^1$ denotes

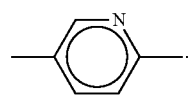

20. The liquid-crystalline medium according to claim 2, wherein
A$^1$ denotes

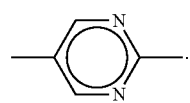

* * * * *